US006994807B2

(12) United States Patent
Tanner

(10) Patent No.: US 6,994,807 B2
(45) Date of Patent: Feb. 7, 2006

(54) ELECTROLYTIC PEROVSKITES

(75) Inventor: Cameron W. Tanner, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 285 days.

(21) Appl. No.: 10/253,840

(22) Filed: Sep. 24, 2002

(65) Prior Publication Data

US 2004/0062968 A1 Apr. 1, 2004

(51) Int. Cl.
*H01B 1/08* (2006.01)
*C04B 35/46* (2006.01)
*C01D 1/02* (2006.01)
*C01F 17/00* (2006.01)
*H01M 8/10* (2006.01)

(52) U.S. Cl. .................... 252/518.1; 252/519; 501/134; 423/594.15; 423/594.16; 423/594.17; 429/30

(58) Field of Classification Search ............. 252/519.1, 252/518, 519; 501/134; 423/594.15, 594.16, 423/594.17; 429/30
See application file for complete search history.

(56) References Cited

U.S. PATENT DOCUMENTS

| | | | | | |
|---|---|---|---|---|---|
| 4,130,694 | A | * | 12/1978 | Glass et al. .................. | 429/321 |
| 5,314,508 | A | * | 5/1994 | Taniguchi et al. .......... | 29/623.5 |
| 5,403,461 | A | * | 4/1995 | Tuller et al. ................ | 204/252 |
| 5,509,189 | A | * | 4/1996 | Tuller et al. ................ | 29/623.1 |
| 2002/0060306 | A1 | * | 5/2002 | Nishida et al. ......... | 252/62.9 R |

OTHER PUBLICATIONS

Sebastian et al, "New Lithium-ion conducting perovskite oxides related to (Li, La)TiO3," Proc. Indian. Acad. Sci. (Chem. Sci.), 2001, 113, pp 427-433.*

Nakayama et al, "Ionic Conduction of Lithium in B-site substituted perovskite compounds, (Li0.1La0.3) yMxNb1-xO3(M=Zr, Ti, Ta)," J. Mater. Chem., 2002, 12 (5), 1500-1504.*

Shan et al, "Preparation and Characterizations of new perovskite oxides (LaxNa1-3x-yLiyo2x)NbO3(0.0<x and y<0.2)," Solid State Ionics, 1998, 108, pp 403-406.*

Sugihara et al, "Lithium Ion conductivity in new Li-ADPRESSS La0.56-xM(I)xLi0.33Ta2-XTi1-2xO3," Electrothermics in japan IV, Proceedings of 20th Electronics Division of Meeting of the Ceramic Society of japan, Kawasaki, Japan., Oct. 2000.*

(Continued)

Primary Examiner—Mark Kopec
Assistant Examiner—Kallambella Vijayakumar
(74) Attorney, Agent, or Firm—Gregory V. Bean; Thomas R. Beall

(57) ABSTRACT

An electrolytic perovskite and method for synthesizing the electrolytic perovskite are described herein. Basically, the electrolytic perovskite is a solid that has an ion conductivity greater than $10^{-5}$ S/cm in a temperature range of 0–400° C., wherein the ion is $Li^+$, $H^+$, $Cu^+$, $Ag^+$, $Na^+$ or $Mg^{2+}$. For example, $Li_{1/8}Na_{3/8}La_{1/4}Zr_{1/4}Nb_{3/4}O_3$ ($5.26\times10^{-4}$ S/cm) and $Li_{1/8}K_{1/2}La_{1/8}NbO_3$ ($2.86\times10^{-3}$ S/cm) are two electrolytic perovskites that have been synthesized in accordance with the present invention that have a high $Li^+$ conductivity at 20° C. Both compositions have been confirmed in experiments to conduct $Ag^+$ and $H^+$ ions, as well. The present invention also includes a solid proton conductor that can be formed from the electrolytic perovskite by replacing the ions located therein with protons. The electrolytic perovskite and solid proton conductor can be used in a wide variety of applications or devices including, for example, a fuel cell, a membrane reactor, an amperometric hydrocarbon sensor or a steam electrolysis application.

10 Claims, 26 Drawing Sheets

OTHER PUBLICATIONS

Baldi et al, "Proton Exchanged Waveguides in LiNbO3 and LiTaO3 for integrated Lasers and Nonlinear Frequency Converters," Opt. Eng., 1998, 37(4), pp 1193-1202.*

Inaguma et al., "Candidate compounds with perovskitestructure for high lithium ionic conductivity,", Solid State Inoics, 1994, 70/71, pp 196-202.*

Slater et al, "Niobium based tetragonal tungsten bronzes as potential anodes for solid oxide fuel cells: synthesis and electrical characterization," Solid State Ionics, 1999, 120, 125-134.*

Sugiura et al, "Lithium ion Conductivity in new Li-ADPESSs La0.56−xM(I)xLi0.33Ta 2xTi1−2x03," Electrothermics in Japan IV, Proc. 20th Elec. Dv. Mtg. of Cer. Soc. of japan, Kawasaki, Japan, Oct. 2000.*

Shan et al, "Preparation and Characterization of new perovskite oxide compounds, (LaxNa1-3x-yLiyO2x)NbO3 (0.0<x and Y<0.2)," Solid State Ionics, 1998, 108 pp 403-406.*

Chuang et al, "Dependence of lithium ionic conductivity on the B-site ion substitution in (Li0.5La0.5)Ti1−xMxO3 (M=Sn, Zr, Mn, Ge)," Solid State Ionics, 1998, 107, pp 153-160.*

G.Y. Adachi, N. Imanaka, H. Aono, "Fast $Li^{30}$ Conducting Ceramic Electrolytes," Adv. Mater., 2, 127-135, (1996).

L. Latie, G. Villeneuve, D. Conte, and G. LeFlem, "Ionic Conductivity of Oxides with General Formula $Li_xLn_{1/3}Nb_{1-x}Ti_xO_3$ (Ln=La, Nd)," Journal of Solid State Chemistry, 51, 293-299, (1984).

A.G. Belous, G.N. Novitskaya, S.V. Polyanetskaya, and Y.I. Gornikov, "Study of Complex Oxides with the Composition $La_{2/3-x}Li_{3x}TiO_3$," Izv. Akad. Nauk SSSR, Neorg. Mater., 23, 412-415, (1987).

Y. Inaguma, L. Chen, M. Itoh, and T. Nakamura, "Candidate Compiounds with Perovskite Structure for High Lithium Ionics Conductivity," Solid State Ionics, 70/71, 196-202, (1994).

M. Itoh, Y. Inaguma, W.H. Jung, L. Chen, and T. Nakamura, "High Lithium Ion Conductivity in the Perovskite-Type Compounds $Ln_{1/2}Li_{1/2}TiO_3$(Ln=La, Pr, Nd, Sm)," Solid State Ionics, 70/71, 203-207, (1994).

Y. Inaguma, J. Yu, Y.J. Shan, M. Itoh, and T. Nakamura, "The Effect of the Hydrostatic Pressure on the Ionic Conductivity in Perovskite Lanthanum Lithium Titanate," J. Electrochem. Soc., 142, L8-L11, (1995).

H.T. Chung, J.G. Kim, and H.G. Kim, "Dependence of the Lithium Ionic Conductivity on the B-Site Ion Substitution in $(Li_{0.5}La_{0.5})Ti_{1-x}M_xO_3$(M=Sn, Zr, mn, Ge)," Solid State Ionics, 107, 153-160, (1998).

Y.J. Shan, N. Sinozaki, T. Nakamura, "Preparation and Characterizations of New Perovskite Oxides $(La_xNa_{1-3x-y}Li_y\square_{2x})NbO_3$ (0.0_x and y_0.2)," Solid State Ionics, 108, 403-406, (1998).

R.D. Shannon "Revised Effective Ionic Radii and Systematic Studies of Interatomic Distances in Halides and Chalcogenides", Act, Crsyt., A32, pp. 751-767 (1976).

P. Baldi, M.P.DeMicheli, K.E. Hadi, S. Nouh, A.C. Cino, P. Aschieri, and D,B. Ostrowsky, "Proton Exchanged Waveguides in LiNbO3 and LiTaO3 for integrated lasers and nonlinear frequency converters," Opt. Eng., 37(4) (1998) 1193.

C.W. Tanner and A.V. Virkar, "instability of $BaCeO_3$ in $H_2O$-Containing Atmospheres," J. Electrochem. Soc., 143 [4] (1996) 1386.

Li Jian et al. "Domain Boundary and Domain Switching in a Ceramic Rare Earth Orthoniobate $LaNbO_4$ ", J. Am. Ceram. Soc. 79, pp. 1642-1648 (1996).

B. Hanson et al. "High-Precision Analysis of hydrous Rhyolithic Glass Inclusion in Quartz Phenocrysts Using the Electron Microprobe and INAA", American Mineralogist, vVol. 81, pp. 1249-1262 (1996).

Li Jian et al. "Monoclinic-to-Tetrgonal Phase Transformation in a Ceramic Rare Earth Orthoniobate, $LaNbO_4$", J. Am. Ceram. Soc. 80, pp. 803-806 (1997).

Anthony R. West, "Solid State Chemistry and its Applications—Ionic Conductivity and Solid Electrolytes (Chapter 13)", John Wiley and Sons, pp. 452-495, 1884.

Philippe Colomban et al. "Proton Conductors Solids, Membranes and Gels-Material and Devices", Cambridge University Press, pp. 122-123, 254-257, 334-335 and 340-341, 1992.

Katsumata et al.; "New perovskite-type lithium ion conductors, LaxMyLil-3x-yNb03 (M=Ag and Na)"; Solid State Ionics, North Holland Pub. Company, Amsterdam, NL; vol. 113-115; Dec. 1, 1998; pp. 465-469.

Inaguma et al.; "Influences of carrier concentration and site percolation on lithium ion conductivity in perovskite-type oxides"; Solid States Ionics, North Holland Pub. Company, Amsterdam, NL; vol. 86-88; Jul. 1, 1996; pp. 257-260.

Sugiura et al.; "Lithium ion conductivity in new Li-ADPESSs La $_{0.56-x}M(I)_xLi_{0.33}Ta_{2x}Ti_{1-2x}O_3$"; Electroceramics in Japan IV. $20^{th}$ Electronic Division Meeting of the Ceramic Society of Japan, Kawasaki, Japan, Oct. 26-27, 2000; vol. 216, pp. 127-130.

Katsumata et al.; Influence of site percolation and local distortion on lithium ion conductivity in perovskite-type oxides $La_{0.55}Li_{0.35-x}K_xTiO_3$ and $La_{0.55}Li_{0.35}TiO_3KMO_3$ (M=Nb and Ta); Solid State Ionics, North Holland Pub. Company, Amsterdam, NL; vol. 86-88; Jul. 1, 1996; pp. 165-169.

Shan et al.; Preparation and Characterizations of new perovskite oxides $(La_xNa_{1-3x-y}Li_y\square_{2x})NbO_3$ (0.0≦x and y≦0.2); Solid State Ionics, North Holland Pub. Company, Amsterdam, NL; vol. 108, No. 1-4; May 1, 1998; pp. 403-406.

Sato, et al; "Proton Conduction of $MLaNb_2O_7$ (M=K, Na, H) with a Layered Perovskite Structure"; Journal of Solid State Chemistry; 102, pp. 557-561; 1993.

Istomin, et al; "Structures and Properties of the Perovskite-Type Compounds $Na_{1-x}Sr_xNbO_3$ (0.1≦x≦0.9)—From Insulating to Metallic Conductivity"; Journal of Solid State Chemistry; 167; pp. 7-16; 2002.

Database Inspec Online; The Institution of Electrical Engineers, Stevenage, GB; 1985, Belous A et al; "Dielectric Spectra of La/sub (2/3)-x/M/sub 3x/TiO/sub 3/perovskites" XP002284108.

* cited by examiner (A)

(B)

● *A-ion*  ● *O-ion*  ◦ *B-ion*

ELECTROLYTIC PEROVSKITES

BACKGROUND OF THE INVENTION

1. Field of the Invention

The present invention relates in general to electrolytes and, in particular, to solid electrolytic perovskites that have ion conductivities greater than $10^{-5}$ S/cm in a temperature range of 0–400° C.

2. Description of Related Art

Electrolytes play a fundamental role in areas as different as transmission of nerve signals in living organisms to the generation of electricity from chemicals in batteries. Electrolytes are able to play a fundamental role in these areas, because they have properties including, for example, rapid motion of at least one ionic species, comparatively low electronic conductivity, and a large electrolytic domain. Rapid ion motion is most commonly associated with liquid electrolytes, however, several solid electrolytes have been observed to have rapid ion motion. There has been considerable interest in the use of such solid electrolytes in fuel cells, sensors, batteries, steam electrolysis, membrane reactors etc. because they have several advantages over liquid electrolytes. For example, solid electrolytes form a more effective barrier between electrodes, do not leak, evaporate, or flood, and are less prone to parasitic electrode reactions than liquid electrolytes. Unfortunately, traditional solid electrolytes have not yet achieved wide-spread use in industry because they have or are: (1) low ionic conductivity ($<10^{-5}$ S/cm) even at temperatures as high as 600° C.; (2) expensive or difficult to synthesize and process; (3) small electrolytic domain; (4) high raw material costs; and (5) chemically unstable. Table #1 lists the room temperature ionic conductivity for some solid electrolytes, and the issues or problems preventing their usage.

production, fuel cells are considered to be an attractive alternative to diesel and coal-fired power plants for the production of electricity since they are inherently clean, more efficient, quieter, etc. The two fuel cell technologies that are viewed with the most optimism for eventual commercialization are solid oxide fuel cells (SOFC) and polymer electrolyte fuel cells (PEFC). SOFC's based upon a stabilized zirconia electrolyte must be operated at temperatures in the range 750–1000° C. to achieve sufficiently high oxygen ion conductivity. Materials capable of withstanding these high operating temperatures are costly and difficult to fabricate. As such, SOFC designers have focused on lowering the minimum operating temperature to ~650–750° C. so that cheaper electrocatalysts, seals, and interconnects may be used. On the opposite extreme, PEFC's utilize a proton conducting water-swelled polymer such as the one developed by Dow Chemical Company and sold under the trade name Nafion® that cannot be used at temperatures higher than ~90° C. (see Table #1). Because, water evaporates from the polymer at higher temperatures, and proton conductivity falls by several orders of magnitude. Fuel cell electrodes are sensitive to operating temperature, as well. Anodes of SOFC's, due to the high operating temperature, can burn reformed hydrocarbon fuels that contain CO and are resistant to poisoning by sulfur containing compounds. On the other hand, PEFC's anodes are rapidly poisoned by CO at 90° C. and are limited to clean $H_2$ as fuel. As such, a fuel cell based upon a solid proton conducting electrolyte that operates in the temperature range 200–400° C. would combine the best features of SOFC's and PEFC's, but no solid electrolyte with suitable proton conductivity and chemical stability exist in the market place prior to the present invention.

There is also strong demand for cheap, rechargeable, high power and energy density lithium ion battery. Sony offers a

TABLE #1

| MATERIAL | CONDUCTIVITY (S/cm) | ISSUES/PROBLEMS |
| --- | --- | --- |
| Proton Conductors | | |
| Nafion | $2 \times 10^{-2}$ | Operating temperature limited to <90° C. due to water loss. |
| $H_3OUO_2PO_4H_2O$ | $4 \times 10^{-3}$ | Radioactivity, expensive, water loss at temperatures >120° C. |
| Doped $BaCeO_3$ | $10^{-5}$ (500° C.) | Unstable with respect to $CO_2$ and $H_2O$, rapidly decomposes. |
| $HNbO_3$ | $5 \times 10^{-8}$ | Low conductivity, difficult to form a membrane. |
| $NH_4$-$\beta$-$Al_2O_3$ | $4 \times 10^{-4}$ | Two-dimensional conduction path, difficult to synthesize. |
| Lithium Ion Conductors | | |
| LiI-35 mol % $Al_2O_3$ | $4 \times 10^{-5}$ | Conductivity to low for most battery applications. |
| $Li_3N$ | $4 \times 10^{-4}$ | Small electrolytic domain, unstable in air. |
| $Li_2S$—$SiS_2$—$Li_3PO_4$ | $7 \times 10^{-4}$ | Deliquescent in air. |
| $Li_{1.5}Al_{0.5}Ge_{1.5}P_3O_{12}$ | $2.4 \times 10^{-4}$ | Germanium is too costly, grain boundary limited. |
| $Li_{0.33}La_{0.55}TiO_3$ | $2 \times 10^{-5}$ | Ti reduced by Li metal, grain boundary limited. |

Three notable devices that have utilized traditional solid electrolytes are cardiac pace-maker batteries, oxygen sensors for automobiles, and electrochromic windows. However, opportunities exist both for the improvement of traditional electrolytic solids and for the development of entirely new solid electrolytes. For example, in the area of energy rechargeable lithium ion battery, but it is expensive. The Sony battery is based upon a liquid $LiPF_6$ electrolyte that is toxic, corrosive, and pyrophoric in air. The recharging processes is delicate, and every Sony battery contains an electronics package which monitors and prevents overcharging that could lead to a fire. An alternative to the Sony battery is sought after, but there are no solid lithium ion conductors in the market place prior to the present invention with the right combination of materials properties and low cost. The aforementioned potential applications alone are enough to establish that there is a need and commercial value in development of new solid electrolytes. These needs and other needs are satisfied by the electrolytic perovskite, the solid proton conductor and the method of the present invention.

BRIEF DESCRIPTION OF THE INVENTION

The present invention includes an electrolytic perovskite and method for synthesizing the electrolytic perovskite. Basically, the electrolytic perovskite is a solid that has an ion conductivity greater than $10^{-5}$ S/cm in a temperature range of 0–400° C., wherein the ion is $Li^+$, $H^+$, $Cu^+$, $Ag^+$, $Na^+$ or $Mg^{2+}$. For example, $Li_{1/8}Na_{3/8}La_{1/4}Zr_{1/4}Nb_{3/4}O_3$ ($5.26 \times 10^{-4}$ S/cm) and $Li_{1/8}K_{1/2}La_{1/8}NbO_3$ ($2.86 \times 10^{-3}$ S/cm) are two electrolytic perovskites that have been synthesized in accordance with the present invention that have a high $Li^+$ conductivity at 20° C. Both compositions have been confirmed in experiments to conduct $Ag^+$ and $H^+$ ions, as well. The present invention also includes a solid proton conductor that can be formed from the electrolytic perovskite by replacing the ions located therein with protons. The electrolytic perovskite and solid proton conductor can be used in a wide variety of applications or devices including, for example, a fuel cell, a membrane reactor, an amperometric hydrocarbon sensor or a steam electrolysis application.

BRIEF DESCRIPTION OF THE DRAWINGS

A more complete understanding of the present invention may be had by reference to the following detailed description, when taken in conjunction with the accompanying drawings wherein.

DETAILED DESCRIPTION OF THE DRAWINGS

A traditional perovskite has the chemical formula $ABO_3$ and the crystal structure has three distinct sublattices. The present invention represents certain modifications to the traditional perovskite composition so as to create a solid that has high $Li^+$, $H^+$, $Cu^+$, $Ag^+$, $Na^+$, or $Mg^{2+}$ conductivity ($>10^{-5}$ S/cm) in the temperature range 0–400° C. The chemical formula for this new family of electrolytic perovskites (ionically conductive perovskites) is $E_x A'_{(z''(1-x-v)-m+x)/(z''-z')} A''_{(m-x-z'(1-x-v))/(z''-z')} B'_{(y''-6+m)/(y''-y')} B''_{(6-m-y')/(y''-y')} O_3$ where E is the mobile ion such as $Li^+$, $H^+$, $Cu^+$, $Ag^+$, $Na^+$, or $Mg^{2+}$ that resides on the A-sublattice. Concentrations of the mobile ions and vacancies are denoted by "x" and "v" in the chemical formula, respectively. The A' and A" ions with the valences z' and z", respectively, occupy A-sites and are chosen based on valence and ionic radius to increase the size of the unit cell, to accommodate a large concentration of mobile species ($0<x<3/4$), and to create a large number of vacant A-sites ($0<v<3/4$ and $x+v>0.32$). The aggregate valence per A-site is given by "m" and is adjusted to be in the range 0.0 to 2.2 where creation of A-sublattice defects is energetically easiest, and migration of mobile species is least hindered by electrostatic interactions. Typically, the A' and A" ions with the valences z' and z" are selected to satisfy the condition $z' \leq m \leq z''$. And, the B' and B" ions with the valences y' and y" are selected to satisfy the condition $y' \leq 6-m \leq y''$. Typically, A', A", B' and B" are chosen to provide stability against reduction and to enlarge the lattice parameter in the unit-cell (see, e.g., FIG. 1). Expansion of the unit cell is important since the mobile E ions cannot squeeze through interstitial spaces that are too small. Typically, A'=$Na^+$ or $K^+$, A"=$Sr^{2+}$, $Ba^{2+}$ or $La^{3+}$, and B' and B" are selected from $Zr^{4+}$, $Sn^{4+}$, $Ti^{4+}$, $Ce^{4+}$, $Hf^{4+}$, $Nb^{5+}$ or $Ta^{5+}$. Justification for these choices is discussed below.

It is well known that perovskites have interesting electrochemical properties. For example, migration of ions within perovskites and most solids for that matter occurs by hopping through interstitial spaces into vacant sites. There are several interrelated factors which can effect ionic conductivity such as defect chemistry of the solid, binding energies of the ions, concentrations of mobile ions and vacancies, size of the mobile ion and the size of interstitial bottleneck it migrates through, lattice parameter, and doping. Additionally, ion transport in polycrystalline solids such as the electrolytic perovskites of the present invention are believed to be limited by grain boundaries. These factors in relation to traditional perovskites and/or the electrolytic perovskites of the present invention are described in greater detail below.

The Interstitial Bottleneck

Figure 1A:
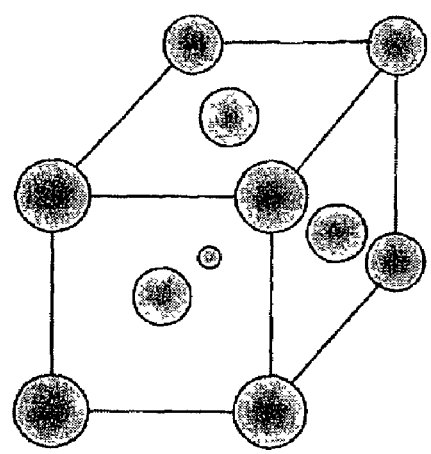
FIGS. 1A–1B (PRIOR ART) are diagrams illustrating a unit cell of a traditional perovskite of the formula $ABO_3$.
Figure 1B:
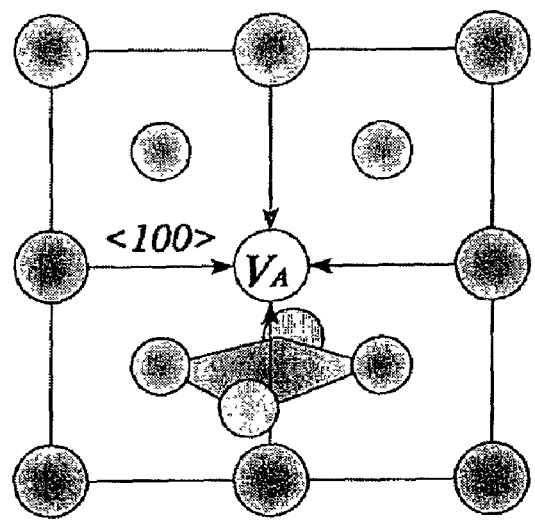

A traditional oxide perovskite has the formula $ABO_3$ and a primitive, cubic crystal structure that consists of three sublattices with $A^{m+}$ at the cube corners, $B^{(6-m)+}$ at the body center, and $O^{2-}$ at the three face-centered positions. FIG. 1A shows a picture of the traditional perovskite unit cell. In traditional perovskites, there are three sublattices on which ions can move. Ions occupying the A-sublattice are expected to jump along the <100> family of directions through a symmetric, square-shaped interstitial neck formed by four oxygen as shown by, FIG. 1B. The jump distance is approximately equal to the lattice parameter, a, and the size of the interstitial neck is $\sim a - 2r_{O^{2-}}$ where $r_{O^{2-}}$ is the radius of an oxygen ion. For many perovskites, $a \approx 4$ and $r_{O^{2-}} = 1.4$ Å which gives a neck size $\approx 1.2$ Å. A-site ions with radii ~0.6 Å that may slip through the bottleneck such as $Li^+$ and $H^+$ may be quite mobile even at room temperature and lower. Although FIGS. 1A–1B are described above with respect to traditional perovskites the same general concept holds true with the electrolytic perovskites of the present invention.

While the size of the interstitial bottleneck can have an effect on activation energy of migration, electrostatic interactions also contribute. The electrostatic interaction in an tonically conductive solid such as the electrolytic perovskites of the present invention is a function of the valences and locations of the ions themselves. These two factors can be addressed by categorizing perovskites as a function of the aggregate valence of the A-site ions, "m" The electrostatic contribution to binding energy and activation energy of migration has been calculated for ideal, cubic perovskites under the assumption of a point charge lattice. Relaxations around vacancies or during ion transport were not treated. It is predicted that for $0<m<2.2$, the binding energy of A-site ions is the smallest of the three sublattices, and the electrostatic contribution to activation energy for migration is smallest. The small binding energy also implies that vacancies and defects in general are easily accommodated on the A-sublattice. The A-sublattice is amenable to doping.

From this prediction, perovskites with B-site ions of high valence such as cerates, zirconates, niobates, titanates, tungstates, molybdates, antimonates, etc. that lead to m between 0 and 2.2 are believed to be good candidates for high $Li^+$ and $H^+$ conductivity. Thus, the general composition $E_x A'_{(z''(1-x-v)-m+x)/(z''-z')} A''_{(m-x-z'(1-x-v))/(z''-z')} B'_{(y''-6+m)/(y''-y')} B''_{(6-m-y')/(y''-y')} O_3$ was chosen to permit examination of different possible $Li^+$ conductors. As described earlier, in this composition of the electrolytic perovskites of the present invention, the aggregate valence per A-site ion, "m" was chosen to be between 0 and 2.2, and the concentrations of $Li^+$, "x", and vacancies, "v", both on the A-sublattice were chosen such that $0<x<3/4$ and $0<v<3/4$ with the stipulation that $x+v>0.32$ to ensure percolation. The other A-sublattice ions, A' and A" with the respective valences of z' and z" were selected to satisfy the condition that $z' \leq m \leq z''$ and function to form A-sublattice vacancies and increase cell volume. Typically, $Na^+$ and $K^+$ were chosen for A', and $Sr^{2+}$, $Ba^{2+}$, and $La^{3+}$ for A". The B-site ions, B' and B" were chosen with the valences y' and y", respectively, to satisfy the condition $y' \leq 6-m \leq y"$ and enlarge the lattice parameter. Typically, $B'=Zr^{4+}$, $Sn^{4+}$, $Ti^{4+}$, $Ce^{4+}$, or $Hf^{4+}$ and $B"=Nb^{5+}$ or $Ta^{5+}$. As described below, X-ray diffraction (XRD) was used to determine if specific compositions actually possessed a perovskite-like structure.

Defect Chemistry

Ion conductivity is contingent in part upon the presence of vacancies and mobile species. In pure or ideal traditional perovskites, intrinsic vacancies are formed by the Schottky reaction

$$\text{Null} \rightarrow V_A^{m'} + V_B^{(6-m)'} + 3V_O^{\cdot\cdot} \tag{1}$$

where V is a vacancy where the subscript refers to the sublattice and the superscript its charge. The law of mass action for Schottky defect is $$[V_A^{m'}][V_B^{(6-m)'}][V_O^{\cdot\cdot}]^3 = \exp(-\Delta G^\circ_{(1)}/RT) \tag{2}$$

where brackets represent vacancy concentrations, $\Delta G^\circ_{(1)}$ is the standard change in free energy for the reaction, R is the gas constant, and T is the absolute temperature. Vacancies can also be created extrinsically by aliovalent doping or impurities. For example, A-sublattice vacancies are introduced into $SrZrO_3$ by addition of $La_2O_3$ and $ZrO_2$ for B-sublattice compensation according to the reaction:

$$\tfrac{1}{3}La_2O_3 + ZrO_2 \rightarrow \tfrac{2}{3}La_{Sr}^{\cdot} + \tfrac{1}{3}V_{Sr}'' + Zr_{Zr} + 3O_O \tag{3}$$

In this situation, the law of mass action dictates that a high concentration of A-sublattice vacancies suppresses vacancy concentrations on the other two sublattices.

Figure 2:
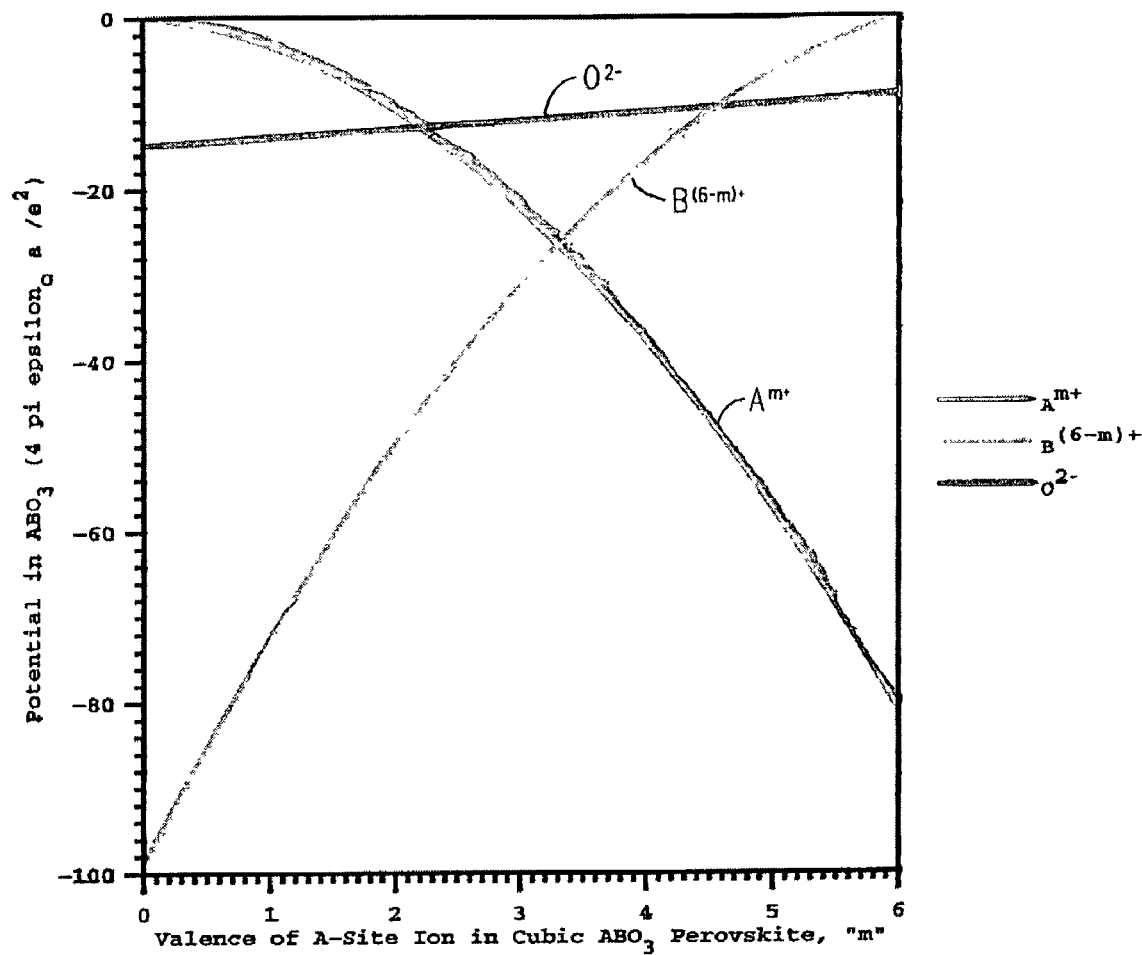
FIG. 2 (PRIOR ART) is a graph illustrating the electrostatic binding energies of $A^{m+}$, $B^{(6-m)+}$, and $O^{2-}$ as a function of the valence of A-site ions, "m", in a traditional perovskite.

The ability of a perovskite to accommodate doping and creation of vacancies can be estimated by considering ionic binding energies. A sublattice on which ions are tightly bound is less likely to accept vacancies and formation of second phases may be energetically favored. The dominant contribution to binding energies in ionic solids is electrostatic. The electrostatic binding energies of $A^{m+}$, $B^{(6-m)+}$, and $O^{2-}$ as a function of the valence of A-site ions, "m", is plotted in FIG. 2. In the calculation, the ions are treated as point charges. The calculations predict that A-site ions are weakly bound in comparison to the other ions when $m<2.2$, and the A-sublattice should easily accept large concentrations of dopants and vacancies. Again, these general concepts of the traditional perovskites hold true with the electrolytic perovskites of the present invention.

Doping Strategy

Ion mobility on the A-sublattice in electrolytic perovskites has been predicted to be high for two reasons: (1) the A-sublattice should accommodate a high degree of doping and large vacancy concentrations; and (2) interstitial bottlenecks through which ion migration occurs are relatively large. A-sublattice defected perovskites may therefore be good electrolytes. Thus, for the composition of the electrolytic perovskites of the present invention $E_x A'_{(z"(1-x-v)-m+x)/(z"-z')} A"_{(m-x-z'(1-x-v))/(z"-z')} B'_{(y"-6+m)/(y"-y')} B"_{(6-m-y')/(y"-y')} O_3$, E is selected to be a small or highly polarizable ion of valence +1 or +2 like $Li^+$, $H^+$, $Ag^+$, $Cu^+$, $Na^+$, $Mg^{2+}$ (for example). The aggregate valence per A-site ion, "m", is chosen to be in the range 0 to 2.2 so that large concentrations of mobile $E^+$ and vacancies can be placed onto the A-sublattice. To a first approximation, conductivity by a vacancy mechanism within a grain is given by the equation:

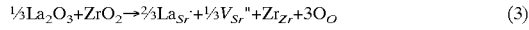

$$\sigma = kp(x+v)xv \tag{4}$$

where k is a constant and $p(x+v)$ is percolation function that needs to be greater than 0 for ion transport. For site percolation to occur on a random three-dimensional cubic lattice, $x+v$ must be greater than 0.32 otherwise $p=0$. Thus $x+v>0.32$ is a condition for all compositions of the electrolytic perovskite in the present invention. Additionally, the law of mass action given by Equation #2 ensures that vacancy concentrations on the B and O-sublattices are suppressed and implies that conductivities of B-site ions and $O^{2-}$ are very low. The other A-site ions, A' and A" are chosen based upon respective valences, z' and z", according to the condition $z' \leq m \leq z"$ to force the formation of A-sublattice vacancies, to enlarge the lattice parameter and thereby interstitial bottlenecks, and to stabilize the perovskite phase itself.

Synthesis

Figure 3:
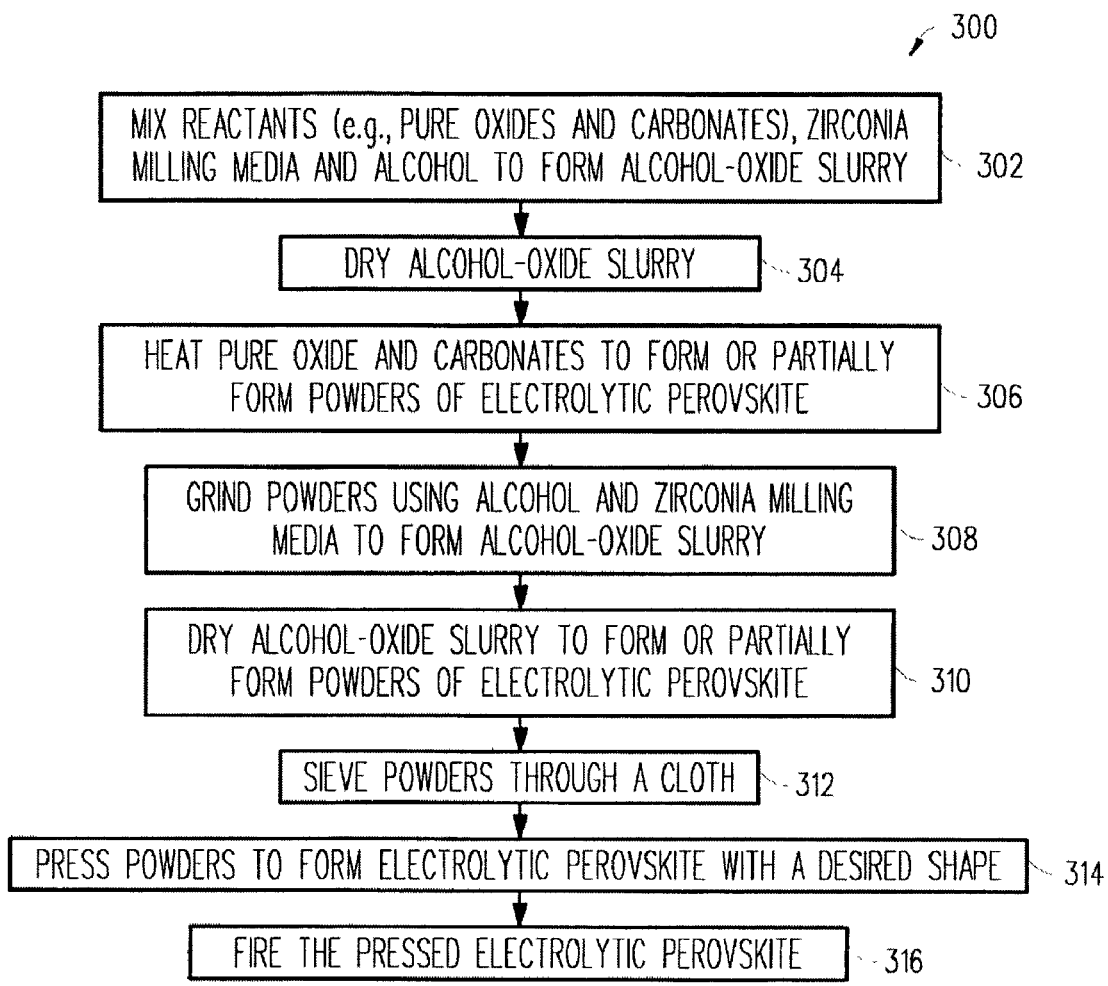
FIG. 3 is a flowchart illustrating the basic steps of a preferred method for synthesizing an electrolytic perovskite of the present invention.

Referring to FIG. 3, there is a flowchart illustrating the basic steps of a preferred method 300 for synthesizing an electrolytic perovskite of the present invention. Synthesis of candidate compositions of the electrolytic perovskite of the present invention has been performed using pure oxides and carbonates as reactants, namely $Li_2CO_3$, $Na_2CO_3$, $K_2CO_3$, $SrCO_3$, $BaCO_3$, $La_2O_3$, $CeO_2$, $ZrO_2$, $Nb_2O_5$ etc. The reactants were first wet-mixed (step 302) and ground together in Nalgene bottles using calcia stabilized zirconia media and isopropanol as the solvent. The reactant powders were added to the Nalgene bottle such that there were ~25–50 grams of powder per 250 ml of bottle volume. Zirconia milling balls with a diameter of ~1 cm were added next in the proportion ~530 grams to 250 ml of bottle volume. The bottles were filled 85–90 percent full with isopropanol and then rolled at 60 rotations per minute for ~24 hours. After 24 hours, the slurry alone was poured into a 500 ml pyrex beaker and dried (step 304) while stirring on a hot/stir plate to prevent demixing. The dried powders were heated (step 306) in a platinum crucible at temperatures ranging between 800–1100° C. for 1 to 4 hours. X-ray diffraction (XRD) was performed on the reacted materials to check for formation of perovskite-based phases.

Reacted powders were then ground (step 308) slightly with a mortar and pestle to break up any hard agglomerates, reground in the original Nalgene ball mills using the same procedure described above, and dried (step 310) while stirring on a hot plate. The obtained powders were sieved (step 312) through a 325 mesh nylon cloth, and green pills were formed by uniaxial die pressing (step 314). The die was cylindrical in shape with a diameter of 3.2 cm. The pills were sintered/fired (step 316) on platinum foil at temperatures between 1100 and 1400° C. for 2 to 8 hours. Sintered pills were then ground flat and characterized by XRD to confirm formation of desired perovskite-like phases and to check for presence of any unwanted phases such as pyrochlores and fluorites. It should be understood that this method 300 is just one of many different ways of making the electrolytic perovskite of the present invention.

It should be appreciated that other techniques can be used to make the electrolytic perovskite. Some of these techniques include mixing the A', A", B' and B" ions and then using a sol-gel process, a tape-casting process, a screen-printing process, a spray-coating process, etc. to form the electrolytic perovskite. These process can be used to produce thin, high quality membranes of electrolytic perovskite. And, the membranes of electrolytic perovskite can be used in a wide variety of applications including a fuel cell application (see below for more applications).

Li+ Conductivity Measurements

Figure 4:
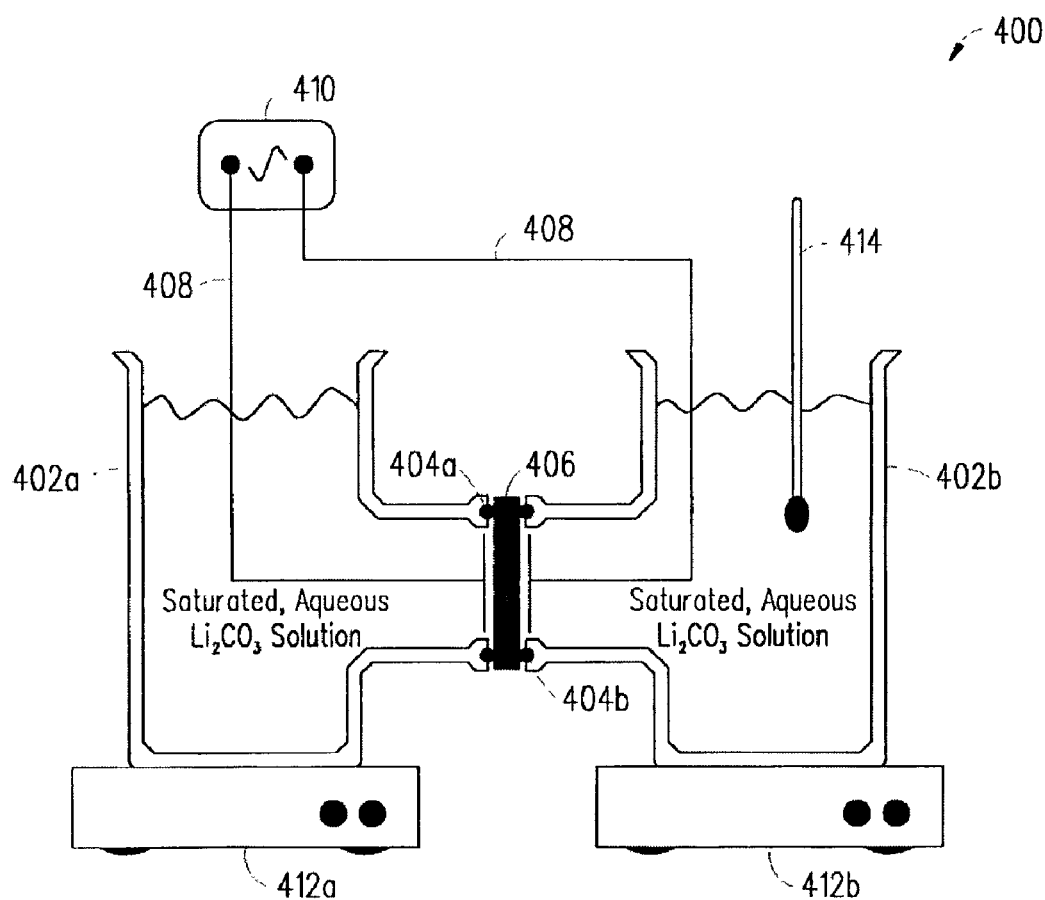
FIG. 4 is a diagram of an impedance measurement apparatus used to measure $Li^+$ conductivity of the electrolytic perovskites of the present invention.

FIG. 4 shows a diagram of an impedance measurement apparatus 400 used to measure Li+ conductivity in the electrolytic perovskites 406 of the present invention. The impedance measurement apparatus 400 includes two pyrex beakers 402a and 402b modified by the addition of rubber o-ring flanges 404a and 404b. In one experiment, the specimen 406 of the electrolytic perovskite was ground flat on both sides, it's thicknesses measured, and then it was held in place between the two beakers 402a and 404b by the rubber o-rings 404a and 404b and a flange clamp (not shown). The two beakers 402a and 402b were filled with a saturated, aqueous solution of $Li_2CO_3$. The $Li_2CO_3$ which was dissolved in water served two functions. First, it was a source and sink of rapidly moving Li+. Second, carbonate ions increased the pH of the solution so there were essentially few protons available for transport into the specimen 406. This ensured that impedance of Li+ within the specimen 406 was measured and not unwanted electrode reactions or proton transport. Platinum wires 408 were used to make electrical connection to the Impedance Analyzer 410 (e.g., HP-4192A Impedance Analyzer). Impedance was measured in the frequency range of the instrument, 5 Hz–13 MHz, at room temperature, ~20° C., and at the boiling point of the aqueous $Li_2CO_3$ solution, ~104° C. This constraint was imposed because the impedance analyzer 410 was operated manually and data was recorded by hand. As shown, hot plates 412a and 412b were used to heat the aqueous $Li_2CO_3$ solutions in the beakers 402a and 402b. And, a thermometer 414 was used to monitor the temperature of the $Li_2CO_3$ solution.

Extrusion

To demonstrate that these lithium ion conductors and proton conductors (described below) can be produced in large quantities by an industrial process such as extrusion, one composition, $Li_{1/8}K_{3/8}La_{1/4}Zr_{1/4}Nb_{3/4}O_3$, with high Li+ conductivity was selected and extruded. In the extrusion, 800 g of $Li_{1/8}K_{3/8}La_{1/4}Zr_{1/4}Nb_{3/4}O_3$ were turbula mixed for 15 minutes with 17.85 g methocell and 3.347 g sodium stearate, and water was added by mulling. Additional mixing was performed by extruding the batch through a ¼" diameter die. Ribbon, rod, and wagon-wheel tubes were extruded until all batch material was used. The ribbon die had a cross-sectional thickness of 0.05 inches, the diameter of the rod die was ¼ inch, and the wagon-wheel die was ⅜" in diameter. The extruded pieces were dried in a humidity-controlled oven for 72 hours at 98.5° C. (95% humidity). Firing was performed using slow heating rates to prevent cracking or formation of unwanted porosity during binder burnout. The firing schedule was as follows: room temperature to 600° C. in 10 hours, 600 to 800° C. in 10 hours, 800–1225° C. in 2 hours, sinter at 1225° C. for 4 hours, and cooled back to room temperature in 6 hours. Fired rods were used for mechanical properties characterization. Elastic modulus was measured using an ultrasound technique, dilatometry was used to measure thermal expansion coefficient, and modulus of rupture was measured for seven pieces in four-point-bending mode with a support span of 3.0 inches and a loading span of 0.75 inches.

Candidate Electrolytic Perovskites

Figure 5:
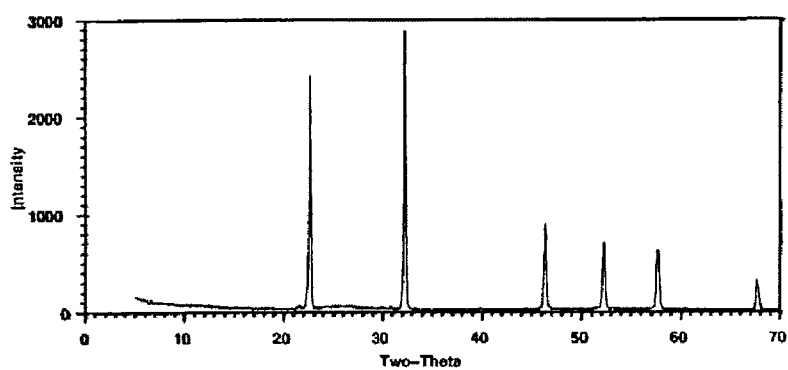
FIG. 5 is a surface XRD trace of $Li_{1/8}Na_{3/8}La_{1/6}NbO_3$ sintered at 1250° C. for 4 hours.
Figure 6A:
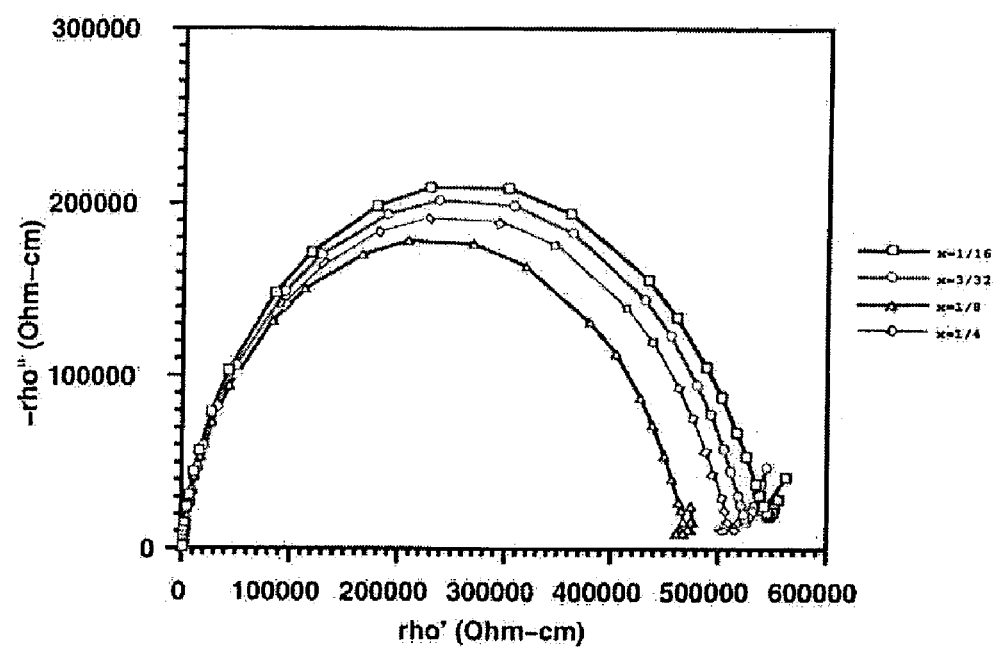
FIGS. 6A and 6B are graphs illustrating the impedance spectra for $Li_xNa_{1/2-x}La_{1/6}NbO_3$ sintered at 1325° C. for 3 hours for x=1/16, 3/32, 1/8, 1/4 measured at 20° C. and 104° C., respectively.
Figure 6B:
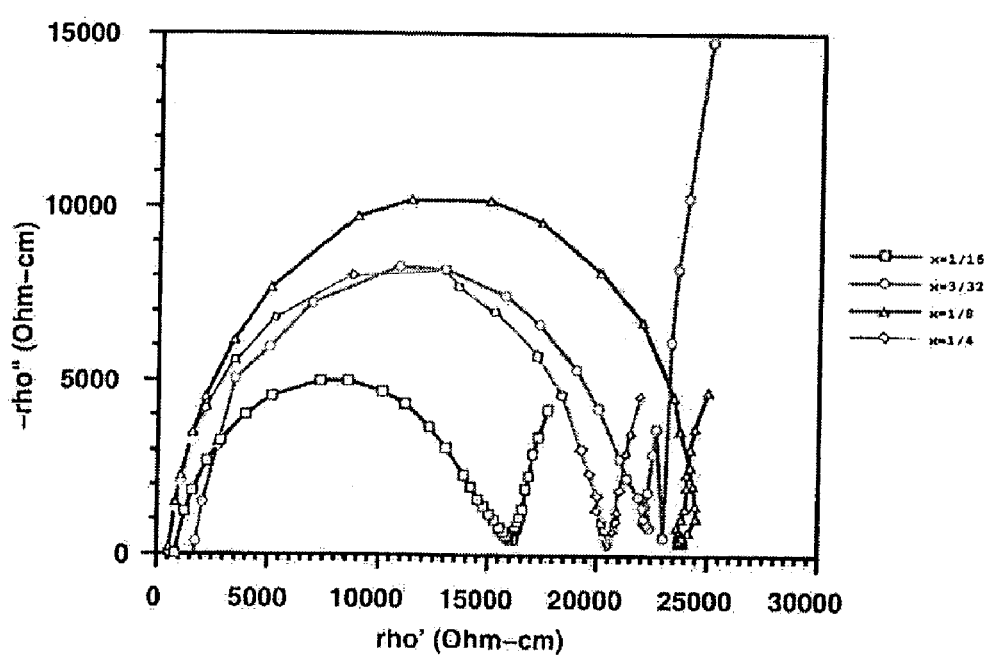

The first electrolytic perovskites studied for m=1 had the formula $Li_xNa_{(2-2x-3v)/2}La_{v/2}NbO_3$ and four specific compositions with x=1/16, 3/32, 1/8, ¼ and v=⅓ were synthesized by reacting the powders for 1 hour at 900–1000° C. XRD traces of the reacted powders showed some quantity of unreacted material and the formation of a cubic perovskite phase. In all four compositions, surface XRD of pills sintered for 2 to four hours at 1225–1325° C. were found to be single phase with primitive cubic perovskite structure. The lattice parameter was estimated to be ~3.93 Å and was nearly invariant for these compositions. Two unusual glassy halos at 2θ between 23–30 and 45–60° were also observed the XRD traces. FIG. 5 is a surface XRD trace of $Li_{1/8}Na_{3/8}La_{1/6}NbO_3$ sintered at 1250° C. for 4 hours and is typical for this family of compositions. The pills were faint yellow and semitranslucent in appearance with densities in excess of 98 percent of theoretical, 4.74 g/cm³. Li+ conductivity was observed to be relatively insensitive to changes in Li content for the same processing conditions. Further, only one semicircle was present in impedance spectra. These two facts suggest that conductivity is limited by an interface such as a grain boundary structure. FIGS. 6A and 6B are impedance plots measured at 20 and 104° C., respectively, for specimens of these four compositions sintered at 1325° C. for 3 hours. TABLE #2 is a list of the lithium ion conductivity and dielectric constants obtained by performing least squares regression to fit a semicircle to the impedance data shown in FIGS. 6A and 6B.

TABLE #2

| Material | Conductivity (S/cm) 20° | 104° C. | Activation Energy (ev) | Dielectric Constant 20° C. | 104° C. |
|---|---|---|---|---|---|
| $Li_{1/16}Na_{7/16}La_{1/6}NbO_3$ | $1.82 \times 10^{-6}$ | $6.23 \times 10^{-5}$ | 0.43 | 3251 | 4030 |
| $Li_{3/32}Na_{13/32}La_{1/6}NbO_3$ | $1.89 \times 10^{-6}$ | $4.49 \times 10^{-5}$ | 0.39 | 3081 | 2621 |
| $Li_{1/8}Na_{3/8}La_{1/6}NbO_3$ | $2.09 \times 10^{-6}$ | $4.06 \times 10^{-5}$ | 0.37 | 3575 | 3610 |
| $Li_{1/4}Na_{1/4}La_{1/6}NbO_3$ | $1.95 \times 10^{-6}$ | $4.89 \times 10^{-5}$ | 0.40 | 3296 | 3390 |

Typical conductivities were on the order of $2 \times 10^{-6}$ and $5 \times 10^{-5}$ S/cm at 20 and 104° C., respectively, with an activation energy of 0.4 eV.

Figure 7A:
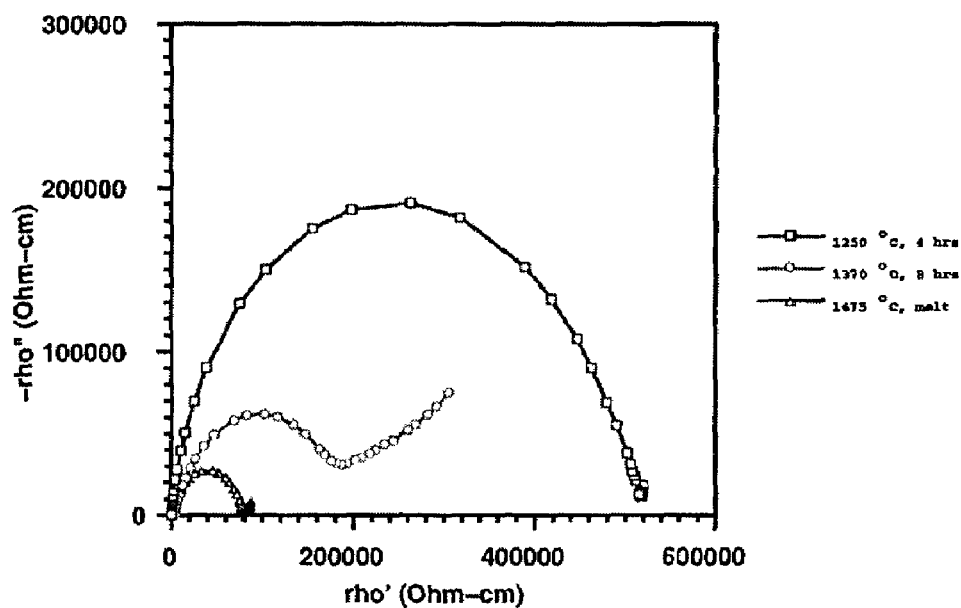
FIGS. 7A and 7B are graphs illustrating the impedance spectra for $Li_{1/8}Na_{3/8}La_{1/6}NbO_3$ sintered at various temperatures and times measured at 20° C. and 104° C., respectively.
Figure 7B:
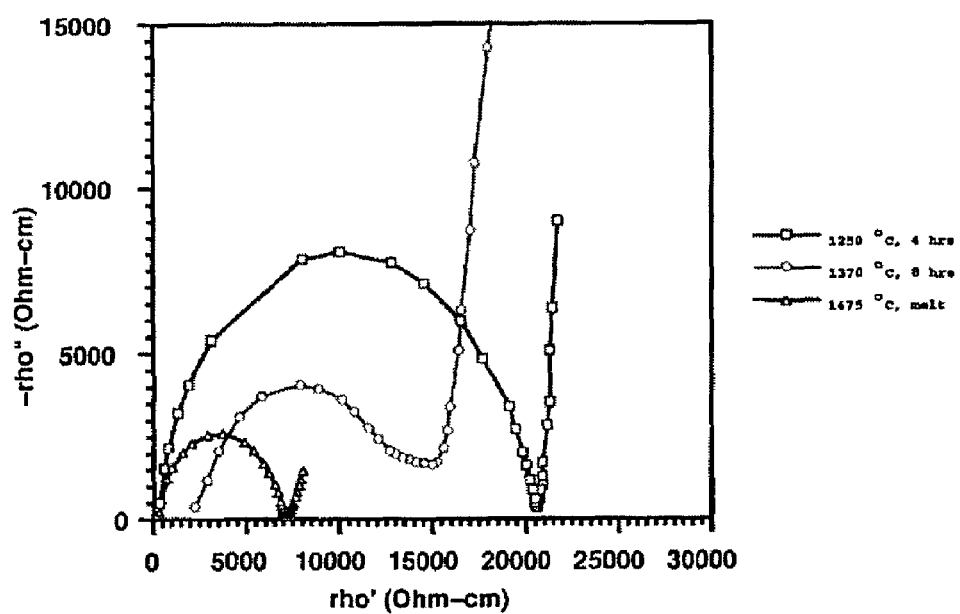

The effect of processing on conductivity was examined by varying the sintering temperature and times. It was found that the sintering temperature had a profound effect on Li+ conductivity. FIGS. 7A and 7B are impedance plots for the composition $Li_{1/8}Na_{3/8}La_{1/6}NbO_3$ for different sintering temperatures and time. In general, Li+ conductivity increased as sintering temperature and times are increased. A balance should be struck, however, between sintering temperature and time to prevent volatilization of $Na_2O$. The highest conductivity, $1.25 \times 10^{-5}$ S/cm at 20° C. and $1.4 \times 10^{-4}$ S/cm at 104° C., was obtained for melt cast materials that have grain size ~1 mm. Activation energy decreased to 0.3 eV, as well, and indicated a changing transport limitation, perhaps from interface to bulk limited.

It should be understood that the interpretation of the semicircles in impedance spectra can be a complicated undertaking. In solid-state systems, the semicircles can be attributed to three physical processes: (1) bulk ionic transport; (2) grain boundary interfaces; or (3) charge transfer reactions at electrodes. Many experiments are often necessary to discriminate between these three processes. Only one semicircle was present in the impedance plots of specimens belonging to the $Li_xNa_{(2-2x-3v)/2}La_{v/2}NbO_3$ system. Three features of the results indicate that the single semicircle is due to Li+ motion as limited by grain boundaries: (1) total conductivities were only mildly affected by Li+ concentration; (2) increased sintering temperatures and times increased Li+ conductivity because longer sintering times and higher temperatures allows grains to grow larger in size and reduce overall grain boundary interfacial area; and (3) addition of $LiNO_3$ to the saturated $Li_2CO_3$ solution did not appear to have an effect on the impedance results. It should be noted that if charge transfer resistance at an electrode was rate-limiting, then the increased Li+ concentration would have lowered the total cell impedance.

The effect of lattice parameter in this system was investigated by substitution of other large trivalent ions for lanthanum. TABLE #3 gives Li+ conductivity and lattice parameters estimated from the (110) peaks of XRD traces for specimens having the compositions $Li_{1/8}Na_{3/8}Ln_{1/6}NbO_3$ and $Li_{1/4}Na_{3/8}Ln_{1/8}NbO_3$ where Ln=Pr, Nd, Sm, Eu, Gd, and Bi all were sintered at 1250° C. for 4 hours.

TABLE #3

| | $Li_{1/8}Na_{3/8}Ln_{1/6}NbO_3$ Conductivity (S/cm) | | | $Li_{1/4}Na_{3/8}Ln_{1/8}NbO_3$ Conductivity (S/cm) | | |
|---|---|---|---|---|---|---|
| Ln | 20° C. | 104° C. | a (Å) | 20° C. | 104° C. | a (Å) |
| La | $1.94 \times 10^{-6}$ | $4.86 \times 10^{-5}$ | 3.909 | $1.00 \times 10^{-7}$ | $4.17 \times 10^{-6}$ | 3.893 |
| Pr | $1.20 \times 10^{-7}$ | $4.48 \times 10^{-6}$ | 3.899 | $1.05 \times 10^{-8}$ | $3.46 \times 10^{-7}$ | 3.879 |
| Nd | $6.84 \times 10^{-7}$ | $4.61 \times 10^{-6}$ | 3.891 | NA | NA | NA |
| Sm | $8.16 \times 10^{-9}$ | $3.62 \times 10^{-7}$ | 3.886 | $7.99 \times 10^{-9}$ | $5.68 \times 10^{-8}$ | 3.870 |
| Eu | $3.78 \times 10^{-8}$ | $1.75 \times 10^{-7}$ | 3.881 | $1.28 \times 10^{-8}$ | $4.37 \times 10^{-8}$ | 3.869 |
| Gd | $3.86 \times 10^{-8}$ | $9.04 \times 10^{-8}$ | 3.879 | $7.15 \times 10^{-9}$ | $3.73 \times 10^{-8}$ | 3.868 |
| Bi | $1.17 \times 10^{-7}$ | $4.57 \times 10^{-6}$ | 3.905 | $1.75 \times 10^{-8}$ | $2.65 \times 10^{-7}$ | 3.885 |

A trend of decreasing conductivity with decreasing lattice parameter is evident. It is believed that the size of interstitial bottlenecks at interfaces is related by overall composition to the lattice parameter of the bulk.

Figure 8:
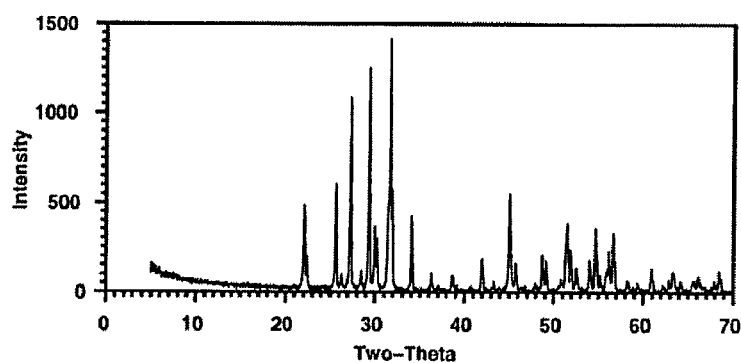
FIG. 8 is a surface XRD trace of $Li_{1/8}K_{1/2}La_{1/2}NbO_3$ sintered at 1225° C. for 4 hours.
Figure 9A:
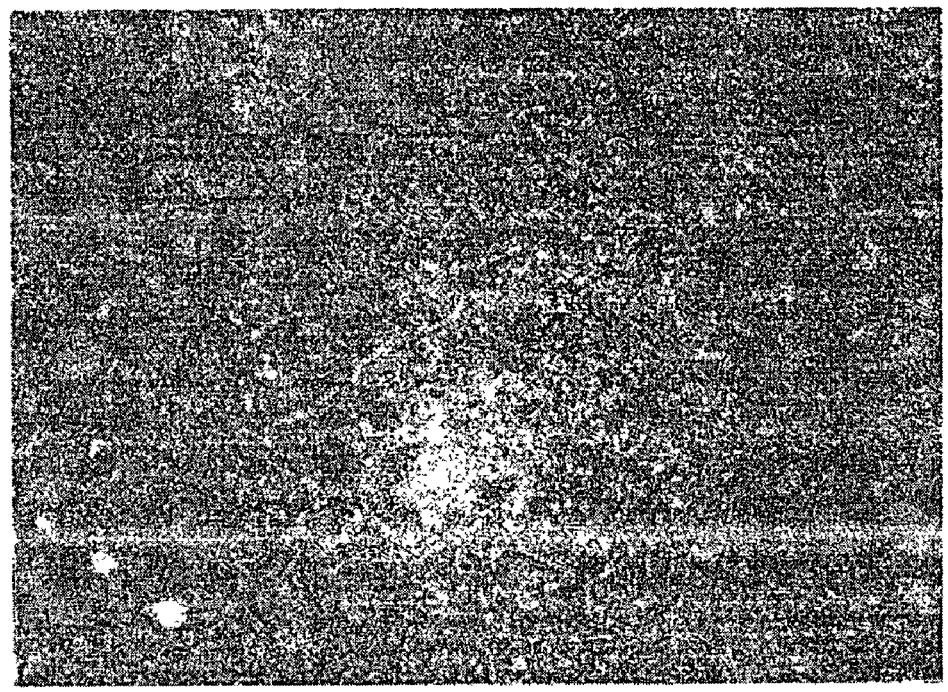
FIG. 9A is an optical micrograph of $Li_{1/8}K_{1/2}La_{1/8}NbO_3$ sintered at 1250° C. for 4 hours with a heating rate of 300° C./hour.
Figure 9B:
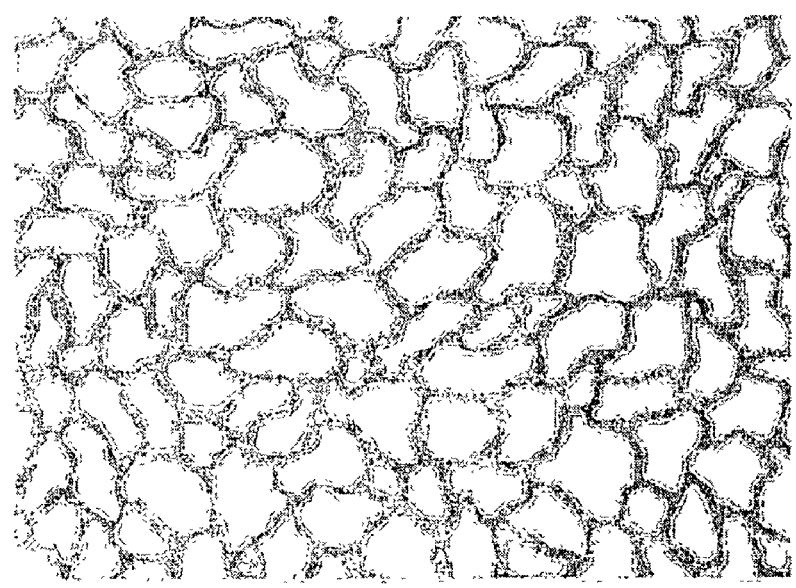
FIG. 9B is an illustration of the microstructure shown in FIG. 9A that might be obtained by sintering in a liquidous region of the phase diagram.

Several compositions of electrolytic perovskites in the $Li_xK_{(2-2x-3v)/2}La_{v/2}NbO_3$ system were studied, however, synthesis was more difficult than for the analogous sodium system described above. FIG. 8 is a surface XRD trace of a pill sintered at 1225° C. for 4 hours. The structure was found to be perovskite-like with a large, nonprimitive unit-cell based upon the tetragonal $K_2LaNb_5O_{15}$ structure. Sintering was complicated by evaporation of $K_2O$ and densification was hindered due to growth of needle-shaped grains. Pills sintered at 1300° C. and higher were porous and not necessarily fit for conductivity measurements. It was found that most compositions in this family which contain Li, densify to an impervious state (>95% theoretical) at sintering temperatures below ~1250° C. There was also evidence of liquid phase formation during the sintering process because: (1) pills were observed to expand as sintering temperature was increased which is consistent with formation of a liquid with a greater molar volume that the corresponding solid; and (2) optical micrographs of polished specimens showed small grains embedded within a matrix phase. XRD verified that only one phase is present, and the matrix phase likely forms during solidification of the liquid upon cooling. FIG. 9A is an optical micrograph of $Li_{1/8}K_{1/2}La_{1/8}NbO_3$ sintered at 1250° C. for 4 hours with a heating rate of 300° C./hour. The specimen was polished to 0.25 μm and thermally etched at 1000° C. to make the microstructure visible. It should be noticed that the grains are surrounded by another phase (see FIG. 9B). Average grain size is estimated to be 2 μm and the porosity is fully closed.

Figure 10A:
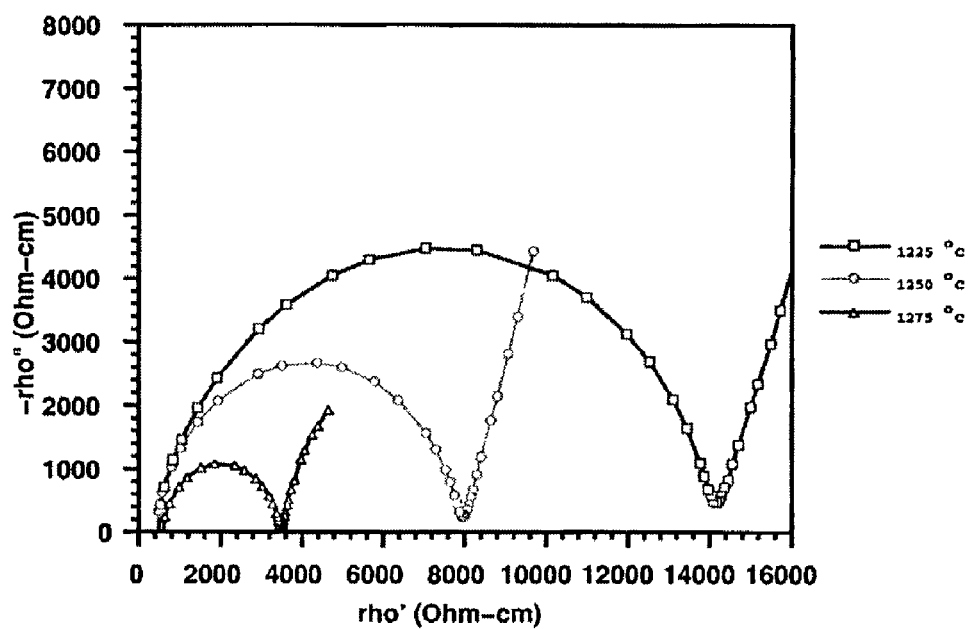
FIGS. 10A and 10B are graphs illustrating the impedance spectra measured at 20 and 104° C., respectively, for $Li_{1/8}K_{1/2}La_{1/8}NbO_3$ sintered for 4 hours at temperatures of 1225, 1250, and 1275° C.
Figure 10B:
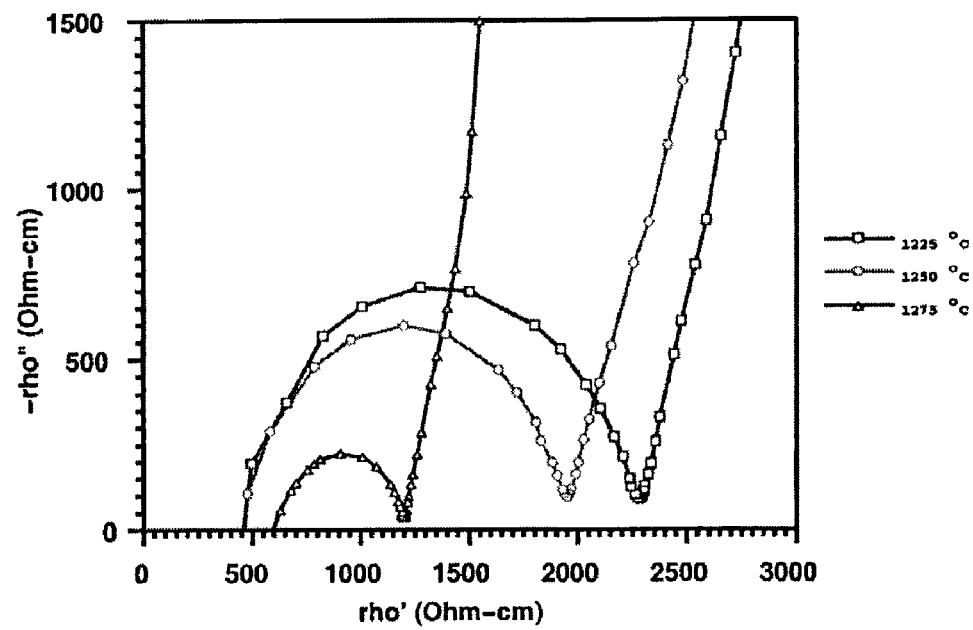

The highest lithium ion conductivities in these experiments were obtained for specimens of the composition $Li_{1/8}K_{1/2}La_{1/8}NbO_3$. Once again, sintering temperature was observed to have a dramatic effect on conductivities. FIGS. 10A and 10B are impedance spectra measured at 20 and 104° C., respectively, for $Li_{1/8}K_{1/2}La_{1/8}NbO_3$ sintered for 4 hours at temperatures of 1225, 1250, and 1275° C. In the plots, the rightmost intersections of the semicircles with the real axis correspond approximately to resistivity (reciprocal of conductivity). TABLE #4 summarizes the results obtained by analyzing the impedance spectra shown in FIGS. 10A and 10B. Li+ conductivity, dielectric constant, and activation energy for conduction of $Li_{1/8}K_{1/2}La_{1/8}NbO_3$ sintered for 4 hours a various temperatures.

TABLE #4

| Sintering Temperature | Conductivity (S/cm) | | Activation Energy (eV) | Dielectric Constant | |
|---|---|---|---|---|---|
| | 20° C. | 104° C. | | 20° C. | 104° C. |
| 1225 | $6.96 \times 10^{-5}$ | $4.36 \times 10^{-4}$ | 0.24 | 16,951 | 10,235 |
| 1250 | $1.25 \times 10^{-4}$ | $5.10 \times 10^{-4}$ | 0.19 | 12,205 | 10,944 |
| 1275 | $2.86 \times 10^{-4}$ | $8.22 \times 10^{-4}$ | 0.15 | 10,023 | 12,949 |

The trend is clear, as sintering temperature was increased the conductivity increased. It is believed that the higher Li+ conductivities in this system as compared those in the analogous sodium containing system are the result of: (1) larger interstitial bottle necks in the bulk and at the interfaces; and (2) interfacial differences resulting from formation of a liquid phase during sintering. The increased interstitial bottleneck size was evident in the reduced activation energy for conduction of 0.2 versus 0.4 eV for $Li_{1/8}Na_{3/8}La_{1/6}NbO_3$.

Solid-state LI-NMR was used to examine the nature of the Li+ environment within $Li_{1/8}K_{1/2}La_{1/8}NbO_3$ in the temperature range −150 to 250° C. at intervals of 25° C. Not surprisingly, signal due to relaxation of Li+ could be detected without use of magic angle spinning, nonetheless, spinning at 4 kHz was used to enhance resolution. Two Li+ environments were identified, although the difference is slight The result is consistent with the nonprimitive, tetragonal structure of $K_2LaNb_5O_{15}$. The relaxation time, $T_1$, was found to be nearly insensitive to temperature over the entire range, and Li+ was still highly mobile even at temperatures as low as −150° C. The activation energy of relaxation was found to be 0.01 eV which differs dramatically from the value of 0.2 eV obtained by impedance spectroscopy. Despite that there is seldom a one-to-one correspondence between activation energies measured by NMR and impedance spectroscopy, this difference is quite large. The usual explanation is that NMR detects Li+ motion in the bulk since the magnetic excitation occurs throughout the entire specimen, whereas impedance spectroscopy may be detecting Li+ motion as limited by grain boundary interfaces.

Given the high lithium ion conductivity of $Li_{1/8}K_{1/2}La_{1/8}NbO_3$, concentrations of lithium and A-sublattice vacancies of x=⅛ and v=¼, respectively, were used as starting points when investigating other compositions that conform to the general formula $LiA'_{(z''(1-x-v)-m+x)/(z''-z')} A''_{(m-x-z'(1-x-v))/(z''-z')} B'_{(y''-6+m)/(y''-y')} B''_{(6-m-y')/(y''-y')} O_3$ Creation of A-sublattice vacancies using the large, alkaline earth ions $Ba^{2+}$ and $Sr^{2+}$ in addition to $La^{3+}$ was explored for aggregate valences of the A-sublattice of 1.0, 1.125, and 1.25. Increase of the aggregate valence of the A-sublattice was obtained by addition of $Zr^{4+}$ to the B-sublattice. In terms of the general compositional formula, $A'=Na^+$ or $K^+$, $A''=Sr^{2+}$, $Ba^{2+}$, or $La^{3+}$, $B'=Zr^{4+}$, and $B''=Nb^{5+}$. TABLE #5 is a list of each composition obtained for this combination of dopants, as well as for some of the compositions described previously, along with estimates of the unit cell dimensions.

As in the case of $Li_{1/8}Na_{3/8}Ln_{1/6}NbO_3$, there does not appear to be a correlation between lattice parameter and $Li^+$ conductivity through bottleneck size.

Figure 11A:
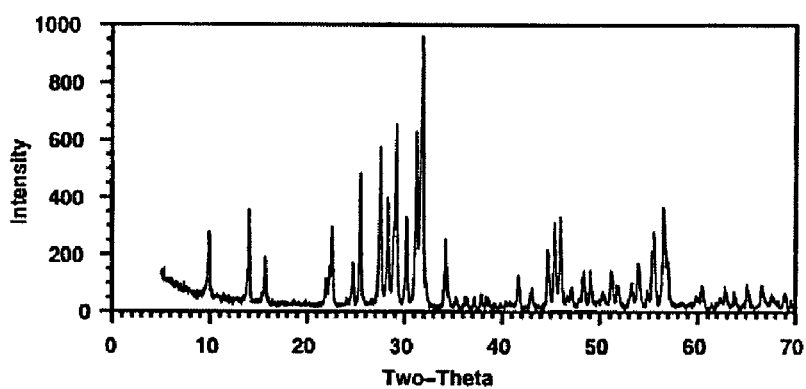
FIGS. 11A–11C are graphs of surface XRD traces of $Li_{1/8}K_{3/8}La_{1/4}Zr_{1/4}Nb_{3/4}O_3$, $Li_{1/8}K_{3/8}Ba_{1/4}NbO_3$, and $Li_{1/8}Na_{3/8}La_{1/4}Zr_{1/4}Nb_{3/4}O_3$ sintered at 1250° C. for 4 hours, respectively.
Figure 11B:
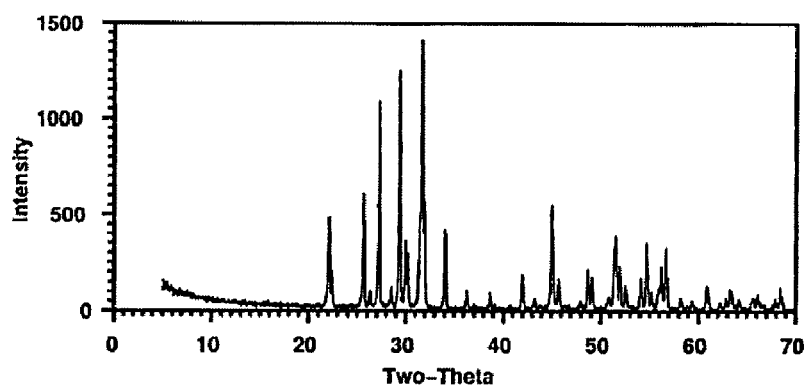
Figure 11C:
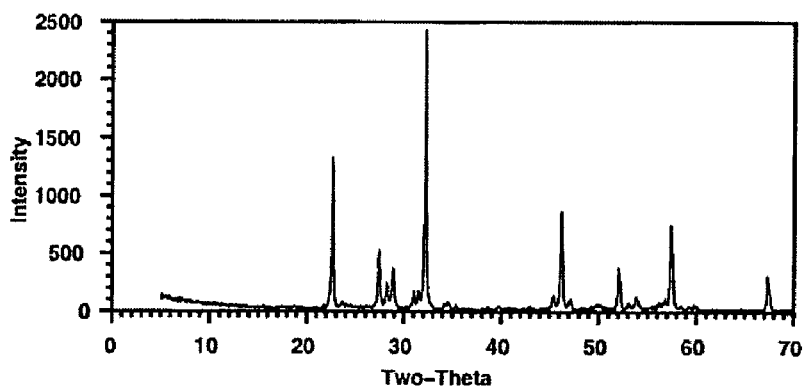

The four compositions with the highest room temperature $Li^+$ conductivities in descending order were $Li_{1/8}K_{3/8}La_{1/4}Zr_{1/4}Nb_{3/4}O_3$, $Li_{1/8}K_{3/8}Ba_{1/4}NbO_3$, $Li_{1/8}K_{1/2}La_{1/8}NbO_3$, and $Li_{1/8}Na_{3/8}La_{1/4}Zr_{1/4}Nb_{3/4}O_3$ (see TABLE #6). FIGS. 11A–11C are surface XRD traces of pills of the three newly

TABLE #5

| m | A' | z' | A'' | z'' | B' | y' | B'' | y'' | x | v | Composition | ā |
|---|----|----|-----|-----|----|----|-----|-----|---|---|-------------|---|
| 1 | K | 1 | Ba | 2 | Nb | 5 | Nb | 5 | 1/8 | 1/4 | $Li_{1/8}K_{3/8}Ba_{1/4}NbO_3$ | 3.955 |
| 1 | K | 1 | La | 3 | Nb | 5 | Nb | 5 | 1/8 | 1/4 | $Li_{1/8}K_{1/2}La_{1/8}NbO_3$ | 3.954 |
| 1 | K | 1 | La | 3 | Nb | 5 | Nb | 5 | 17/80 | 18/40 | $Li_{17/80}K_{36/80}La_{9/80}NbO_3$ | 3.935 |
| 1 | K | 1 | Sr | 2 | Nb | 5 | Nb | 5 | 1/8 | 1/4 | $Li_{1/8}K_{3/8}Sr_{1/4}NbO_3$ | 3.927 |
| 1 | K | 1 | La | 3 | Nb | 5 | Nb | 5 | 1/4 | 1/4 | $Li_{1/4}K_{3/8}La_{1/8}NbO_3$ | 3.922 |
| 1 | Na | 1 | Ba | 2 | Nb | 5 | Nb | 5 | 1/8 | 1/4 | $Li_{1/8}Na_{3/8}Ba_{1/4}NbO_3$ | 3.914 |
| 1 | Na | 1 | La | 3 | Nb | 5 | Nb | 5 | 1/8 | 2/5 | $Li_{1/8}Na_{11/40}La_{1/5}NbO_3$ | 3.906 |
| 1 | Na | 1 | La | 3 | Nb | 5 | Nb | 5 | 1/8 | 1/3 | $Li_{1/8}Na_{3/8}La_{1/6}NbO_3$ | 3.903 |
| 1 | Na | 1 | Sr | 2 | Nb | 5 | Nb | 5 | 1/8 | 1/4 | $Li_{1/8}Na_{3/8}Sr_{1/4}NbO_3$ | 3.885 |
| 1.125 | K | 1 | Ba | 2 | Zr | 4 | Nb | 5 | 1/8 | 1/4 | $Li_{1/8}K_{1/4}Ba_{3/8}Zr_{1/8}Nb_{7/8}O_3$ | 3.978 |
| 1.125 | K | 1 | La | 3 | Zr | 4 | Nb | 5 | 1/8 | 1/4 | $Li_{1/8}K_{7/16}La_{3/16}Zr_{1/8}Nb_{7/8}O_3$ | 3.972 |
| 1.125 | Na | 1 | Ba | 2 | Zr | 4 | Nb | 5 | 1/8 | 1/4 | $Li_{1/8}Na_{1/4}Ba_{3/8}Zr_{1/8}Nb_{7/8}O_3$ | 3.950 |
| 1.125 | K | 1 | Sr | 2 | Zr | 4 | Nb | 5 | 1/8 | 1/4 | $Li_{1/8}K_{1/4}Sr_{3/8}Zr_{1/8}Nb_{7/8}O_3$ | 3.940 |
| 1.125 | Na | 1 | La | 3 | Zr | 4 | Nb | 5 | 1/8 | 1/4 | $Li_{1/8}Na_{7/16}La_{3/16}Zr_{1/8}Nb_{7/8}O_3$ | 3.923 |
| 1.125 | Na | 1 | Sr | 2 | Zr | 4 | Nb | 5 | 1/8 | 1/4 | $Li_{1/8}Na_{1/4}Sr_{3/8}Zr_{1/8}Nb_{7/8}O_3$ | 3.912 |
| 1.25 | K | 1 | Ba | 2 | Zr | 4 | Nb | 5 | 1/8 | 1/4 | $Li_{1/8}K_{1/8}Ba_{1/2}Zr_{1/4}Nb_{3/4}O_3$ | 4.000 |
| 1.25 | K | 1 | La | 3 | Zr | 4 | Nb | 5 | 1/8 | 1/4 | $Li_{1/8}K_{3/8}La_{1/4}Zr_{1/4}Nb_{3/4}O_3$ | 3.990 |
| 1.25 | Na | 1 | Ba | 2 | Zr | 4 | Nb | 5 | 1/8 | 1/4 | $Li_{1/8}Na_{1/8}Ba_{1/2}Zr_{1/4}Nb_{3/4}O_3$ | 3.986 |
| 1.25 | Na | 1 | Sr | 2 | Zr | 4 | Nb | 5 | 1/8 | 1/4 | $Li_{1/8}Na_{1/8}Sr_{1/2}Zr_{1/4}Nb_{3/4}O_3$ | 3.968 |
| 1.25 | K | 1 | Sr | 2 | Zr | 4 | Nb | 5 | 1/8 | 1/4 | $Li_{1/8}K_{1/8}Sr_{1/2}Zr_{1/4}Nb_{3/4}O_3$ | 3.954 |
| 1.25 | Na | 1 | La | 3 | Zr | 4 | Nb | 5 | 1/8 | 1/4 | $Li_{1/8}Na_{3/8}La_{1/4}Zr_{1/4}Nb_{3/4}O_3$ | 3.948 |

Estimation of the unit cell dimensions was made by a rules of mixture calculation using the volume per primitive perovskite cell of the relevant end members. Inspection of the list shows that aggregate valence of the A-sublattice or alternatively $Zr^{4+}$ content has a large effect on unit cell volume. Synthesis of each composition listed in TABLE #5 was attempted for $Li^+$ conductivity measurement, and XRD was used to check for formation of second phases. TABLE #6 list various composition electrolytic perovskites including their room temperature $Li^+$ conductivity, 4 hour sintering temperature, parent structure type, and presence and type of any second phases.

identified compositions sintered at 1250° C. for 4 hours. $Li_{1/8}K_{1/2}La_{1/8}NbO_3$ has already been discussed. It should be noted that $Li_{1/8}K_{3/8}Ba_{1/4}NbO_3$ was the only alkaline earth doped composition found to have usefully high conductivity, but it decomposed rapidly on contact with water and fell apart. The rapid rate of decomposition and resulting gritty residue indicate that the attack by water was likely intergranular. The optimum sintering temperature was observed to be ~1200° C.

The compositions $Li_{1/8}K_{3/8}La_{1/4}Zr_{1/4}Nb_{3/4}O_3$ and $Li_{1/8}Na_{3/8}La_{1/4}Zr_{1/4}Nb_{3/4}O_3$ differ only by the type of alkaline ion placed on the A-sublattice, potassium or sodium. Surface

TABLE #6

| Composition | Lattice Parameter (Å) | Base Structure | Conductivity of $Li^+$ (S/cm) | Sintering Temperature (° C.) | Second Phase |
|---|---|---|---|---|---|
| $Li_{1/8}K_{3/8}Ba_{1/4}NbO_3$ | 4 011 | $KBa_2NbO_5O_{15}$ | $2\,00 \times 10^{-4}$ | 1200 | No |
| $Li_{1/8}K_{1/2}La_{1/8}NbO_3$ | 3 940 | $K_2LaNbO_5O_{15}$ | $1\,25 \times 10^{-4}$ | 1250 | No |
| $Li_{1/8}K_{3/8}Sr_{1/4}NbO_3$ | 3 967 | $KSr_2Nb_5O_{15}$ | $8\,91 \times 10^{-8}$ | 1250 | No |
| $Li_{1/8}Na_{3/8}Ba_{1/4}NbO_3$ | 3 931 | $NaBa_2Nb_5O_{15}$ | $6\,61 \times 10^{-5}$ | 1250 | No |
| $Li_{1/8}Na_{13/40}La_{1/5}NbO_3$ | 3 918 | Cubic | $8.35 \times 10^{-6}$ | 1250 | No |
| $Li_{1/8}Na_{3/8}Sr_{1/4}NbO_3$ | 3 934 | Cubic | $6\,51 \times 10^{-6}$ | 1250 | No |
| $Li_{1/8}K_{1/4}Ba_{3/8}Zr_{1/8}Nb_{7/8}O_3$ | 4 013 | $KBa_2Nb_5O_{15}$ | Small | 1250 | No |
| $Li_{1/8}K_{7/6}La_{3/16}Zr_{1/8}Nb_{7/8}O_3$ | 3 945 | $K_2LaNb_5O_{15}$ | Porous | 1250–1300 | $ZrO_2/LaNbO_4$ |
| $Li_{1/8}Na_{1/4}Ba_{3/8}Zr_{1/8}Nb_{7/8}O_3$ | Lost | | | | |
| $Li_{1/8}K_{1/4}Sr_{3/8}Zr_{1/8}Nb_{7/8}O_3$ | 3.993 | $KSr_2Nb_5O_{15}$ | $1\,80 \times 10^{-7}$ | 1300 | No |
| $Li_{1/8}Na_{7/16}La_{3/16}Zr_{1/8}Nb_{7/8}O_3$ | 3 928 | Cubic | $3\,37 \times 10^{-7}$ | 1250 | No |
| $Li_{1/8}Na_{1/4}Sr_{3/8}Zr_{1/8}Nb_{7/8}O_3$ | 3 972 | Cubic | $2\,73 \times 10^{-5}$ | 1250 | No |
| $Li_{1/8}K_{1/8}Ba_{1/2}Zr_{1/4}Nb_{3/4}O_3$ | 4 022 | $KBa_2Nb_5O_{15}$ | $2\,49 \times 10^{-7}$ | 1300 | No |
| $Li_{1/8}K_{3/8}La_{1/4}Zr_{1/4}Nb_{3/4}O_3$ | 4 004 | $K_2LaNb_5O_{15}$ | $2\,22 \times 10^{-4}$ | 1250 | $ZrO_2/LaNbO_4$ |
| $Li_{1/8}Na_{1/8}Ba_{1/2}Zr_{1/4}Nb_{3/4}O_3$ | 4 002 | Cubic | $4\,82 \times 10^{-6}$ | 1250 | No |
| $Li_{1/8}Na_{1/8}Sr_{1/2}Zr_{1/4}Nb_{3/4}O_3$ | 3 997 | $NaSr_2Nb_5O_{15}$ | Large | 1300 | No |
| $Li_{1/8}K_{1/8}Sr_{1/2}Zr_{1/4}Nb_{3/4}O_3$ | 3 977 | $KSr_2Nb_5O_{15}$ | $1\,08 \times 10^{-5}$ | 1275 | No |
| $Li_{1/8}Na_{3/8}La_{1/4}Zr_{1/4}Nb_3$ | 3 932 | Cubic | $9\,00 \times 10^{-5}$ | 1250 | $ZrO_2/LaNbO_4$ |

Figure 12:
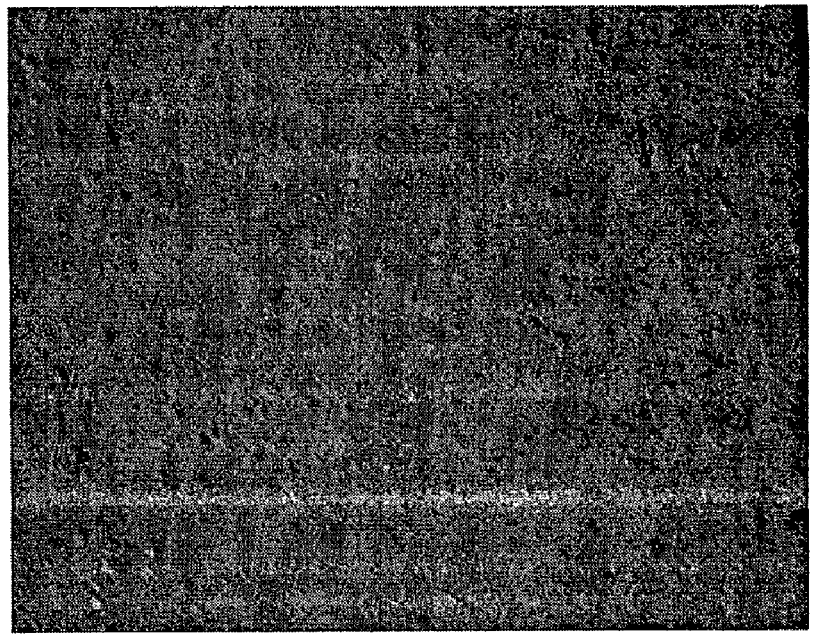
FIG. 12 is a 500× optical micrograph of a polished $Li_{1/8}K_{3/8}La_{1/4}Zr_{1/4}Nb_{3/4}O_3$ sintered at 1250° C. for 4 hours where the dual interference contrast reveals second phase particles of $LaNbO_4$ and $m-ZrO_2$ as regions with raised surface relief.
Figure 13:
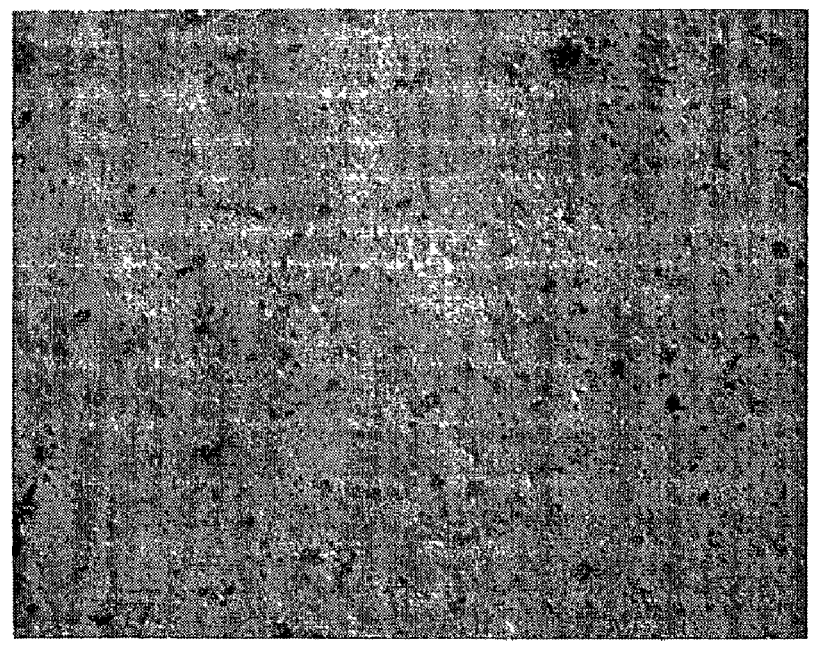
FIG. 13 is a 500× optical micrograph of a polished $Li_{1/8}Na_{3/8}La_{1/4}Zr_{1/4}Nb_{3/4}O_3$ sintered at 1250° C. for 1 hour where the dual interference contrast reveals second phase particles of $LaNbO_4$ and $m-ZrO_2$ as regions with raised surface relief.

XRD traces of pills showed the presence of ~20 volume percent of second phase $LaNbO_4$ and monoclinic $ZrO_2$ in both cases. The second phases could be seen using an optical microscope with dual interference contrast. FIGS. 12 and 13 are optical micrographs of $Li_{1/8}K_{3/8}La_{1/4}Zr_{1/4}Nb_{3/4}O_3$ and $Li_{1/8}Na_{3/8}La_{1/4}Zr_{1/4}Nb_{3/4}O_3$, respectively, sintered at 1250° C. The second phases appear as regions of raised contrast. The precise compositions of the second phases were ascertained by electron microprobe analysis of polished pill of $Li_{1/8}Na_{3/8}La_{1/4}Zr_{1/4}Nb_{3/4}O_3$ sintered at 1250° C. for 4 hours. The $LaNbO_3$ was slightly La-rich, and no other species were dissolved in either second phase.

Figure 14:
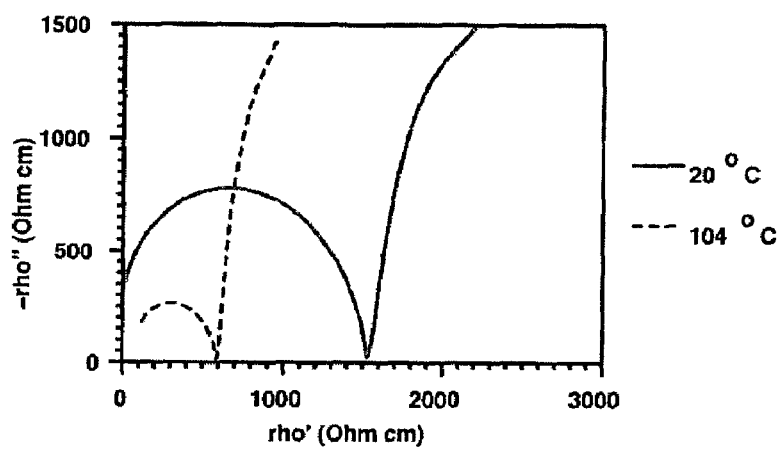
FIG. 14 is a graph illustrating the impedance spectra for $Li_{1/8}K_{3/8}La_{1/4}Zr_{1/4}Nb_{3/4}O_3$ sintered at 1200° C. for 1 hour measured at 20 and 104° C.
Figure 15:
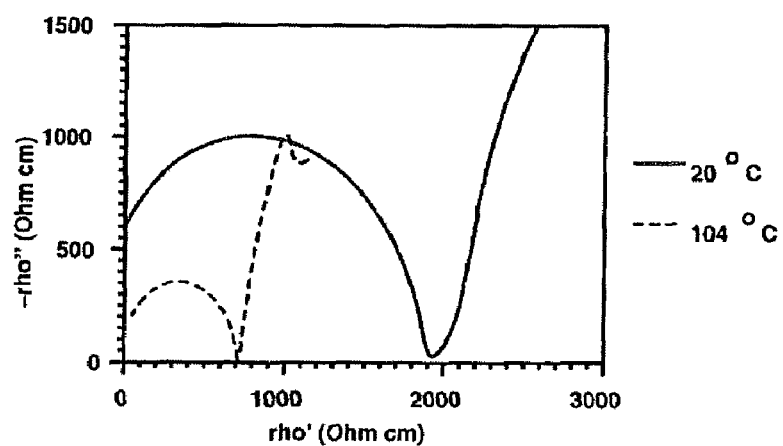
FIG. 15 is a graph illustrating the impedance spectra for $Li_{1/8}Na_{3/8}La_{1/4}Zr_{1/4}Nb_{3/4}O_3$ sintered at 1275° C. for 1 hour measured at 20 and 104° C.

Plots of imaginary versus the real components of impedance for $Li_{1/8}K_{3/8}La_{1/4}Zr_{1/4}Nb_{3/4}O_3$ and $Li_{1/8}Na_{3/8}La_{1/4}Zr_{1/4}Nb_{3/4}O_3$ showed a single semicircle. The effect of sintering temperature and time on $Li^+$ conductivity was examined to determine if grain boundary resistance dominates ion conduction. The $Li^+$ conductivity of $Li_{1/8}Na_{3/8}La_{1/4}Zr_{1/4}Nb_{3/4}O_3$ sintered at 1250° C. for 4 hours, 1300° C. for 4 hours, and 1200° C. for 4 hours followed by 1275° C. for an additional 4 hours were measured to be $9.00 \times 10^{-5}$, $8.49 \times 10^{-5}$, and $9.45 \times 10^{-5}$ S/cm, respectively. Conductivity varied by no more than 10 percent. In order to distinguish between bulk conduction and charge transfer resistance, the saturated $Li_2CO_3$ solution used in impedance measurements was replaced by solution of 150 g $LiNO_3+5$ g $Li_2CO_3$ per liter $H_2O$. Such a dramatic change in $Li^+$ concentration would have an easily measured effect on impedance if charge transfer were limiting. FIGS. 14 and 15 are plots of imaginary versus real components of impedance for $Li_{1/8}K_{3/8}La_{1/4}Zr_{1/4}Nb_{3/4}O_3$ sintered at 1225° C. for 4 hours and $Li_{1/8}Na_{3/8}La_{1/4}Zr_{1/4}Nb_{3/4}O_3$ sintered at 1275° C. for 1 hour, respectively, measured at 20 and 104° C. using the $LiNO_3$ containing solution. The $Li^+$ conductivities were significantly higher in comparison to results obtained using the saturated $Li_2CO_3$ solution. Further increases in $LiNO_3$ concentration did not appear to lead to additional increases in apparent conductivity. The semicircle in the impedance plots has been determined to originate from either bulk or grain boundary transport. Activation energies for conduction as determined using only measurements at these two temperatures were determined to be 0.137 and 0.140 eV, respectively.

Extrusion using the EX-22 batch recipe as described above was not possible in these experiments. The batch recipe called for the addition of 140 ml of $H_2O$ during mulling. The resultant batch was dry to the touch and sheared only with great difficulty. The batch would not extrude through any die, was removed from the extruder, and chopped into small pieces for a second mulling to add more water. An additional 35 ml of $H_2O$ was added, but the batch remained difficult to shear. The remulled material was successfully extruded through the spaghetti die, but flow of the extrudate was jerky. Nevertheless, pieces of rods, wagon wheel, and ribbon were obtained without cracks. Fired pieces were semitranslucent and similar in color to pills fabricated by die pressing of dry powders. No discoloration due to abrasion of metal from the extrusion die was observed. Shrinkage through the thickness was –28 percent. Sintered rods were used for mechanical properties measurement. Elastic modulus was measured according to the ASTM C623 standard to be 9.07 GPa ($1.29 \times 10^7$ psi). Thermal expansion coefficient as measured by dilatometry was found to be $10 \times 10^{-6}$/K. The mean modulus of rupture from test of seven rods with diameters of 0.27 inches was 25 MPa (3621 psi). Lithium ion conductivity was measured using fired pieces of ribbon and was found to be comparable to that obtained from die pressed pills, and powder XRD showed the presence of the expected phases in same proportion as in die pressed pills. It must be noted that second phase m-$ZrO_2$ and $LaNbO_4$ undoubtedly affected these mechanical properties. Second phases are also discussed below in the Niobate Perovskites section below.

Proton Conductors (Exchange Protons for $Li^+$ in Perovskites)

It has been shown that it is possible to exchange protons for $Li^+$ in an electrolytic perovskite to create a solid proton conductor for operation at temperatures between 20–300° C. Proton exchange can be conducted in one of two ways: (1) active electrochemical pumping; and (2) passive immersion in an appropriate source of protons. Three compositions, $Li_{1/8}K_{3/8}La_{1/4}Zr_{1/4}Nb_{3/4}O_3$, $Li_{1/8}Na_{3/8}La_{1/4}Zr_{1/4}Nb_{3/4}O_3$, and $Li_{1/8}K_{1/2}La_{1/8}NbO_{3/4}O_3$, for proton exchange. It should be understood that other compositions of electrolytic perovskites may be used to make proton conductors (see, e.g., TABLES #2 and #6).

Active exchange by electrochemical pumping to date has been partially successful. Ionic current increased as a function of time as more and more $Li^+$ was replaced by $H^+$. Unfortunately, every specimen in these experiments cracked at some point during the exchange process. A single crack formed at the outer edge of the disks and propagated toward the center. The explanation of cracking is a volumetric change of the structure associated with replacement of $Li^+$ by $H^+$. These electrolytic compositions expand on exchange of $Li^+$ for $H^+$ as verified by XRD. The outer edge of the disks where the crack initially formed was obscured from the acid solution by the rubber o-rings and was not subject to active exchange (see FIG. 4). Expansion of the center region of the disk leads to a growing tensile stress at the edge, and at some point, that tensile stress becomes so large that the disk cracks.

Passive proton exchange is believed to be superior to the active process since all that is required is immersion in a proton containing solution such as nitric acid or phosphoric acid. The passive process easily handles irregular shapes, and mixed ionic-electronic conductors can be treated. Further, the entire exterior surface is exposed to the proton containing solution, and expansion due to initial exchange at the outer surface results in a mechanical tempering effect. A key factor in judging the utility of passive proton exchange is rate. The passive process is diffusional in nature and the slowest moving species, either $Li^+$ or $H^+$, will be rate-limiting provided that exchange is thermodynamically favorable in the first place. Assuming favorable energetics, the depth of penetration by diffusion is given by Equation # 5:

$$x = \sqrt{6Dt} \tag{5}$$

where D is the diffusion coefficient and t is time. TABLE #8 lists times required to passively exchange to the given depths for limiting conductivities of 0.0001, 0.001, and 0.01 S/cm.

TABLE #8

| | Time | | |
|---|---|---|---|
| Depth | $10^{-4}$ S/cm | $10^{-3}$ S/cm | $10^{-2}$ S/cm |
| 10 μm | 8.7 min | 52 sec | 5.2 sec |
| 25 μm | 54 min | 5.4 min | 32 sec |
| 0.1 min | 14.4 hr | 1.44 hr | 8.7 min |

TABLE #8-continued

| | Time | | |
|---|---|---|---|
| Depth | $10^{-4}$ S/cm | $10^{-3}$ S/cm | $10^{-2}$ S/cm |
| 0.25 min | 3.8 day | 9.0 hr | 54 min |
| 1 min | 60 days | 6 days | 14.4 hr |

Conductivity was related to the diffusion coefficient by the Nernst-Einstein equation. Exchange of pieces that are thick may take days if the limiting conductivity is low. For membranes of thickness less than 1 mm, exchange times are typically on the order of one to a few hours. The times are considered to be upper estimates since the exchange rate should accelerate as the molar volume and interstitial spaces enlarge with progressive replacement of $Li^+$ by $H^+$.

Passive proton exchange was attempted using two types of proton bearing solutions, 85 percent phosphoric acid and 35 percent nitric solution. Phosphoric acid was chosen because of its high boiling point, >200° C. Proton exchange should occur more rapidly at higher temperatures. Attempts to passively exchange using phosphoric acid solutions were unsuccessful in these experiments. Weights of specimens before and after exchange were nearly unchanged, and electrochemically speaking, these specimens were inactive. The phosphoric acid reacted with the surface of the specimens and formed an ionically insulating layer.

However, passive exchange in nitric acid resulted in weight changes commensurate with replacement $Li^+$ by $H^+$. The extent of exchange was observed to be a function of time and temperature of the nitric acid solution as predicted. TABLE #9 is a list of weights of several specimens of $Li_{1/8}Na_{3/8}La_{1/4}Zr_{1/4}Nb_{3/4}O_3$ sintered at 1250° C. for six hours before and after proton exchange in 35 percent nitric acid solution for 72 hours at 70° C. The thickness of all specimens was approximately 1 mm. The extent of exchange as determined from weight change is also given in TABLE #9 and was greater than 1 in every case.

TABLE #9

| Specimen | Initial Mass | Final Mass | Mass w/o $Li^+$ | Mass with $H^+$ | Extent of Exchange |
|---|---|---|---|---|---|
| 1 | 5.7119 | 5.6734 | 5.6851 | 5.6890 | 1.679 |
| 2 | 5.7156 | 5.6825 | 5.6888 | 5.6926 | 1.455 |
| 3 | 6.3864 | 6.3507 | 6.3564 | 6.3608 | 1.392 |
| 4 | 6.5119 | 6.4646 | 6.4813 | 6.4858 | 1.809 |
| 5 | 6.8304 | 6.7812 | 6.7983 | 6.8030 | 1.794 |
| 6 | 7.1756 | 7.1346 | 7.1419 | 7.1468 | 1.423 |
| 7 | 7.3498 | 7.3114 | 7.3153 | 7.3203 | 1.301 |
| 8 | 7.6546 | 7.6010 | 7.6186 | 7.6239 | 1.744 |
| 9 | 7.7019 | 7.6614 | 7.6657 | 7.6710 | 1.310 |
| 10 | 8.0506 | 7.9997 | 8.0128 | 8.0183 | 1.575 |
| 11 | 8.0807 | 8.0233 | 8.0427 | 8.0483 | 1.769 |
| 12 | 8.1457 | 8.0998 | 8.1074 | 8.1130 | 1.403 |
| 13 | 8.1623 | 8.1126 | 8.1240 | 8.1295 | 1.516 |
| 14 | 8.1746 | 8.1206 | 8.1362 | 8.1418 | 1.645 |
| 15 | 8.1900 | 8.1381 | 8.1515 | 8.1571 | 1.578 |
| 16 | 8.2353 | 8.1829 | 8.1966 | 8.2022 | 1.585 |

Figure 16:
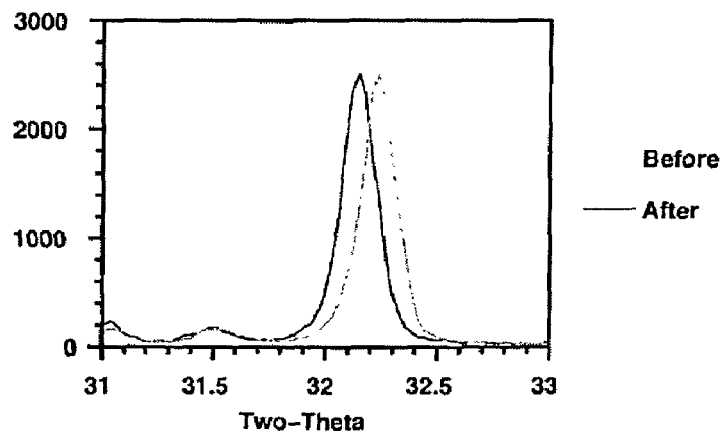
FIG. 16 is a graph of a narrow angle XRD trace that illustrates unit cell expansion in $Li_{1/8}Na_{3/8}La_{1/4}Zr_{1/4}Nb_{3/4}O_3$ by the shift in the (110) peak after proton exchange in nitric acid solution for 72 hours at 70° C.

A small amount of $Na^+$ is suspected to have been replaced by $H^+$. The average extent of exchange for these specimens was 1.56. Proton exchange of $Li_{1/8}K_{1/2}La_{1/8}NbO_3$ and $Li_{1/8}K_{3/8}La_{1/4}Zr_{1/4}Nb_{3/4}O_3$ was also successful and resulted in nearly ideal weight changes. No cracking occurred in any passively exchanged specimens, and enlargement of the unit cell was easily detected by XRD. FIG. 16 shows a powder XRD trace between two-theta angles of 31 and 33° for $Li_{1/8}Na_{3/8}La_{1/4}Zr_{1/4}Nb_{3/4}O_3$ before and after exchanging. The (110) peak shifted from a d-spacing of 2.7786 to 2.7866 Å after exchanging. The linear change in unit cell dimension as calculated from XRD peak shift was +0.25 percent.

Figure 17:
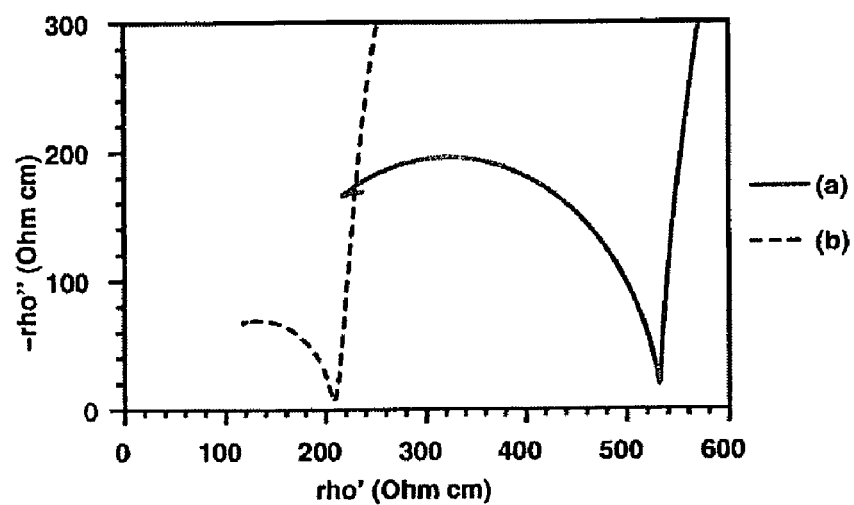
FIG. 17 is a graph illustrating the room temperature protonic impedance of (a) $Li_{1/8}K_{1/2}La_{1/8}NbO_3$ sintered at 1225° C. for 6 hours and (b) $Li_{1/8}K_{3/8}La_{1/4}Zr_{1/4}Nb_{3/4}O_3$ sintered at 1225 for 4 hours after proton exchange in 35 wt % $HNO_3$ for 72 hours at 70° C.
Figure 18:
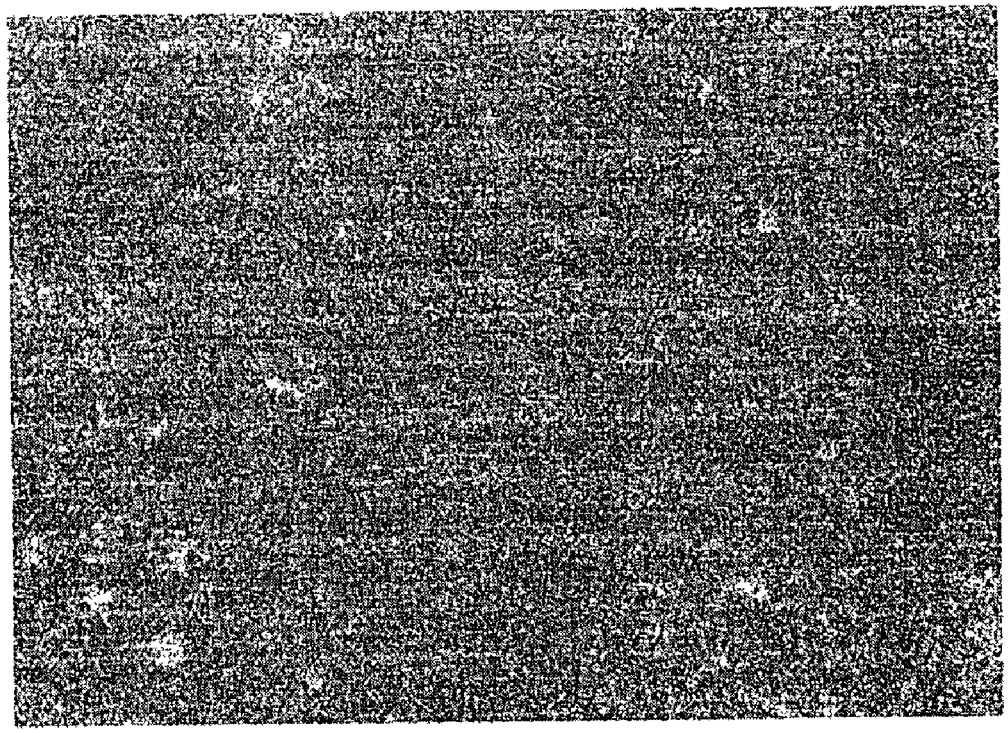
FIG. 18 is an 100× optical photomicrograph of a polished specimen $Li_{1/8}K_{1/2}La_{1/8}NbO_3$.
Figure 19:
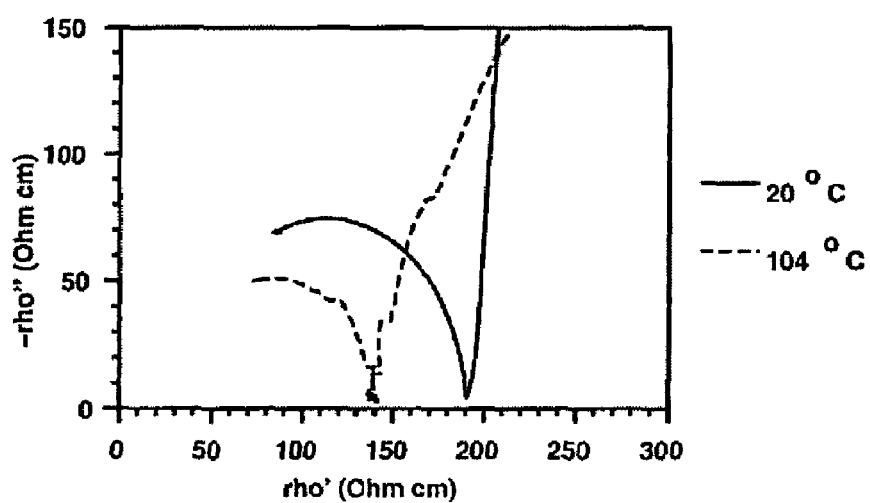
FIG. 19 is a graph illustrating the protonic impedance in $Li_{1/8}Na_{3/8}La_{1/4}Zr_{1/4}Nb_{3/4}O_3$ sintered at 1275° C. for 1 hour after proton exchanging in 35 wt % $HNO_3$ for 72 hours at 70° C.

Protonic conductivity was measured by impedance spectroscopy as described above using 35 wt % $HNO_3$ solution. FIG. 17 is plot of the imaginary versus real components of impedance measured at room temperature over the frequency range $5-2 \times 10^6$ Hz for specimens of $Li_{1/8}K_{1/2}La_{1/8}NbO_3$ (a) (see the 100× optical photomicrograph of a polished specimen of $Li_{1/8}K_{1/2}La_{1/8}NbO_3$ in FIG. 18) and $Li_{1/8}K_{3/8}La_{1/4}Zr_{1/4}Nb_{3/4}O_3$ (b) sintered at 1225° C. for 6 and 4 hours, respectively, after proton exchanging for 72 hours at 70° C. In fact, the exchanged compositions should be referred to as $H_{1/8}K_{1/2}La_{1/8}NbO_3$ and $H_{1/8}K_{3/8}La_{1/4}Zr_{1/4}Nb_{3/4}O_3$. FIG. 19 is an impedance plot for proton exchanged $Li_{1/8}Na_{3/8}La_{1/4}Zr_{1/4}Nb_{3/4}O_3$ measured at room temperature and 104° C. Room temperature protonic conductivity for $H_{1/8}K_{3/8}La_{1/4}Zr_{1/4}Nb_{3/4}O_3$ and $H_{1/8}Na_{3/8}La_{1/4}Zr_{1/4}Nb_{3/4}O_3$ ranged between $3 \times 10^{-3}$ and $6 \times 10^{-3}$ S/cm, and the protonic conductivity of $H_{1/8}K_{1/2}La_{1/8}NbO_3$ is typically ~$2.5 \times 10^{-3}$ S/cm. A key feature of these compositions is that they do not contain nor do they depend upon presence of water that would render them unstable at elevated temperatures. Proton exchanged specimens heated to 650° C. for 1–2 hours and retested after cooling maintain high protonic conductivity.

To summarize this section, three compositions $Li_{1/8}K_{1/2}La_{1/8}NbO_3$, $Li_{1/8}K_{1/8}La_{1/4}Zr_{1/4}Nb_{3/4}O3$, and $Li_{1/8}Na_{3/8}La_{1/4}Zr_{1/4}Nb_{3/4}O_3$ were identified that have $Li^+$ conductivity greater than $2 \times 10-4$ S/cm at room temperature. Proton exchange of these $Li^+$ conductors in $HNO_3$ was demonstrated, and room temperature proton conductivity was measured to be in the range $2 \times 10^{-3}$ to $6 \times 10^{-3}$ S/cm. Proton exchanged material is thermally stable up to 650° C. and may be useful for fuel cells and membrane dehydrogenation reactors (for example).

Niobate Perovskites

New niobate perovskites have been identified that have significantly higher $Li^+$ DC-conductivity, ~$3 \times 10^{-4}$ S/cm. The first composition identified was $Li_{1/8}K_{1/2}La_{1/8}NbO_3$, and it was confirmed by powder x-ray diffraction (XRD) to be single phase and to have a distorted perovskite structure. $Li_{1/8}K_{1/2}La_{1/8}NbO_3$ was used as a guide in the selection of other compositions that may have high $Li^+$ conductivity. The concentrations of $Li^+$ and A-sublattice vacancies are ⅛ and ¼, respectively, per formula unit. Many other compositions were synthesized with these same concentrations. Various combinations of large ions were selected for placement on the A-sublattice, and the aggregate valence of the A-sublattice was adjusted by addition of $Zr^{4+}$ to the B-sublattice. The details of this work have been discussed above in detail. In theory, addition of small ions such as $Li^+$ becomes energetically more expensive as the aggregate valence of the A-sublattice is increased.

Among these candidate compositions, two have been identified that have $Li^+$ conductivity that is comparable to $Li_{1/8}K_{1/2}La_{1/8}NbO_3$. Those compositions are $Li_{1/8}Na_{3/8}$ $La_{1/4}Zr_{1/4}Nb_{3/4}O_3$ and $Li_{1/8}K_{3/8}La_{1/4}Zr_{1/4}Nb_{3/4}O_3$. $Li_{1/8}Na_{3/8}La_{1/4}Zr_{1/4}Nb_{3/4}O_3$. The composition $Li_{1/8}Na_{3/8}La_{1/4}Zr_{1/4}Nb_{3/4}O_3$ was found to be particularly attractive since it can be consistently sintered to a nearly fully dense state over a wide temperature range (1200–1350° C.). The potassium bearing compositions have narrow processing windows perhaps due to the higher volatility of potassium. XRD revealed the presence of monoclinic $ZrO_2$ and $LaNbO_4$ in $Li_{1/8}Na_{3/8}La_{1/4}Zr_{1/4}Nb_{3/4}O_3$. The same second phases were found to be present in the analogous potassium bearing composition but in greater abundance. It is important at this point to emphasize that due to the presence of second phases, the composition of the perovskite ion conducting phase is no longer identical to the batch composition.

Figure 20:
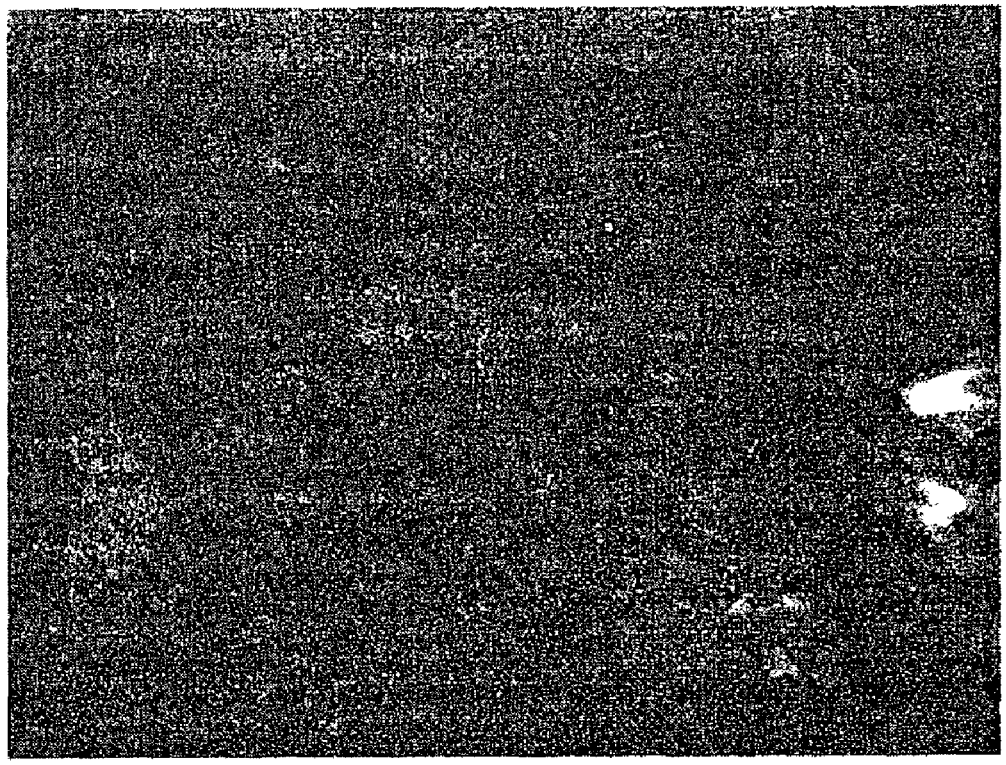
FIG. 20 is an optical micrograph of polished section of $Li_{1/8}Na_{3/8}La_{1/4}Zr_{1/4}Nb_{3/4}O_3$ after proton exchange in $HNO_3$, where grains with steps or bands are $LaNbO_4$ second phase that has twinned in response to shear stress generated by volumetric expansion of the perovskite during proton exchange.

Besides having high $Li^+$ conductivity, the three compositions of electrolytic perovskites have been demonstrated to be capable of exchanging $Li^+$ for protons in acid solutions to become a solid proton conductors (see discussion above). The proton conductivity is typically on the order of 0.005 S/cm. In these materials, high $Li^+$ conductivity is equally important so that proton exchange occurs rapidly. $Li_{1/8}Na_{3/8}La_{1/4}Zr_{1/4}O_3$ is considered a good candidate for use as a solid proton conductor for electrolytic applications since it is easily sintered to an impermeable state. The presence of second phases, however, may have an adverse effect on electrolytic or mechanical properties. Many potential problems associated with the presence of the second phases can be postulated. For example, unit cell expansion of the perovskite phase by ~0.3 percent occurs during proton exchange, but the molar volume of the second phases remain unchanged and cracks could form either immediately or from residual stress over a long period of time. FIG. 20 is an optical photomicrograph taken after proton exchange of a polished specimen of $Li_{1/8}Na_{3/8}La_{1/4}Zr_{1/4}O_3$ and demonstrates the effect of stress from expansion of the perovskite on second phase $LaNbO_4$. It is important to note that the specimen was polished prior to proton exchange. In FIG. 20, $LaNbO_4$ grains twinned and have regularly spaced steps that are no longer flush with the polished surface. $LaNbO_4$ is known to twin easily in response to shear stress.

$Li_{1/8}Na_{3/8}La_{1/4}Zr_{1/4}Nb_{3/4}O_3$ because of its high protonic and $Li^+$ conductivity combined with ease of fabrication make it an attractive candidate for use as an electrolytic membrane in device applications, but it is important to understand the effect of second phases. During the search for other $Li^+$ compositions, it was found that $Li^+$ conductivity of $Li_{1/8}Na_{7/16}La_{3/16}Zr_{1/8}Nb_{7/8}O_3$ is lower by nearly three orders of magnitude than for $Li_{1/8}Na_{3/8}La_{1/4}Zr_{1/4}Nb_{3/4}O_3$, but no second phases were detected. From batch composition, the concentrations of $Li^+$ and A-sublattice vacancies are identical in both cases, only the aggregate valence of the sublattice are different. The two compositions are members of a compositional family that may be written $Li_{0.125}Na_{1-0.5m}La_{0.5m-0.375}Zr_{m-1}Nb_{2-m}O_3$ where "m" is the aggregate valence of the A-sublattice. As stated before, the aggregate valence of the A-sublattice is directly correlated with the quantity of $ZrO_2$ in the batch. Surprisingly, A slight alteration in composition can "switch on" ion conduction. As such, it is believed the presence of second phases may play an important role in ion conduction by causing the development of space charge regions around grain boundaries. On the other hand, they may be purely incidental and that they may be entirely removed by careful adjustments to the batch composition. Accordingly, one of the purposes of this experiment was to examine the relationship between the second phases $ZrO_2$ and $LaNbO_4$ and ion conduction in the $Li_{0.125}Na_{1-0.5m}La_{0.5m-0.375}Zr_{m-1}Nb_{2-m}O_3$ family. Ionic conductivity as a function of "m" in the range 1.125 to 1.25 was measured using impedance spectroscopy. Composition of individual phases was determined by electron microprobe analysis (EPMA), and volume fractions of second phases were measured by surface x-ray diffraction (XRD). Using these results, it is believed that batch compositions of the electrolytic perovskite can be adjusted to try and prevent formation of second phases while preserving the useful electrolytic properties. The ability or inability to obtain a single-phase electrolytic perovskite that possess high $Li^+$ conductivity is important in the understanding of the mechanism of ion conduction.

Specimens for ion conductivity measurement, XRD analysis, and EPMA analysis were prepared using traditional ceramic processing techniques. Powders of the pure carbonates and oxides were weighed in such quantities as to give 30 g of oxide of each composition. The weighed powders were wet mixed for 24 hours in a 250 ml Nalgene bottle using 530 g of zirconia milling media and isopropanol as the solvent. The mixed slurry was poured into a Pyrex beaker and dried on a hot plate while stirring to prevent demixing. Dried powders were reacted at 950° C. for 1 hour in platinum crucibles to form the perovskite ion conducting phase. The reacted powder was wet milled for 24 hours using 530 g of zirconia milling media and isopropanol as the solvent to reduce particle size and facilitate sintering. The milled slurry was dried on a hot plate while stirring to prevent settling. The dried and reacted powder was sieved through a 225 mesh nylon screen. Pills of the obtained powders were formed by uniaxially pressing in a cylindrical die having a 3.2 cm diameter at a pressure of 2500 $lb/in^2$. Pills were sintered on platinum foil at 1200, 1250, and 1300° C. for 4 hours in an electric furnace.

After sintering, $Li^+$ conductivity was measured using impedance spectroscopy. The procedure and method for conductivity measurement was described above with respect to FIG. 4. Briefly, the specimens were clamped using rubber o-rings into a glass testing fixture to isolate opposite faces. An aqueous solution composed of 150 g $LiNO_3$ and 5 g $Li_2CO_3$ per L was poured into each side of the fixture and two platinum wire electrodes were immersed into the solution, one per face of the specimen. The platinum wires were placed as close as possible to the faces of the specimens without making contact. The aqueous solution acts as a source and sink of $Li^+$ to minimize electrode charge transfer resistance, and $CO_3^{2-}$ suppresses proton concentration. Both of actions were taken to ensure an accurate measurement of bulk, DC $Li^+$ conductivity.

Composition and phase constitution of the specimens were determined using electron microprobe analysis (EPMA) and surface XRD. Specimen preparation for EPMA involved polishing of surfaces to a finish of 1 $\mu$m. Surfaces of all specimens for XRD were ground flat using 320 grit silicon carbide grinding paper.

EPMA analyses were performed on a JEOL 8900 Superprobe. The analyses were performed using an accelerating potential of 12 keV and a beam current of 30 nA. All elements were counted on peak for 30 seconds using a focused beam.

TABLE #10

| Assumed Scattering Composition | Phase | Peak (hkl) | d-spacing (A) | Unit Cell Volume (A) | Volumetric Coefficient |
|---|---|---|---|---|---|
| $ZrO_2$ | monoclinic | ($\bar{1}11$) | 3 165 | 140.47 | 89 10 |
| $ZrO_2$ | monoclinic | (111) | 2 836 | 140 47 | 65 88 |
| $LaNbO_4$ | monoclinic | ($\bar{1}21$) | 3.250 | 332.97 | 110.31 |
| $LaNbO_4$ | monoclinic | (121) | 3.092 | 332.97 | 96.60 |
| $Li_{1/8}Na_{3/8}La_{1/4}Zr_{1/4}Nb_{3/4}O_3$ | cubic perovskite | (100) | 3 923 | 60 37 | 48 58 |
| $Li_{1/8}Na_{3/8}La_{1/4}Zr_{1/4}Nb_{3/4}O_3$ | cubic perovskite | (110) | 3 923 | 60 37 | 99 42 |

The average of the thirty analyses for each sample was then normalized to the stoichiometric composition of the standard perovskite.

The use of the working standard perovskite simplifies these analyses greatly for the following reasons. The elemental mobilities of Li and Na are assumed to be very similar between the sample and working standard perovskites. This assumption is based on the fact that the total range in perovskite composition among all the samples is small and the lower abundance elements (La and Zr) exhibit the largest compositional variation. However, this technique is not ideal and as such the data should be thought of as semi-quantitative. The relative differences between the different perovskites, however, are extremely well characterized which enabled these experiments to, determine what causes the large change in ionic conductivity with bulk composition.

Figure 21:
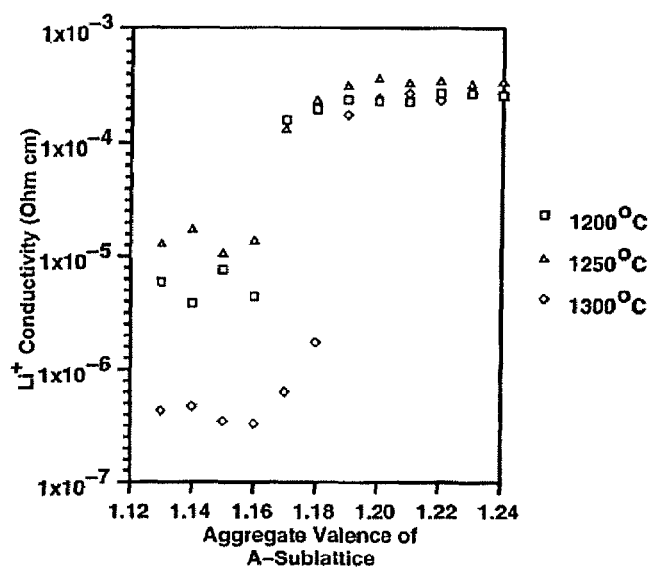
FIG. 21 is a graph illustrating the $Li^+$ conductivity of the batch composition $Li_{0.125}Na_{1-0.5m}La_{0.5m-0.375}Zr_{m-1}Nb_{2-m}O_3$ as a function of "m" (aggregate valence of the A-sublattice) for three different firing temperatures.

The effect of second phases on $Li^+$ conductivity in the $Li_{0.125}Na_{1-0.5m}La_{0.5m-0.375}Zr_{m-1}Nb_{2-m}O_3$ family of batch compositions was investigated for m=1.13 to 1.24 in divisions of 0.01 for specimens fired for 4 hours at temperatures of 1200, 1250, and 1300° C. FIG. 21 is plot of $Li^+$ conductivity as measured by impedance spectroscopy as a function of "m". Conductivity shows the same trend at all three firing temperatures. At small values of "m", conductivity is low, but rises abruptly by two to three orders of magnitude between m=1.16 and 1.2. The highest and lowest conductivities measured were $3.65 \times 10^{-4}$ and $3.29 \times 10^{-7}$ S/cm, respectively. Firing temperature does appear to have an effect on conductivity for "m" in the low conductivity regime. Specimens fired at 1300° C. have noticeably lower conductivity than specimens fired at 1200 or 1250° C. For "m" in the high conductivity regime, firing temperature does not have as dramatic an effect, nevertheless, the highest conductivities were measured for specimens fired at 1250° C. It should be understood that the measured conductivity in these lithium niobates indicated a discontinuity or a step-change as a function of the composition.

Surface XRD was used to determine the volume fractions of second phases present in these specimens. The procedure for the analysis involved the following. First, volumetric x-ray scattering coefficients were calculated for each phase at two different diffraction peaks from the crystal structure according to Equation #6:

$$\alpha_{phase}^{hkl} = \frac{I_{phase}^{hkl}}{V_{cell}^2} \quad (6)$$

where $V_{cell}$ is the cell unit volume used to calculate the diffracted intensity, I, for the peak given by the superscript hkl from the phase given by the subscript. TABLE #10 lists the peaks selected for each phase to be used in the analysis, as well as the corresponding volumetric scattering coefficients. The compositions of the second phase monoclinic $ZrO_2$ and monoclinic $LaNbO_4$ were assumed to be ideal, and these assumptions appear to be justified based upon the EPMA that will be discussed in what follows. The composition of the perovskite ion conducting phase was assumed to be $Li_{1/8}Na_{3/8}La_{1/4}Zr_{1/4}Nb_{3/4}O_3$. This assumption is justified for the following three reasons. First, the perovskite composition does not change dramatically over the range of "m" considered in these experiments. Second, Zr and Nb which both reside on the B-sublattice have nearly indistinguishable atomic scattering coefficients. Third, ions on the B-sublattice have higher atomic numbers and dominate the volumetric scattering coefficient. It should also be noted that ions on the B-sublattice, and ions and vacancies on the A-sublattice were distributed randomly in the calculation. Volume fractions of the individual phases were determined by relating the measured XRD intensity to volume using the volumetric scattering coefficient, see Equation #7:

$$V_{phase}^{hkl} = \sqrt{\frac{I_{phase}^{hkl}}{\alpha_{phase}^{hkl}}} \quad (7)$$

The volume fraction of each phase is therefore, see Equation #8:

$$v_i = \frac{V_i^{hkl}}{\sum_j V_j^{hkl}} \quad (8)$$

Figure 22:
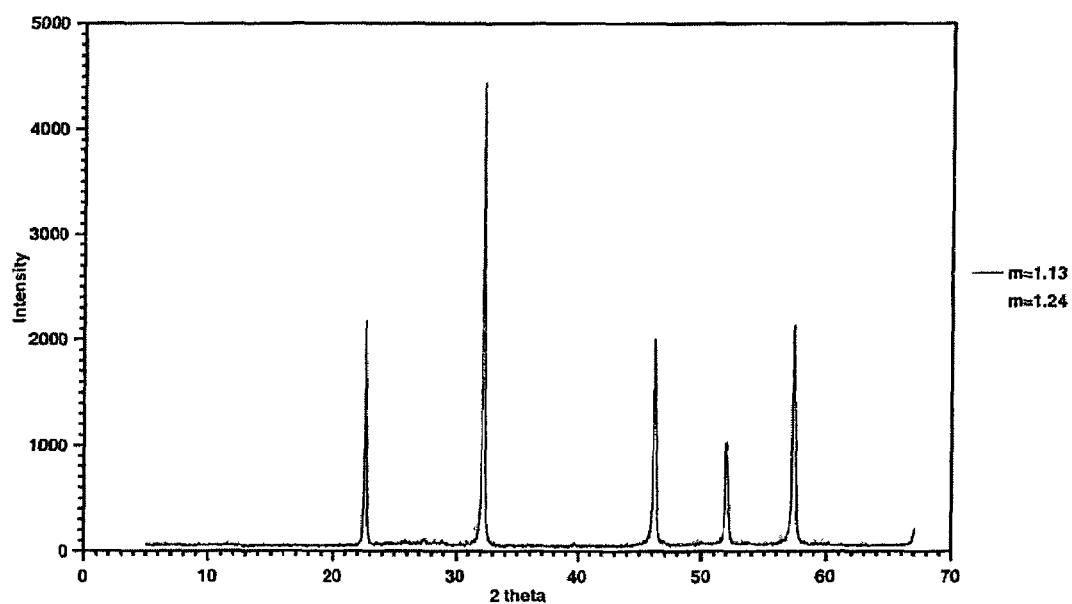
FIG. 22 is a graph illustrating XRD traces of specimens with m=1.13 and 1.24 fired at 1250° C. for 4 hours.
Figure 23:
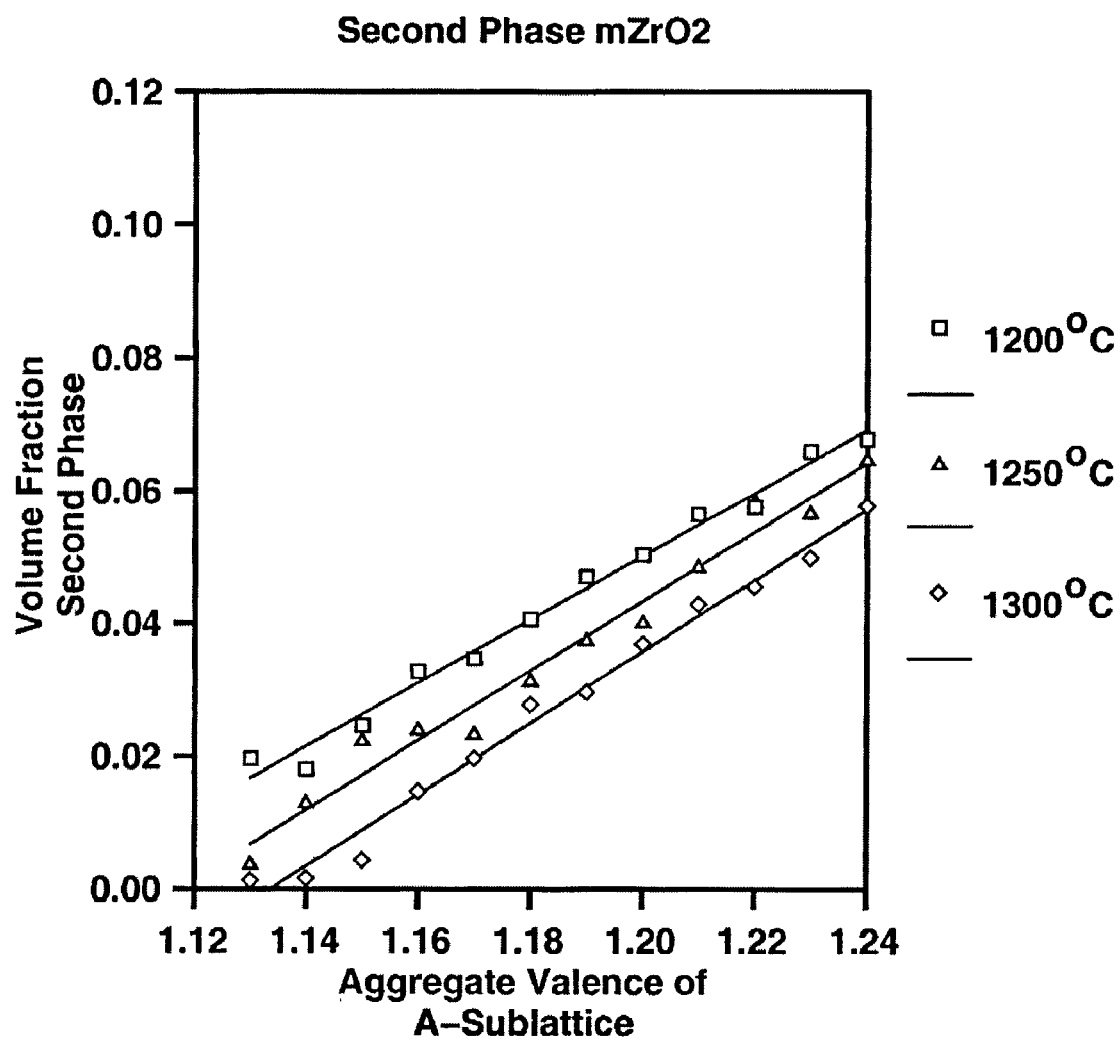
FIG. 23 is a graph illustrating the volume fraction of second phase monoclinic $ZrO_2$ as a function of "m" in specimens having the batch composition $Li_{0.125}Na_{1-0.5m}La_{0.5m-0.375}Zr_{m-1}Nb_{2-m}O_3$.
Figure 24:
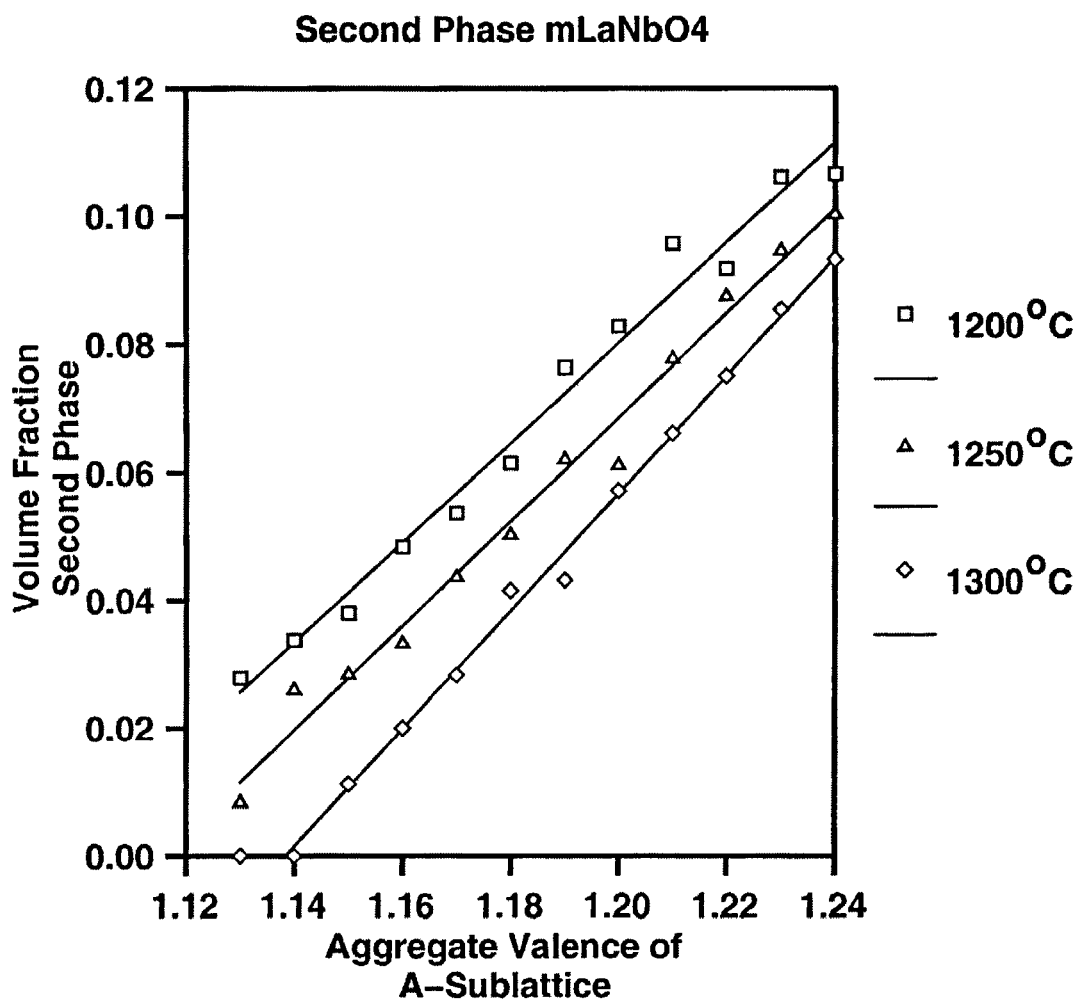
FIG. 24 is a graph illustrating the volume fraction of second phase monoclinic $LaNbO_4$ as a function of "m" in specimens having the batch composition $Li_{0.125}Na_{1-0.5m}La_{0.5m-0.375}Zr_{m-1}Nb_{2-m}O_3$.

FIG. 22 is a surface XRD traces for specimens fired at 1250° C. for 4 hours having the batch compositions corresponding to m=1.13 and 1.24. The quantity of second phases is clearly greater for the specimen with m=1.24 as evidenced by the increased intensity for peaks located between 27 and 30 degrees two-theta. FIGS. 23 and 24 are plots of the calculated volume fractions of second phase monoclinic $ZrO_2$ and monoclinic $LaNbO_4$, respectively, for the three sintering temperatures. The trend is clear, quantities of second phases increase with increasing "m". Quantity of second phase is lower for higher sintering temperatures. Extrapolation of the regression-fitted lines for the quantity of second phase to the x-axis reveals that $LaNbO_4$ and $ZrO_2$ begin to form at the same value of "m". This conclusion is made without knowing if the $ZrO_2$ present as second phase was unreacted batch material or if it was expelled from a reaction product during sintering or calcining. These results were examined in conjunction with the measured ionic conductivities. No discontinuities or abrupt changes in phase constitution are observed in the XRD data that coincide with the onset of high conductivity for m>1.17. No explanation for the high lithium ion conductivity of specimens with m>1.17 was obtained from the XRD analysis.

Figure 25A:
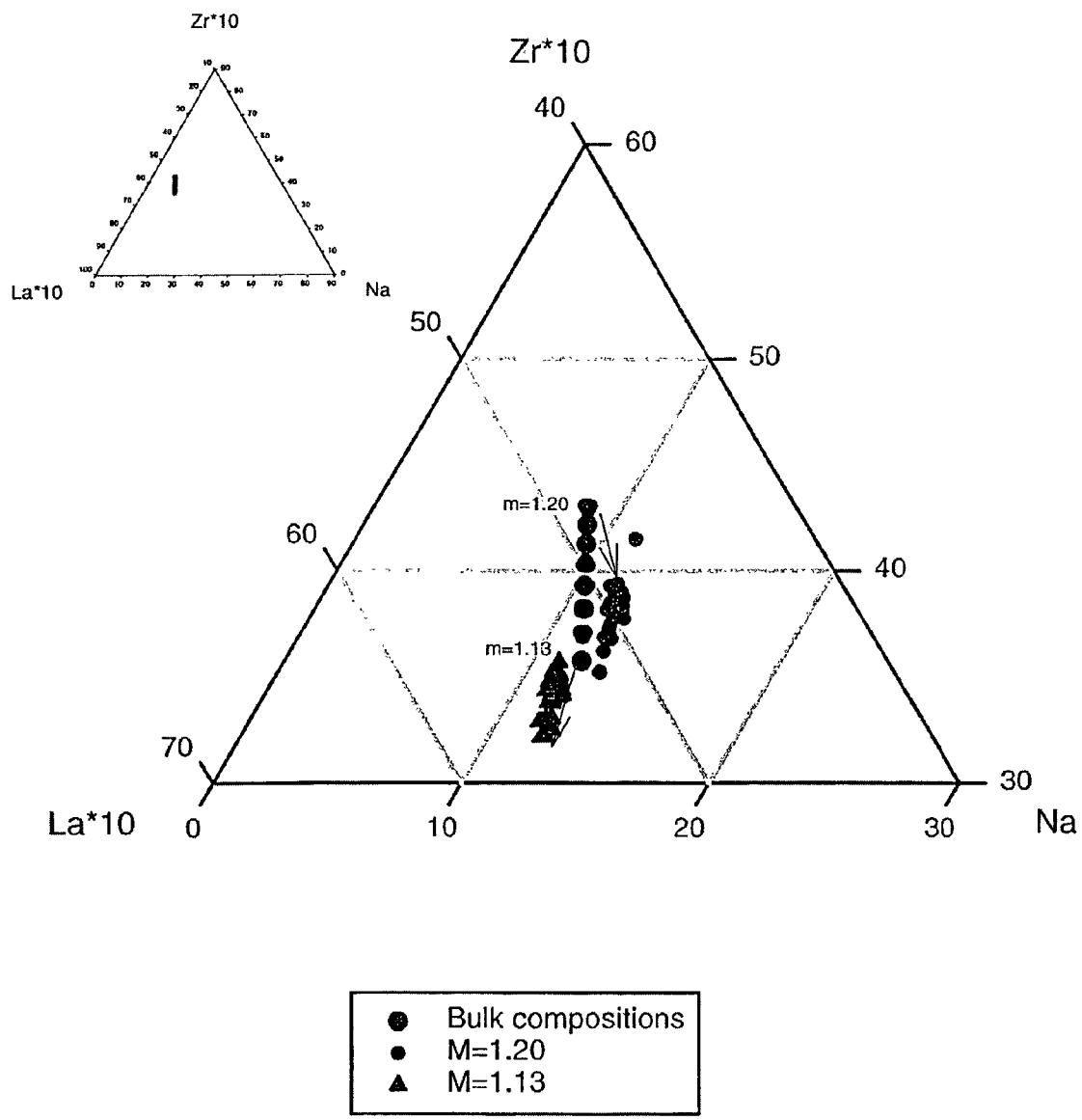
FIGS. 25A–25C are graphs illustrating intra-sample variations in compositions for specimens with m=1.13 and 1.20 fired at 1250° C. for 4 hours as plotted on a ternary map for La:Na:Zr, La:Nb:Zr and Na:Nb:Zr, respectively.
Figure 25B:
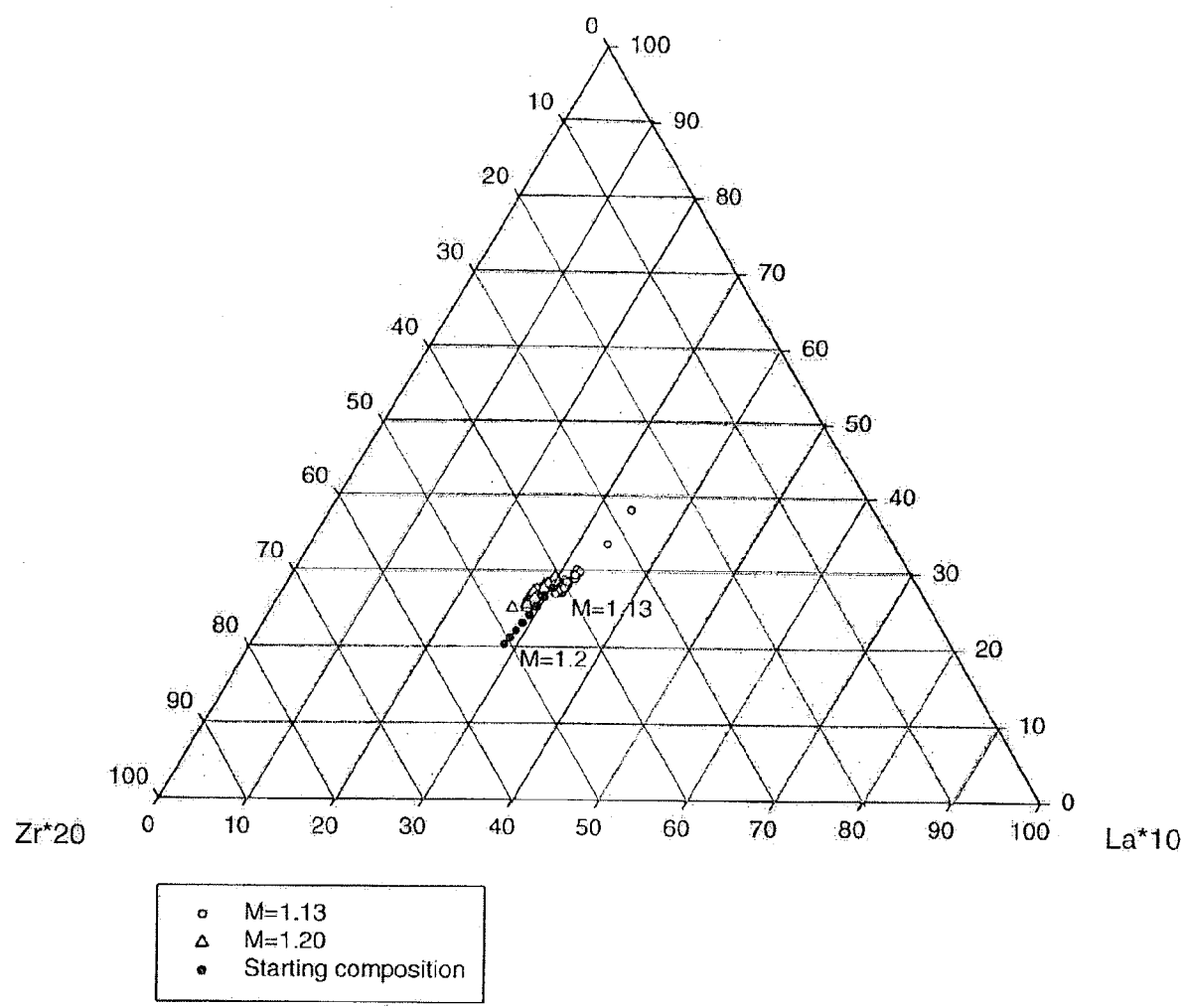
Figure 25C:
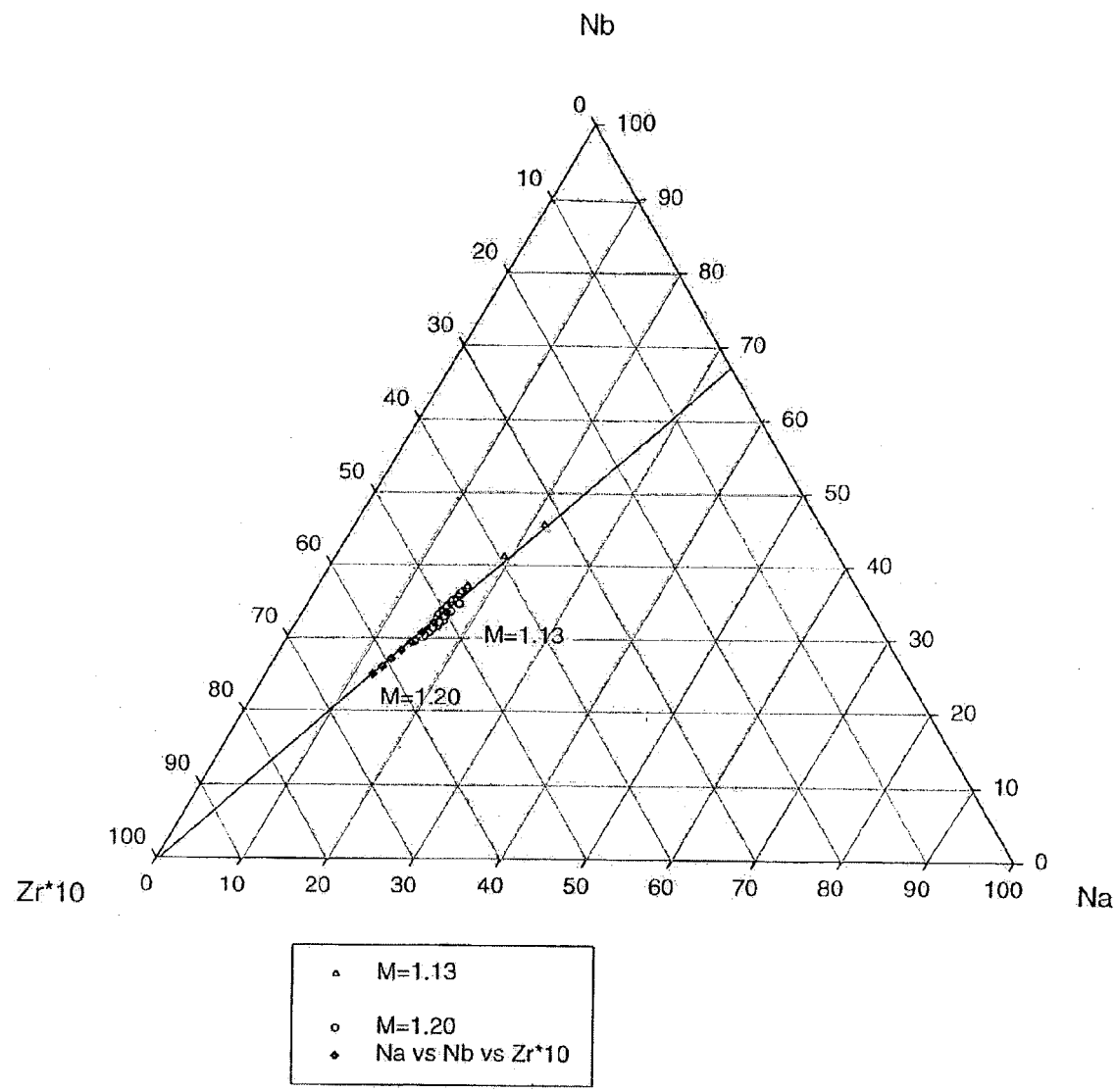
Figure 26A:
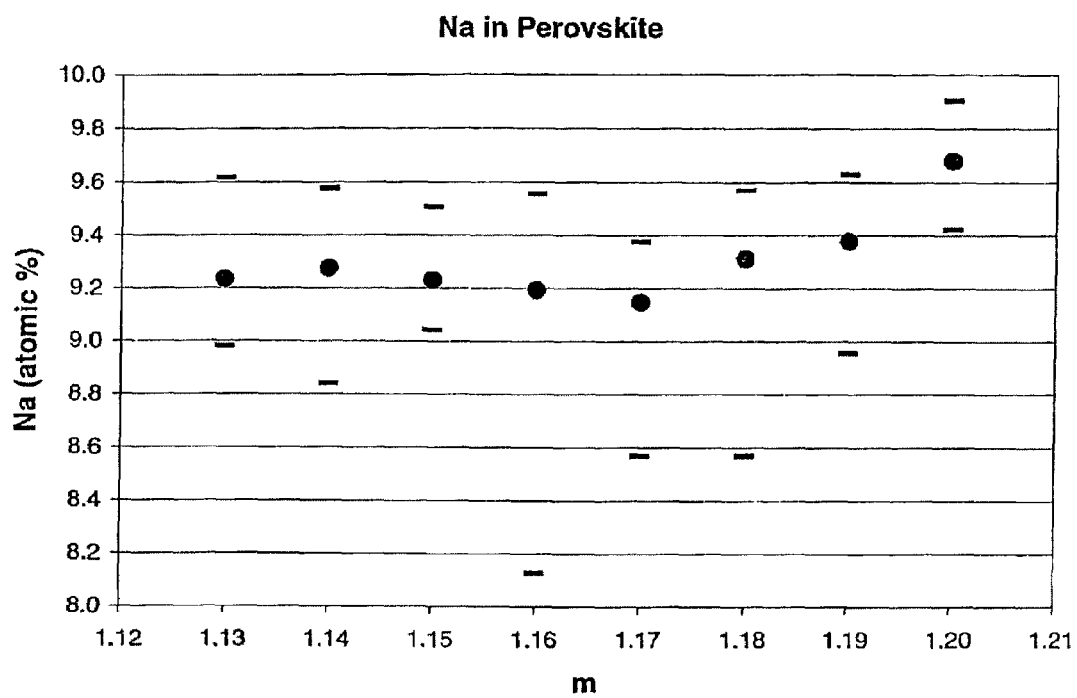
FIGS. 26A–26E are graphs illustrating plots of a composition (inter-sample) as a function of "m" for specimens sintered at 1250° C. for 4 hours, Na, La, Zr, Nb, and O, respectively.
Figure 26B:
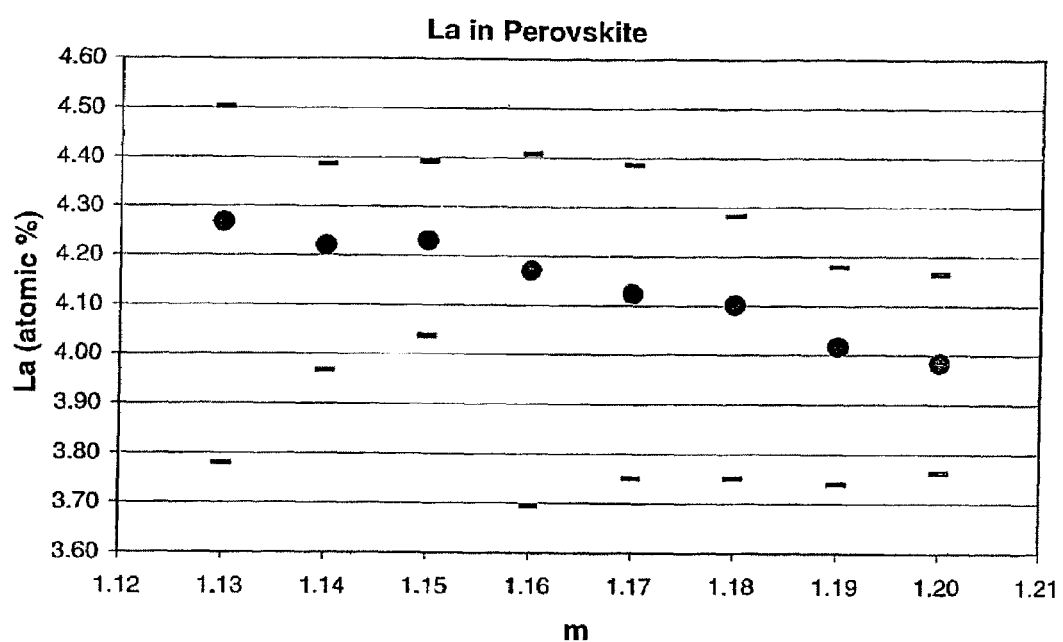
Figure 26C:
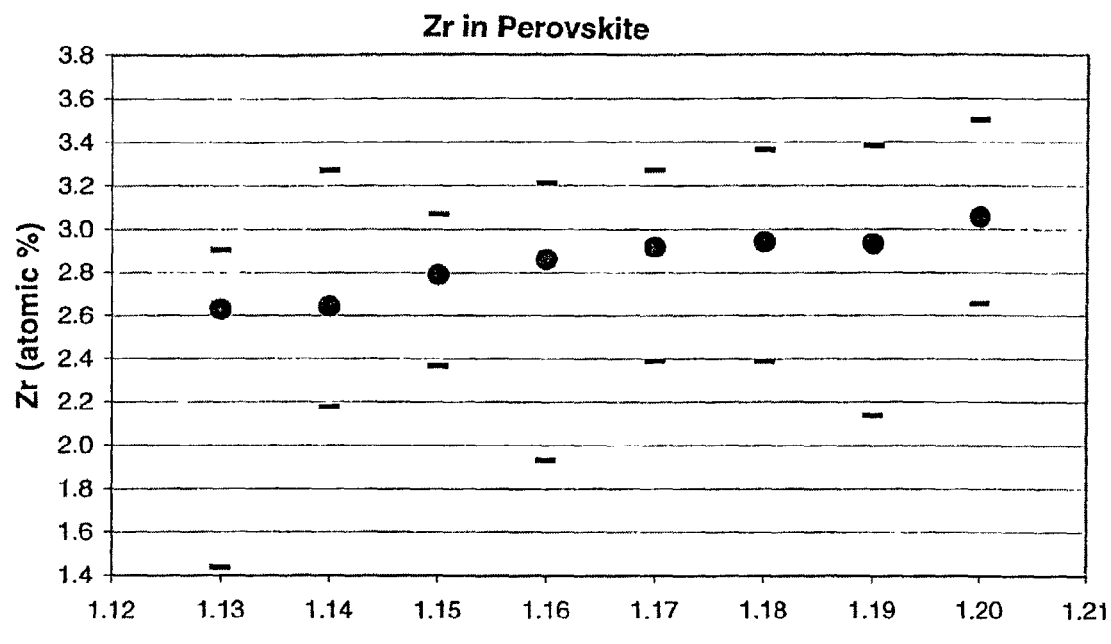
Figure 26D:
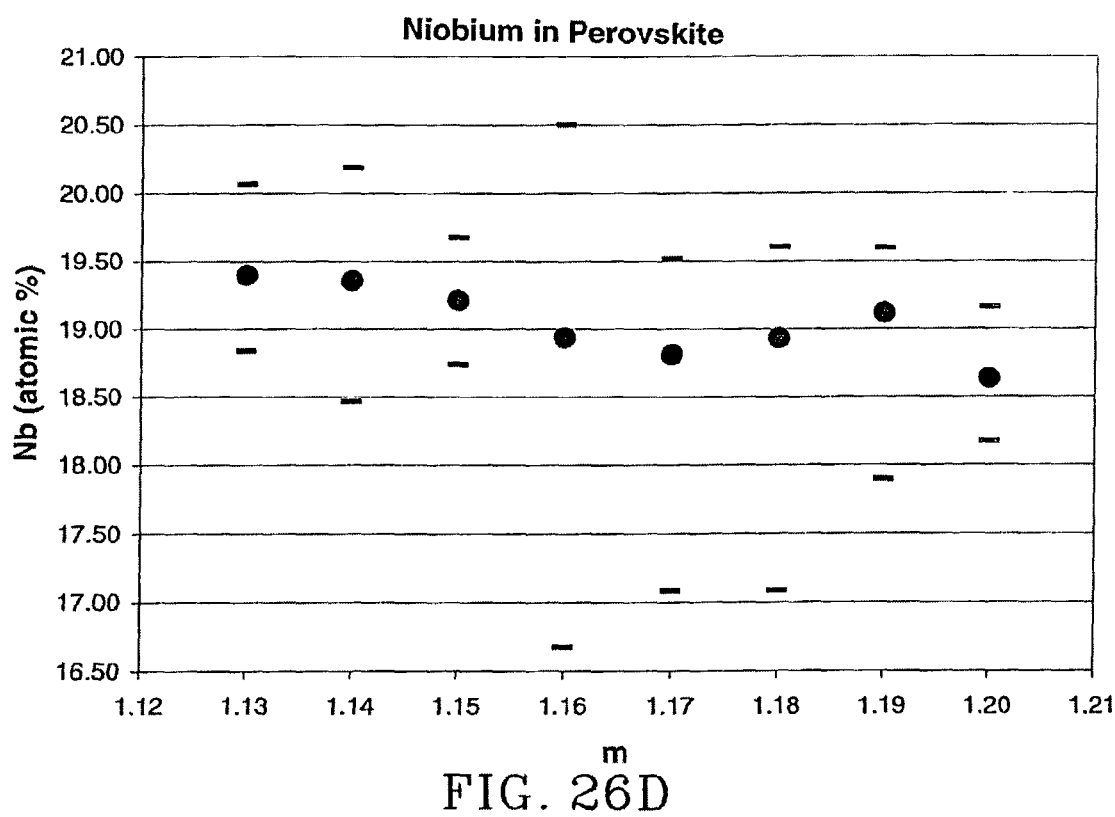
Figure 26E:
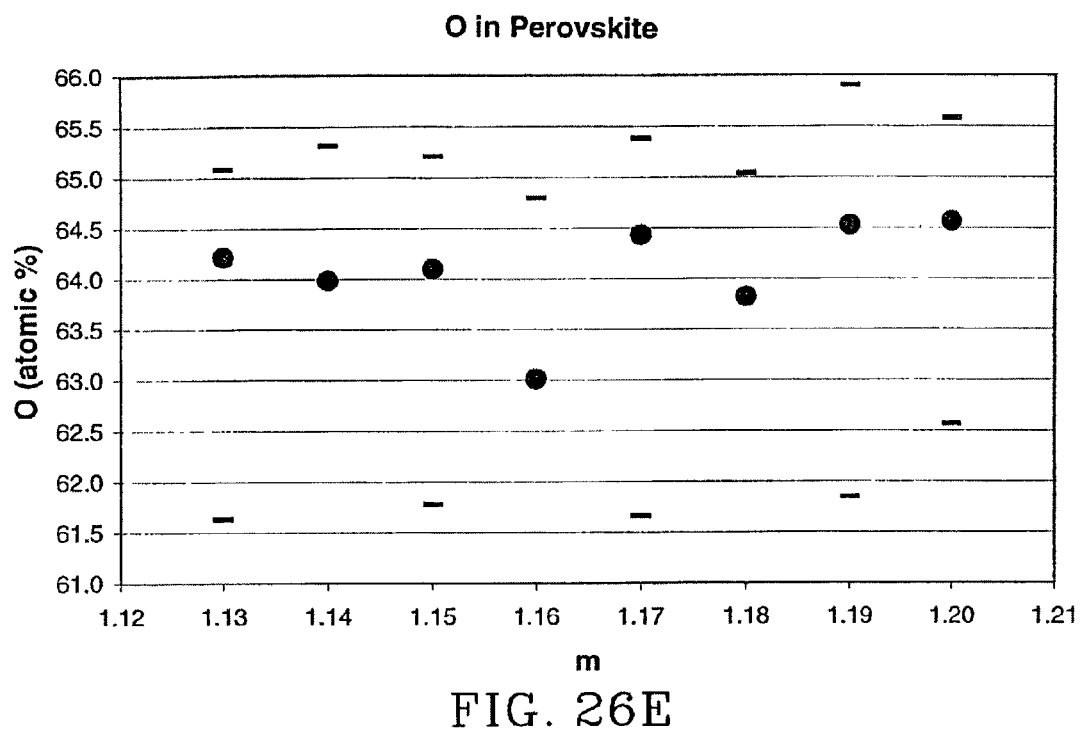

Electron microprobe was selected to examine the composition of the individual phases themselves from composition-to-composition (inter-sample) and as distributed within individual specimens (intra-sample). Electron microprobe data clearly show the intra-sample chemical inhomogeneity of the perovskite crystals in these specimens. At first glance, the inhomogeneity seems extremely complex. When plotted on ternary diagrams, the data appears to be somewhat systematic. FIGS. 25A–25C show the positions of the starting compositions. The La:Nb, Na:La, and Na:Nb ratios remained essentially constant within each experiment, while Zr varied with respect to the other elements. The chemical trends appear to primarily reflect the growth of the $ZrO_2$ second phase during sintering. The growth of the second phase $LaNbO_4$ is reflected in the slight deflections of the trends toward the Nb and La corners of the ternary diagrams. The preservation of intra-sample variability reflects the sluggish kinetics of diffusion for La, Zr, and Nb in all three phases.

Compositional analysis of the second phases revealed that second phase material having the monoclinic $ZrO_2$ structure is essentially pure. It is likely that this second phase is unreacted batch material. Similarly, the $LaNbO_4$ second phase which occurs in greater abundance contains less than one percent of Na or Zr. The $LaNbO_4$ is slightly deficient in $Nb_2O_5$ by approximately 2 percent. The reactions to form desired perovskite and $LaNbO_4$ occur competitively. Once formed, $LaNbO_4$ reacts only slowly with the already formed perovskite and $ZrO_2$ for two reasons. First, diffusions of La, Nb, and Zr in all three phases is expected to be very slow. Second, the arrangement of the phases requires material transport over large distances to achieve complete reaction to form the perovskite. Particles of $ZrO_2$ and $LaNbO_4$ appear from the microstructure to make contact with the perovskite phase alone, and not with one another. Higher sintering temperatures did not significantly affect the quantity of second phases.

FIGS. 26A–26E show the average concentrations of all elements in the perovskite phase measured by microprobe as a function of "m" for specimens sintered at 1250° C. The oxygen content of the perovskite is constant, Nb and La decrease, and Zr increases as a function of "m", as expected. Concentrations of Zr and Nb on the B-sublattice and O on the O sublattice are consistent with complete occupancy as predicted by defect chemistry. It should be noted that there is no abrupt change in the concentrations of these elements in the perovskite near m=1.16 where lithium ion conductivity begins to increase. On the other hand, the concentration of Na is constant from m=1.13 to 1.16 and then begins to increase as a function of increasing "m". However, concentration of Li could not be determined with certainty.

Comparison of intra- and inter-sample composition variation by examination of FIGS. 25 and 26 together show that within the same specimen, composition of the perovskite phase varies by as much as the explored compositional range. Once again, the reason for the wide range of perovskite composition is because of competitive reaction kinetics and slow long-range diffusion of La, Zr, and Nb in all phases. From this observation, it was concluded that bulk composition for these perovskites is not the determining factor for development of high lithium ion conductivity. Nevertheless, it should understood that the bulk composition of the perovskite should fulfill minimum requirements for ion conduction such as presence of a mobile species such as $Li^+$, presence of large concentration of vacancies, and large interstitial sites that do not impede hopping of ions from site to vacancy. All of the perovskite niobates in these experiments have bulk compositions that satisfy these requirements. The high lithium ion conductivity of these ceramics is the result of an unusual grain boundary composition or structure.

Removal of second phase materials by adjustment of batch composition was attempted using the information obtained from the XRD analysis. Composition of the second phases were assumed to be stoichiometric $ZrO_2$ and $LaNbO_4$. Removal of the second phases is desirable since they may have adverse effects on mechanical and ion conduction properties. Mass of the second phases were estimated using molecular weights and densities of each phase. A mass of $ZrO_2$ equal to the quantity predicted by the analysis to remain in the fired pieces was removed from the batch. Similarly, masses of $La_2O_3$ and $Nb_2O_5$ equal to the mass of $LaNbO_4$ predicted to form during firing was removed from the batch. Two specimens using compositions for m=1.20 and 1.25 as starting points were prepared for conductivity measurement and XRD analysis to observe any second phases. The compositions of these two specimens were $Li_{0.1454}Na_{0.4653}La_{0.1963}Zr_{0.1348}Nb_{0.8652}O_3$ and $Li_{0.1454}Na_{0.4653}La_{0.1963}Zr_{0.1348}Nb_{0.8652}O_3$, respectively. Lithium ion conductivity of specimens sintered at 1250° C. for 4 hours was consistent with conductivity of other specimens conforming to the unmodified batch compositions for m<1.17, that is to say, conductivity was quite low. XRD showed the presence of second phase monoclinic $ZrO_2$ and $LaNbO_4$ in both specimens, but in lower quantities as compared to the unmodified batch compositions.

To summarize, second phases do not appear to be required for the development of high lithium ion conductivity. The second phases are a consequence of competitive reaction kinetics and sluggish long-range diffusion. No abrupt changes in either the composition or proportions of second phases were observed near the onset high ionic conductivity. The onset of rapid ion conduction was correlated with an increase in sodium concentration in the perovskite phase. A unique grain boundary composition or structure is believed to be responsible for rapid ion conduction in these ceramics.

It should be understood that there are many potential applications or devices which can incorporate and use the electrolytic perovskite and proton conductors of the present invention. For example, the electrolytic perovskite can be used in a fuel cell, sensor, battery, membrane reactor and steam electrolysis applications. Following are some of the applications that can use the electrolytic perovskite or the solid proton conductor of the present invention.

Amperometric Hydrocarbon Sensor for Gaseous Hydrocarbons

Several countries have current or pending legislation that mandates reductions in emission of pollutant gases such as hydrocarbons from sources such as automobiles. These laws also stipulate monitoring of emissions at the source for verification of compliance. Thus, there is a growing need for a cheap, rugged hydrocarbon sensor that has a rapid response time, high selectivity, and sensitivity on the order of one part per million for operation in harsh environments.

Hydrocarbon reactions having the form shown below are facilitated by partial oxidation dehydrogenation catalysts (PODHC's) such as zinc ferrites:

$$R-CH_2CH_3 + \tfrac{1}{2}O_2 \rightarrow R-CH=CH_2 + H_2O \qquad (9)$$

The dehydrogenation step in this reaction leads to the transient adsorption of hydrogen on to the surface of the catalyst. If adsorption is viewed from the perspective of bonding, there must be an exchange of charge between hydrogen and the catalyst. Adsorbed hydrogen can be considered as partially ionized with a compensating electron delocalized in the catalyst. This step, accounting for transfer of charge, can be described by the following reaction:

$$R\text{—}CH_2CH_3 \rightarrow R\text{—}CH\text{=}CH_2 + 2\ H^{\delta+}(\text{adsorbed}) + 2\delta e^- \quad (10)$$

During normal operation of a PODHC, the adsorbed hydrogen rapidly reacts with any available oxygen to give $H_2O$ in accord with reaction (9).

Figure 27:
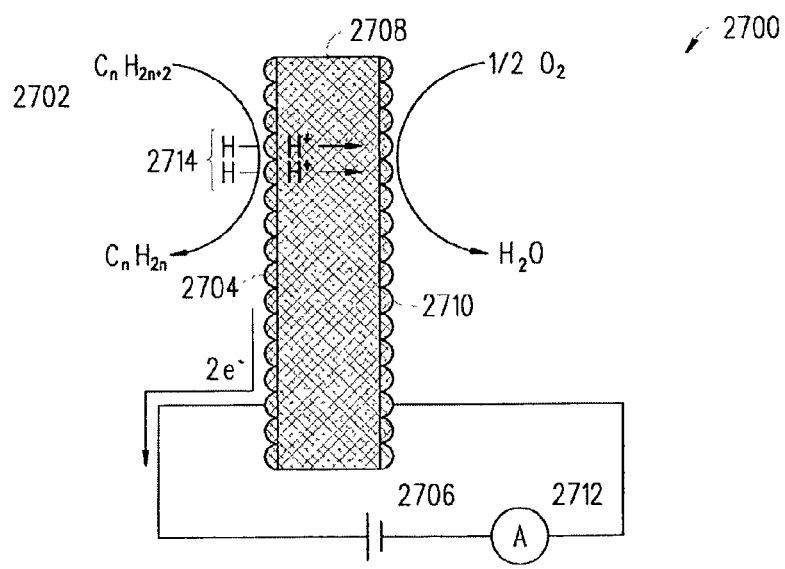
FIG. 27 is a block diagram of an amperometric hydrocarbon sensor incorporating a proton conducting solid of the present invention.

An interesting use for a PODHC is as an electrode for the production of protons by electrochemical oxidation. Thus, the present invention includes an amperometric hydrocarbon sensor 2700 that detects and measures gaseous hydrocarbons based upon a PODHC electrode 2704 in conjunction with a proton conducting electrolyte 2708 is shown in FIG. 27. The mechanism for operation of the amperometric hydrocarbon sensor 2700 is as follows. A hydrocarbon from the gas 2702 is dehydrogenated on the PODHC 2704 in accordance with reaction (10). A small power supply 2706 provides a constant voltage drop across the proton conducting electrolyte 2708. In response to the applied voltage, the adsorbed hydrogen are oxidized to form protons, and the removed electrons are swept from the catalyst 2704 and forced to traverse an external path. The protons travel through the proton-conducting electrolyte 2708 and on arrival at the reduction electrode 2710 can go on to react with oxygen to form water. An ammeter 2712 measures the current flowing through the external circuit due to oxidation of adsorbed hydrogen. The measured current is directly proportional to the hydrocarbon concentration in the gas 2702.

The rate of oxidation of the transiently adsorbed hydrogen 2714 on the catalyst electrode 2704 in the presence of an externally applied voltage is given by Equation #11:

$$j_{net} = k_\rightarrow P_{C_nH_{2n+2}} - k_\leftarrow P_{C_nH_{2n}} e^{\frac{2e\phi}{k_BT}} \quad (11)$$

where $k_\rightarrow$ and $k_\leftarrow$ are rate constants for the forward and reverse reactions, respectively, $P_{C_nH_{2n+2}}$ and $P_{C_nH_{2n}}$ are the pressures of gaseous hydrocarbon and its dehydrogenated product, respectively, e is the unit charge, $\Phi$ is the overpotential at the catalyst-electrolyte interface, T is the absolute temperature, and $k_B$ is Boltzmann's constant. For no externally applied voltage, $\Phi=0$, the net rate of proton formation is zero, $j_{net}=0$. Applying this condition, Equation #11 may be rewritten as Equation #12:

$$j_{net} = k_\rightarrow P_{C_nH_{2n+2}}\left(1 - e^{\frac{2e\phi}{k_BT}}\right) \quad (12)$$

Thus, the net rate of oxidation of hydrogen on the PODHC electrode 2704 to form protons is directly proportional to the concentration of hydrocarbons in the gas 2702, i=k[HC].

Figure 28:
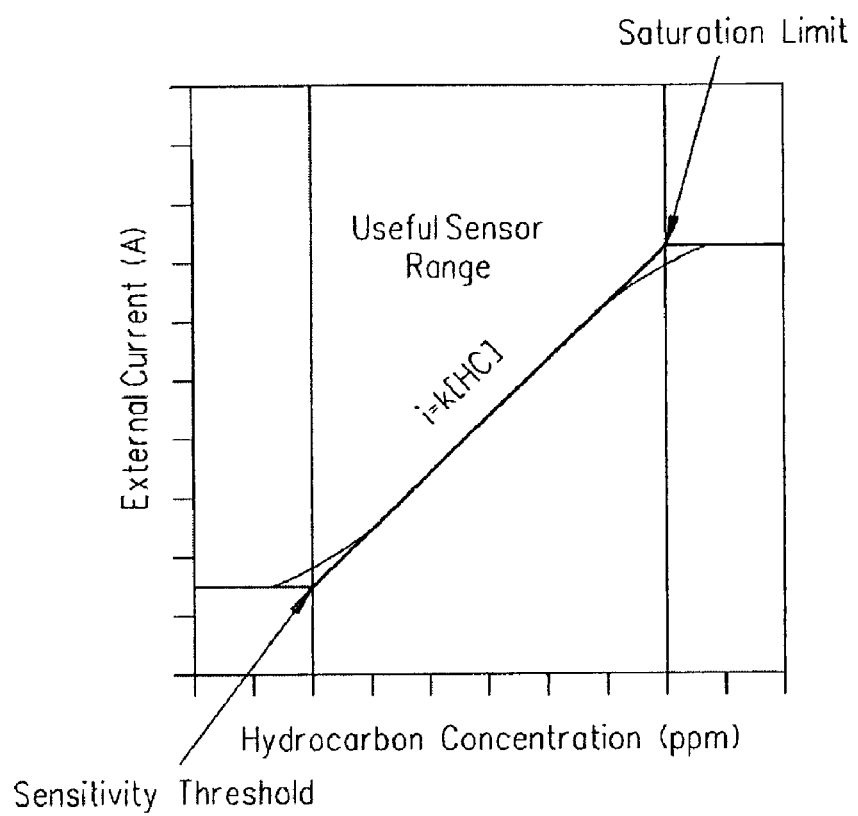
FIG. 28 is a graph illustrating the current versus voltage response of the amperometric hydrocarbon sensor shown in FIG. 27.

The measurable current in the external circuit can be affected by the following four factors: (1) the availability of hydrocarbons 2702 for formation of protons; (2) the protonic conductivity of the proton conducting electrolyte 2708; (3) the rate of the charge transfer reaction occurring on the opposite electrode 2710; and (4) the electronic conductivity of the proton conducting electrolyte 2708. In the preferred embodiment of the amperometric hydrocarbon sensor 2700, the current flowing through the external circuit is controlled by the availability of hydrocarbons from the gas phase. To accomplish this, the protonic resistivity of the proton conducting electrolyte 2708, and the charge transfer resistances of the electrodes 2704 and 2710 should be as low as possible to prevent saturation. These two factors taken together could limit the maximum detectable hydrocarbon concentration. The lowest detectable hydrocarbon concentration which is referred to as the sensitivity threshold is controlled by the electronic transference number of the proton conducting electrolyte 2708. The electronic transference number of the proton conducting electrolyte 2708 should be less than 0.1 which implies that the electronic resistivity should be at least an order of magnitude greater than the ionic resistivity. In the range between the sensitivity threshold and the saturation limit, the external current, as measured by the ammeter 2712, is directly proportional to the hydrocarbon concentration in the gas 2702 as given by Equation #12. FIG. 28 is a theoretical plot of the externally measured current versus hydrocarbon concentration.

The sensitivity threshold and detectable range are figures of merit that are useful to judge performance. Besides the intrinsic kinetic properties of the proton conducting electrolyte 2708 and electro-catalysts 2704 and 2710, design factors such as geometry and microstructure can also affect performance. To a large extent, proper design of geometry and microstructural features can overcome some limitations imposed by intrinsic kinetic properties of the proton conducting electrolyte 2708 and electro-catalysts 2704. Further, an optimized design achieves a broad range of sensitivity that is, to a first approximation, unaffected by temperature fluctuations or the presence of competitive gases such as CO, $H_2$, $CO_2$, etc.

Figure 30:
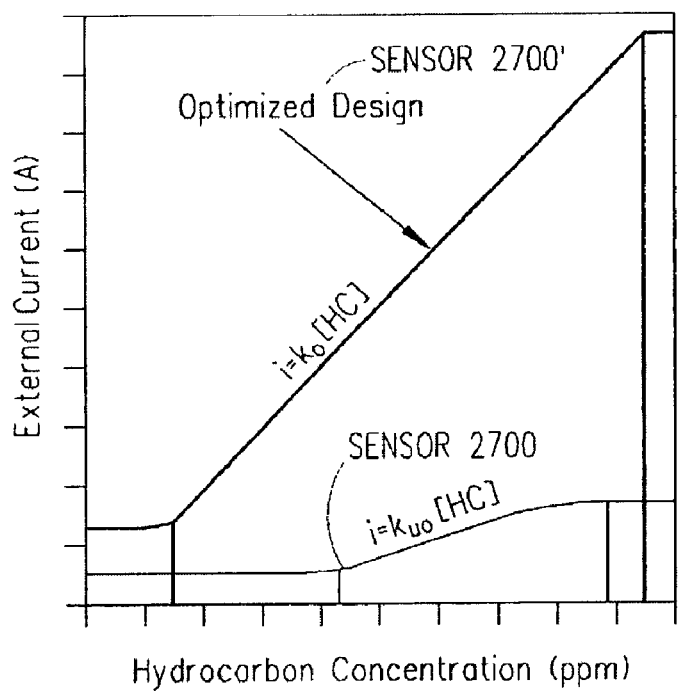
FIG. 30 is a graph of the current response versus hydrocarbon concentration for the amperometric hydrocarbon sensors shown in FIGS. 27 and 29 which illustrates the improved sensitivity obtained by optimizing various design factors such as electrode microstructure, electrolyte thickness, and the use of a precatalyst layer over a PODHC electrode to remove competitive gases such as $H_2$ and CO.
Figure 29:
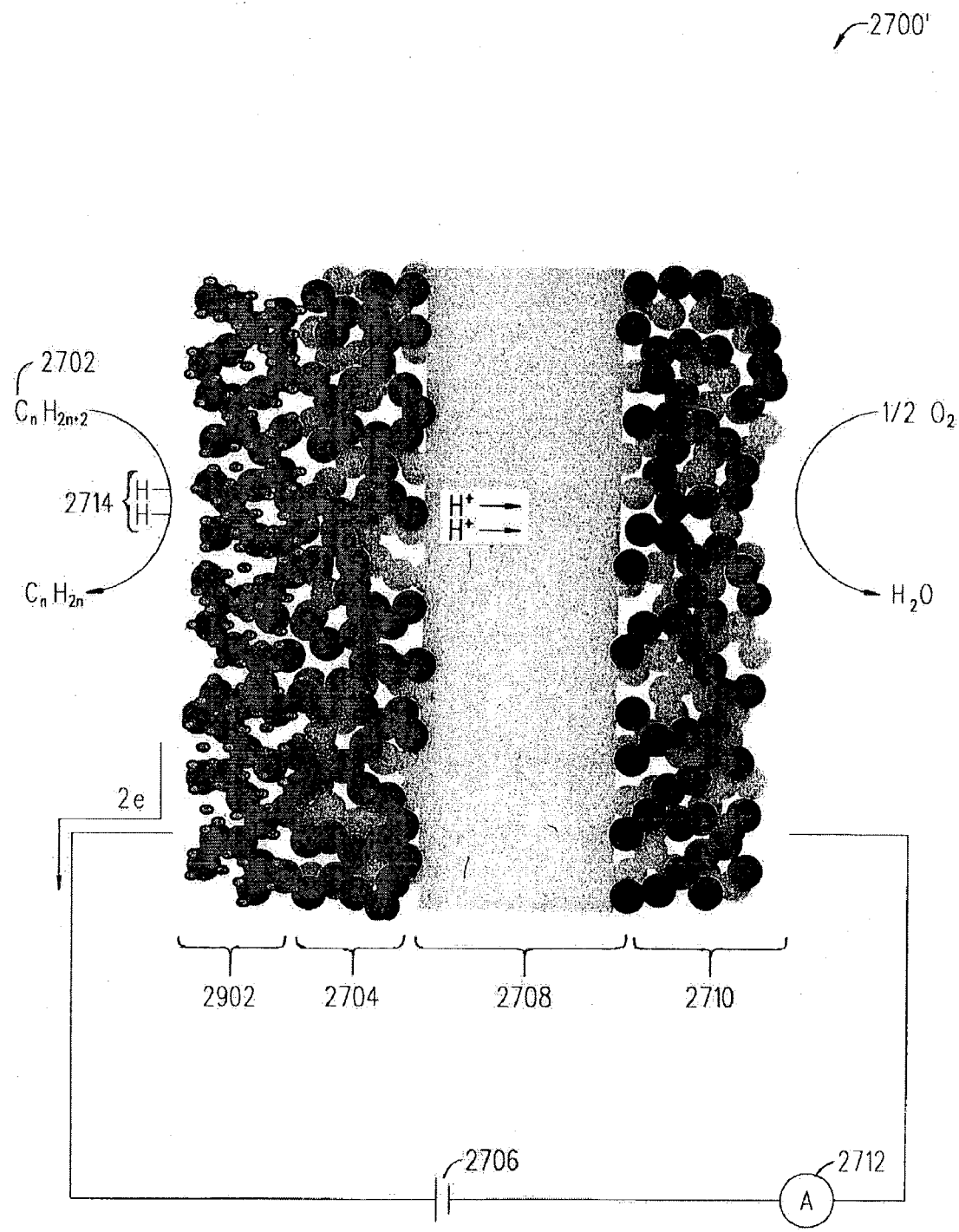
FIG. 29 is a block diagram of another embodiment of an amperometric hydrocarbon sensor incorporating a proton conducting solid of the present invention.

The electrode-electrolyte interface plays an important role in the performance of the amperometric hydrocarbon sensor 2700 since it is the location where charge transfer reactions occur. At temperatures below 900° C., resistance to charge transfer is often the dominating term in total internal resistance. Composite electrodes with a judiciously chosen thickness that consist of a mixture of continuous phases of proton conducting electrolyte, electrocatalyst (PODHC), and porosity have lower effective resistance to oxidation and reduction of protons in the electrodes 2704 and 2710 (see FIG. 29). The size of the proton conducting electrolyte 2708 and electrocatalyst particles that constitute the electrode 2704 should also be as small as possible. The resistance to flow of protons is reduced by decreasing the thickness of the electrolyte membrane. Further, a porous pre-catalyst layer 2902 deposited on top of the PODHC electrode 2704 may be useful for removal of gases such as $H_2$ and CO that could compete with hydrocarbons for active sites on the catalyst surface. FIG. 29 shows an illustration of the amperometric hydrocarbon sensor 2700' that takes advantage of the aforementioned design concepts. FIG. 30 illustrates the difference in performance obtained between amperometric hydrocarbon sensors 2700 and 2700' when otherwise identical materials are used to construct the sensors 2700 and 2700'. The current response of the amperometric hydrocarbon sensor 2700' has the following advantages: (1) the sensitivity threshold is lower; (2) the maximum detectable hydrocarbon concentration is higher; (3) the constant relating hydrocarbon concentration to current in the useful sensing range is larger ($k_o > k_{uo}$); and (4) a less sensitive ammeter can be used due to the higher electric current.

To summarize, the amperometric hydrocarbon sensor 2700 and 2700' enables the quantitative detection and monitoring of gaseous hydrocarbon species such as are present in automotive exhaust and industrial emissions. The amperometric hydrocarbon sensor 2700 and 2700' includes the following components: a proton conducting electrolyte 2708 with a low electronic transference number, a partial oxidation dehydrogenation catalyst (PODHC) electrode 2704, a small power supply 2706, and an ammeter 2712. Upon exposure of this amperometric hydrocarbon sensor 2700 and 2700' to a hydrocarbon-containing gas 2702, transiently adsorbed hydrogen 2714 forms on the PODHC 2704 or precatalyst layer 2902. The adsorbed hydrogen is electrochemically oxidized by the power supply 2706, and the resultant protons are conducted through the electrolyte 2708. The ammeter 2712 measures current flow in an external circuit that within a certain range is directly proportional to the concentration of hydrocarbon species in the gas 2702.

Fuel Cell

Figure 31:
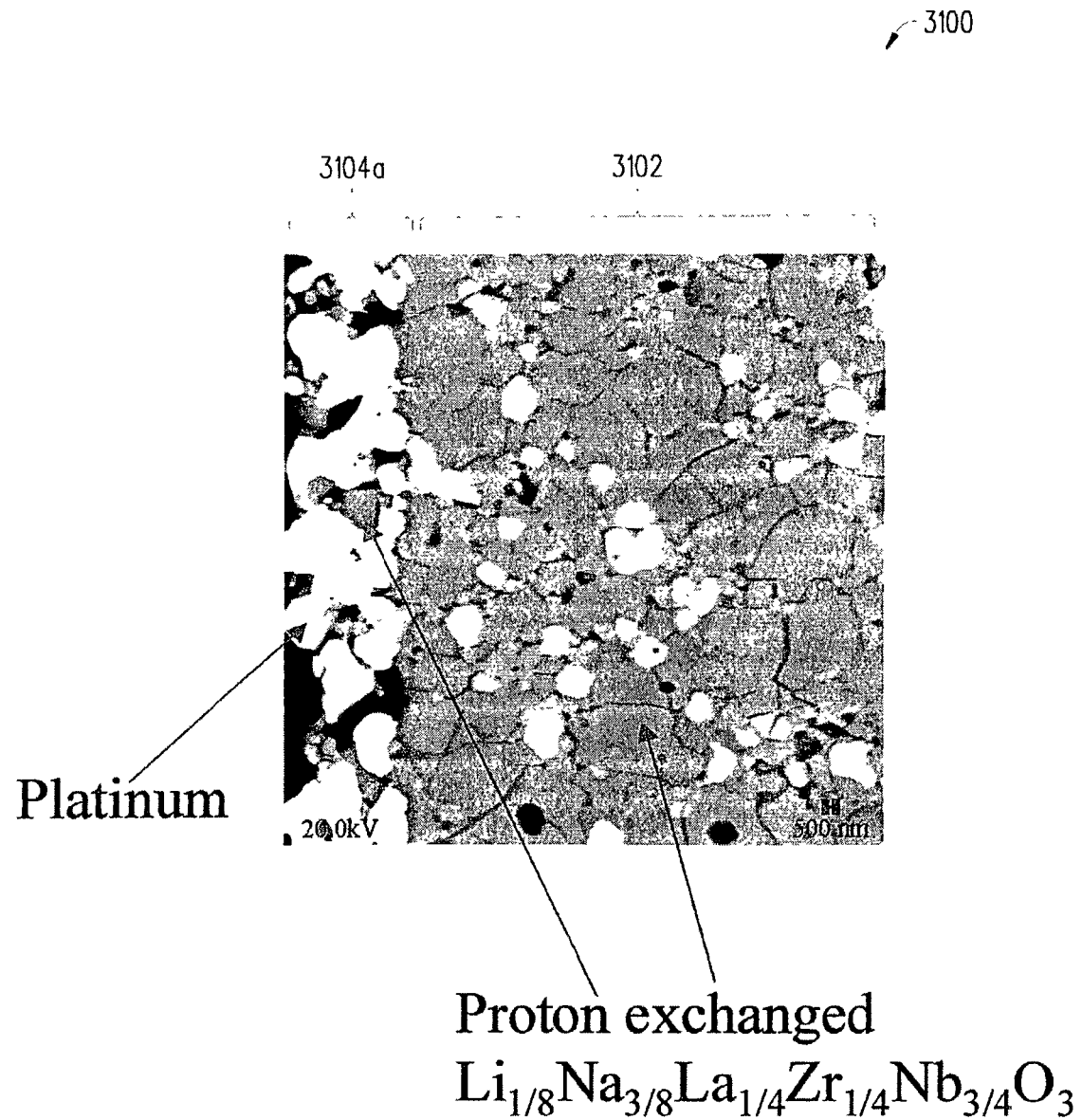
FIG. 31 is a SEM photo of a polished cross-section of a disk and electrode making up a fuel cell incorporating a proton conducting solid of the present invention.
Figure 32:
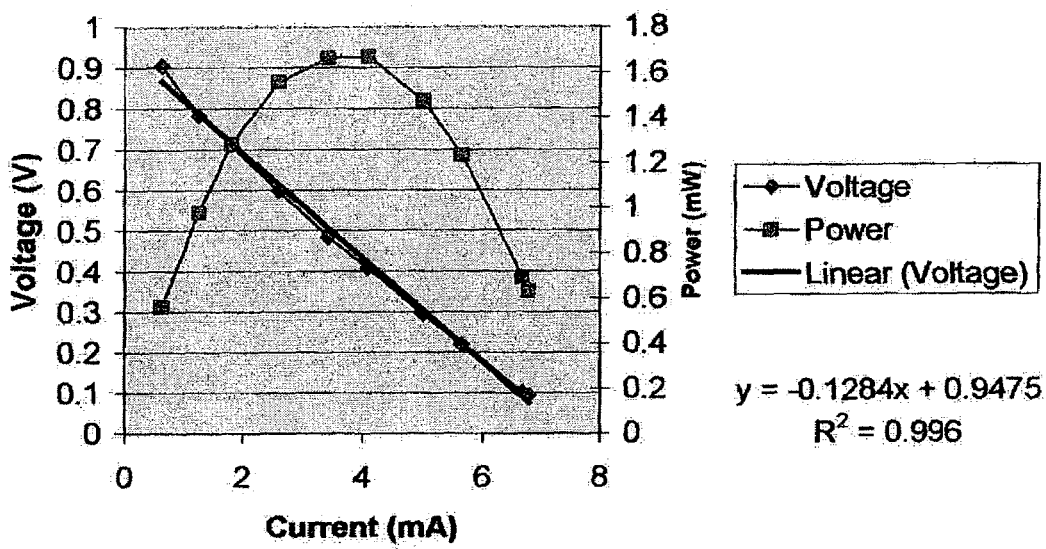
FIG. 32 is a plot of voltage and power versus current under one set of conditions for the exemplary fuel cell shown in FIG. 31.

FIG. 31 is a SEM photo of a polished cross-section of a disk 3102 and electrode 3104a making up a fuel cell 3100 in accordance with the present invention. The electrode region 3104a is clearly visible. The fuel cell 3100 in this example includes a disk 3102 of $Li_{1/8}Na_{3/8}La_{1/4}Zr_{1/4}Nb_{3/4}O_3$ (electrolytic perovskite) that was fired at 1225° C. for 4 hours. The disk 3102 had a fired diameter of ~4.4 cm and a thickness of 1.4 mm. Two electrodes 3104a (only one shown) of equal parts platinum and $Li_{1/8}Na_{3/8}La_{1/4}Zr_{1/4}Nb_{3/4}O_3$ were applied by painting of an ink. The ink was prepared by mixing powders of platinum and $Li_{1/8}Na_{3/8}La_{1/4}Zr_{1/4}Nb_{3/4}O_3$ with a solution of 6 weight percent methocellulose dissolved in Texanol (Kodak) using a steel spatula. The texanol solution was added progressively to the $Pt/Li_{1/8}Na_{3/8}La_{1/4}Zr_{1/4}Nb_{3/4}O_3$ powders while mixing until a homogeneous, viscous paste was obtained. The ink was painted onto one side of the $Li_{1/8}Na_{3/8}La_{1/4}Zr_{1/4}Nb_{3/4}O_3$ disk 3102 using a small brush and isopropanol as a thinner. The disk 3102 was fired, ink side up, at 1225° C. for 1 hour to form the first electrode 3104a. The second electrode (not shown) was applied to the uncoated face of the disk 3102 by painting, just as in the first case, and the part was fired again at 1225° C. for 1 hour, green electrode up. The disk 3102 with attached electrodes was proton exchanged in 10% nitric acid solution for in excess of 2 weeks. FIG. 32 is a plot of voltage and power versus current for the exemplary fuel cell 3100.

The test of the fuel cell 3102 was performed at room temperature using the arrangement similar to the one shown in FIG. 4. Two modified beakers similar to beakers 402a and 402b shown in FIG. 4 were filled with ~250 ml of distilled water. Three grams of powdered sodium borohydride, $NaBH_4$, was added to one beaker. The electrode which can't be seen in FIG. 31 but was exposed to this $NaBH_4$-solution is the anode. Ten milliliters of 30% hydrogen peroxide, $H_2O_2$, was added to the water in the other beaker. The electrode 3104a immersed in this solution is the cathode. Bubbles of $H_2$ could be seen forming on the surface of the anode. Similarly, bubbles of $O_2$ were forming on the cathode. The active electrode area was measured to be 9 cm$^2$. The current versus voltage curve deviates from linearity in the low current regime near the open circuit condition. Least squares regression of the data estimates the open circuit voltage to be ~0.95 V which is an underestimate. By extrapolating along the curve to the open-circuit condition, the CCV is closer to ~1.05 V which is a reasonable value for a couple of $O_2$ with diluted $H_2$. The area specific resistance was determined to be 1200 $\Omega cm^2$.

Figure 33:
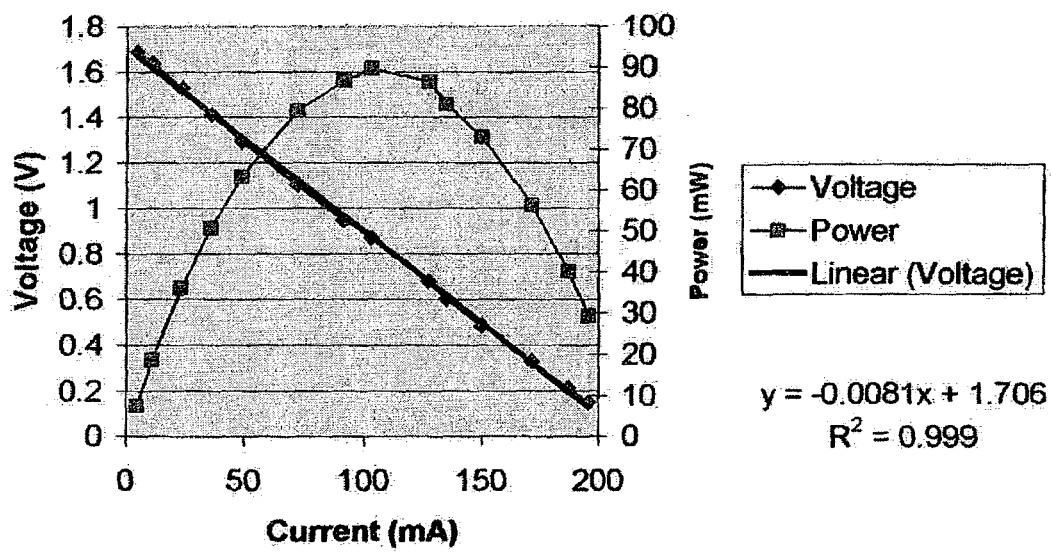
FIG. 33 is a plot of voltage and power versus current under another set of conditions for the exemplary fuel cell shown in FIG. 31.

FIG. 33 is a plot of voltage and power versus current for another sample of a fuel cell made in the same manner and at the same time as the one described above. However, conditions for the test differed. The temperature of the test was 60° C. The aqueous solutions for the anode and cathode were altered. The anode was exposed to a mixture of 20 g KOH and 15 g $NaBH_4$ in 300 ml $H_2O$. The cathode was immersed in 48 g HCl 72 g $H_2O_2$ dissolved in 300 ml $H_2O$. KOH stabilized/slowed decomposition of $NaBH_4$, and HCL stabilized/slowed decomposition of $H_2O_2$. The open circuit voltage of the device is substantially higher in this case, ~1.7 V, as compared to the first example. The increase in open circuit voltage reflects a change in the electrode kinetics indicating that the couple is no longer dilute $H_2$ with $O_2$. Area specific resistance of the cell is 73 $\Omega cm^2$.

In both tests it was noticed that the internal resistance is much higher than could be attributed to the solid proton conducting $H_{1/8}Na_{3/8}Li_{1/8}Na_{3/8}La_{1/4}Zr_{1/4}Nb_{3/4}O_3$ alone. The two electrodes 3104a of which only one can be seen in FIG. 31 are the source of the additional resistance.

Dehydrogenation Membrane

Another opportunity is the use of a proton conducting solid as a membrane in a dehydrogenation membrane for the chemical processing and polymer industry. Dehydrogenation reactions are used in the production of unsaturated hydrocarbons from saturated feed stock and are typically conducted by the addition of controlled amounts of $O_2$. For example, the partial oxidation-dehydrogenation reaction for the production of styrene from ethylbenzene occurs by the reaction:

$$R\text{—}CH_2CH_3 + \tfrac{1}{2}O_2 \rightarrow R\text{—}CH\text{=}CH_2 + H_2O \tag{13}$$

where, for example, R is an aromatic group.

The yield of the reaction is low, and addition of excess oxygen to drive the reaction results in unwanted oxidation reactions. Styrene produced this way must be purified from water, unreacted ethylbenzene, and any unwanted products. Theoretically, higher yield without occurrence of undesirable oxidation reactions can be obtained if a high temperature mixed proton-electron conductor is used as a membrane to separate ethylbenzene and styrene from oxygen and water. The purified styrene is subsequently used as monomer by the plastics industry to manufacture polystyrene. In general, costs associated with nearly all dehydrogenation reactions involving partial oxidation can be lowered by the increased yield and higher purity of the product. The market opportunity for a new material with proton conductivity >$10^{-4}$ S/cm in the temperature range 200–600° C. is conservatively estimated to be worth more than 200 million dollars.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An elctrolytic that is a solid with an ion conductivity greater than $10^{-5}$ S/cm in a temperature range of 0–400° C., wherein said perovskite has a chemical formula of $Li_{1/8}K_{3/8}La_{1/4}Zr_{1/4}Nb_{3/4}O_3$.

2. An electrolytic perovskite that is a solid with an ion conductivity greater than $10^{-5}$ S/cm in a temperature range of 0–400° C., wherein said perovskite has a chemical formula of $Li_{1/8}K_{3/8}La_{1/4}Zr_{1/4}Nb_{3/4}O_3$.

3. An electrolytic perovskite that is a solid with an ion conductivity greater than $10^{-5}$ S/cm in a temperature range of 0–400° C., wherein said perovskite has a chemical formula of and $Li_{1/8}Na_{7/16}La_{3/16}Zr_{1/8}Nb_{7/8}O_3$ with no detectable second phases $ZrO_2$ and $LaNbO_4$.

4. An electrolytic perovskite having the following chemical formula:

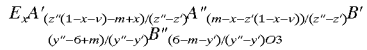

where:
E is a mobile ion;
A' and A" are ions with valences z' and z", respectively;
m is the aggregate valence per A-site;
B' and B" are ions with valences y' and y", respectively;
x is the concentration of mobile ions; and
v is the concentration of vacancies, and wherein at least a portion of the ions are replaced by protons so as to form a solid proton conductor.

5. The electrolytic perovskite of claim 4, wherein said solid proton conductor has a proton conductivity of at least about $5 \times 10^{-3}$ S/cm at 20° C.

6. The electrolytic perovskite of claim 5, wherein said solid proton conductor has a proton conductivity of about $5 \times 10^{-3}$ S/cm at 20° C.

7. A solid proton conductor comprising an electrolytic perovskite in which at least a portion of the ions located therein are replaced by protons, wherein prior to forming said proton conductor the electrolytic perovskite had the following chemical formula:

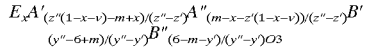

where:
E is a mobile ion;
A' and A" are ions with valences z' and z", respectively;
m is the aggregate valence per A-site;
B' and B" are ions with valences y' and y", respectively;
x is the concentration of mobile ions;
v is the concentration of vacancies; and
E is selected from $Li^+$, $H^+$, $Cu^+$, $Ag^+$, $Na^+$ or $Mg^{2+}$;

m is in the range of 0.0 to 2.2;
A' is selected from $Na^+$ or $K^+$;
A" is selected from $Sr^{2+}$, $Ba^{2+}$ or $La^{3+}$;
B' and B" are selected from $Zr^{4+}$, $Sn^{4+}$, $Ti^{4+}$, $Ce^{4+}$, $Hf^{4+}$, $Nb^{5+}$ or $Ta^{5+}$;
$z' \leq m \leq z"$;
$y \leq 6-m \leq y"$; and
$0 < x < 3/4$, $0 < v < 3/4$, and $x+v > 0.32$.

8. A method for synthesizing a solid proton conductor including the steps of:
forming an electrolytic perovskite that has the following chemical formula:

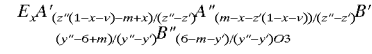

where:
E is a mobile ion selected from $Li^+$, $H^+$, $Cu^+$, $Ag^+$, $Na^+$ or $Mg^{2+}$;
m is the aggregate valence per A-site and is in the range of 0.0 to 2.2,
A' is an ion selected from $Na^+$ or $K^+$ and has a valence z',
A" is an ion selected from $Sr^{2+}$, $Ba^{2+}$ or $La^{3+}$ and has a valence z" such that $z' \leq m \leq z"$,
B' and B" are ions selected from $Zr^{4+}$, $Sn^{4+}$, $Ti^{4+}$, $Ce^{4+}$, $Hf^{4+}$, $Nb^{5+}$ or $Ta^{5+}$ and have respective valences y' and y" such that $y' \leq 6-m \leq y"$,
x is the concentration of mobile ions such that $0 < x < 3/4$, and
v is the concentration of vacancies such that $0 < v < 3/4$ and $x+v > 0.32$;
mixing the A', A", B' and B" ions;
using a forming process to form the electrolytic perovskite; and
replacing at least a portion of the E ions with protons to form a solid proton conductor.

9. The method of claim 8, wherein the step of replacing includes using an acidic solution.

10. The method of claim 8, wherein the step of replacing includes using active electrochemical pumping.

* * * * *